(12) United States Patent
Cromwell et al.

(10) Patent No.: US 11,839,873 B2
(45) Date of Patent: Dec. 12, 2023

(54) VALVELESS FLUIDIC SWITCHING FLOWCHIP AND USES THEREOF

(71) Applicant: Protein Fluidics, Inc., Burlingame, CA (US)

(72) Inventors: Evan Francis Cromwell, Redwood City, CA (US); Wilson Toy, San Francisco, CA (US); Liran Yosef Haller, Berkeley, CA (US); Ori Hoxha, San Francisco, CA (US); Braxton Dunstone, San Francisco, CA (US); Hong Jiao, Santa Clara, CA (US)

(73) Assignee: Protein Fluidics, Inc., Burlingame, CA (US)

( * ) Notice: Subject to any disclaimer, the term of this patent is extended or adjusted under 35 U.S.C. 154(b) by 0 days.

(21) Appl. No.: 17/664,594

(22) Filed: May 23, 2022

(65) Prior Publication Data

US 2022/0362763 A1 Nov. 17, 2022

Related U.S. Application Data

(63) Continuation of application No. 16/398,859, filed on Apr. 30, 2019, now Pat. No. 11,376,589.

(Continued)

(51) Int. Cl.
*C12N 15/10* (2006.01)
*B01L 3/00* (2006.01)
(Continued)

(52) U.S. Cl.
CPC ..... *B01L 3/50273* (2013.01); *B01L 3/502746* (2013.01); *B01L 3/502753* (2013.01);
(Continued)

(58) Field of Classification Search
CPC ........... B01L 3/50273; B01L 3/502746; B01L 3/502753; B01L 3/502761; B01L 3/567;
(Continued)

(56) References Cited

U.S. PATENT DOCUMENTS 3,993,062 A 11/1976 Jess
5,726,404 A 3/1998 Brody
(Continued)

FOREIGN PATENT DOCUMENTS

CN 102740975 A 10/2012
CN 102740976 A 10/2012
(Continued)

OTHER PUBLICATIONS

Ahn, C H, et al., "Disposable smart lab on a chip for point-of-care clinical diagnostics," Proceedings of the IEEE, vol. 92, No. 1, Jan. 2004 pp. 154-173.
(Continued)

*Primary Examiner* — Jennifer Wecker
*Assistant Examiner* — Oyeleye Alexander Alabi
(74) *Attorney, Agent, or Firm* — Weaver Austin Villeneuve & Sampson LLP

(57) ABSTRACT

Provided are valveless microfluidic flowchips comprising fluid flow barrier structures or configurations. Further provided are systems and methods having increased fluid transfer control in a valveless microfluidic flowchip. The systems and methods can be used in the present valveless microfluidic flowchips as well as in currently available valveless microfluidic flowchips.

18 Claims, 33 Drawing Sheets

Related U.S. Application Data

(60) Provisional application No. 62/664,700, filed on Apr. 30, 2018.

(51) Int. Cl.
| | |
|---|---|
| G01N 35/10 | (2006.01) |
| B01L 3/02 | (2006.01) |
| B33Y 80/00 | (2015.01) |
| B33Y 10/00 | (2015.01) |
| B33Y 70/00 | (2020.01) |
| G01N 33/53 | (2006.01) |

(52) U.S. Cl.
CPC ......... *B01L 3/502761* (2013.01); *B01L 3/567* (2013.01); *G01N 33/5304* (2013.01); *B01L 2200/027* (2013.01); *B01L 2200/0647* (2013.01); *B01L 2200/0684* (2013.01); *B01L 2300/048* (2013.01); *B01L 2300/0636* (2013.01); *B01L 2300/0883* (2013.01); *B01L 2300/14* (2013.01); *B01L 2300/165* (2013.01); *B01L 2400/049* (2013.01); *B01L 2400/0487* (2013.01); *B01L 2400/06* (2013.01); *B01L 2400/086* (2013.01); *B01L 2400/088* (2013.01)

(58) Field of Classification Search
CPC ....... B01L 2200/027; B01L 2200/0647; B01L 2200/0684; B01L 2300/048; B01L 2300/0636; B01L 2300/0883; B01L 2300/14; B01L 2300/165; B01L 2400/0487; B01L 2400/049; B01L 2400/06; B01L 2400/086; B01L 2400/088; G01N 33/5304
See application file for complete search history.

(56) References Cited

U.S. PATENT DOCUMENTS

| | | | |
|---|---|---|---|
| 6,086,825 | A | 7/2000 | Sundberg et al. |
| 6,568,910 | B1 | 5/2003 | Parce |
| 6,811,668 | B1 | 11/2004 | Berndt et al. |
| 6,989,130 | B2 | 1/2006 | Deshmukh |
| 7,445,926 | B2 | 11/2008 | Mathies et al. |
| 7,601,270 | B1 | 10/2009 | Unger et al. |
| 7,695,603 | B2 | 4/2010 | Paul et al. |
| 8,075,854 | B2 | 12/2011 | Yang et al. |
| 8,122,901 | B2 | 2/2012 | Zeng et al. |
| 8,215,338 | B2 | 7/2012 | Delattre et al. |
| 8,772,017 | B2 | 7/2014 | Battrell et al. |
| 9,733,239 | B2 | 8/2017 | Jiao et al. |
| 9,956,557 | B2 | 5/2018 | Jiao et al. |
| 9,956,558 | B2 | 5/2018 | Jiao et al. |
| 11,376,589 | B2 | 7/2022 | Cromwell et al. |
| 2002/0003001 | A1 | 1/2002 | Weigl et al. |
| 2002/0043463 | A1 | 4/2002 | Shenderov |
| 2002/0150512 | A1 | 10/2002 | Kellogg et al. |
| 2004/0055891 | A1 | 3/2004 | Pamula et al. |
| 2004/0109793 | A1 | 6/2004 | McNeely et al. |
| 2004/0202579 | A1 | 10/2004 | Larsson et al. |
| 2004/0228771 | A1 | 11/2004 | Zhou et al. |
| 2005/0130292 | A1 | 6/2005 | Ahn et al. |
| 2005/0217742 | A1 | 10/2005 | Bohm |
| 2005/0255003 | A1 | 11/2005 | Summersgill et al. |
| 2007/0075010 | A1 | 4/2007 | Gilbert et al. |
| 2007/0113908 | A1 | 5/2007 | Lee et al. |
| 2007/0166199 | A1 | 7/2007 | Zhou et al. |
| 2008/0281090 | A1 | 11/2008 | Lee et al. |
| 2009/0165876 | A1 | 7/2009 | Atkin et al. |
| 2010/0021349 | A1 | 1/2010 | Boehm et al. |
| 2011/0120562 | A1* | 5/2011 | Tan .................. G01N 33/54366 137/583 |
| 2011/0301535 | A1 | 12/2011 | Takayama et al. |
| 2012/0329142 | A1 | 12/2012 | Battrell et al. |
| 2013/0130262 | A1 | 5/2013 | Battrell et al. |
| 2014/0287966 | A1 | 9/2014 | Gray et al. |
| 2015/0132742 | A1 | 5/2015 | Thuo et al. |
| 2015/0298123 | A1 | 10/2015 | Block, III et al. |
| 2016/0074864 | A1 | 3/2016 | Tsao et al. |
| 2016/0250639 | A1 | 9/2016 | Devaraju et al. |
| 2017/0021351 | A1 | 1/2017 | Jiao et al. |
| 2017/0021352 | A1* | 1/2017 | Jiao .................. B01L 3/502746 |
| 2017/0021353 | A1 | 1/2017 | Jiao et al. |

FOREIGN PATENT DOCUMENTS

| | | |
|---|---|---|
| WO | WO-0078456 A1 | 12/2000 |
| WO | WO-2008103824 A1 | 8/2008 |

OTHER PUBLICATIONS

Andersson, H., et al. "Hydrophobic valves of plasma deposited octafluorocyclobutane in DRIE channels," Sensors Actuators B, 2001, 75, pp. 136-141.

Andersson, H., et al., "Micromachined filter-chamber array with passive valves for biochemical assays on beads," Electrophoresis, 2001, 22, pp. 249-257.

CA Office Action dated Mar. 22, 2022, in CA Application No. 2992434.

CA Office Action dated Mar. 31, 2022 in Application No. CA2992447.

Cho, H., et al., "How the capillary burst microvalve works," Journal of Colloid and Interface Science, vol. 306, Iss. 2, Feb. 15, 2007, pp. 379-385.

CN Decision of Rejection dated Sep. 3, 2020, issued in Application No. 201680055786.4.

CN Office Action dated Jan. 21, 2022, in Application No. CN201980044332 with English translation.

CN Office Action dated Mar. 20, 2019, issued in Application No. 201680055786.4.

CN Office Action dated Nov. 18, 2019, issued in Application No. 201680055786.4.

CN Office Action dated Nov. 26, 2019, issued in Application No. 2016/0055823.1.

CN Office Action dated Oct. 10, 2020, issued in Application No. 2016/0055823.1.

CN Third Office Action dated Apr. 7, 2020, issued in Application No. 201680055786.4.

Duffy, D.C., et al., "Microfabricated centrifugal microfluidic systems: characterization and multiple enzymatic assays," Anal. Chem., 1999, 71, pp. 4669-4678.

Ellinas, K., et al., "Superhydrophobic, passive microvalves with controllable opening pressure and applications in flow control," 17th International Conference on Miniaturized Systems for Chemistry and Life Sciences, Oct. 27-31, 2013, pp. 344-346.

Ellinas, K., et al., "Superhydrophobic, passive microvalves with controllable opening threshold: Exploiting plasma nanotextured microfluidics for a programmable flow switchboard," Microfluidics & Nanofluidics, 2014, DOI 10.1007/s10404-014-1335-9, pp. 489-498.

EP Extended Search Report dated Nov. 12, 2018, issued in Application No. 16830997.9.

EP Office Action dated Feb. 21, 2022, in Application No. EP16830997.9.

EP Office Action dated Mar. 14, 2022, in Application No. EP16830993.8.

EP Search Report dated Nov. 13, 2018, in Application No. EP16830993.8.

Extended European Search Report issue in Application No. 19796922.3 dated Jan. 4, 2022.

Feng, Y., et al., "Passive valves based on hydrophobic microfluidics," Sensors and Actuators A: vol. 108, Nov. 15, 2003, pp. 138-143.

Friend, J., et al., "Microscale acoustofluidics: Microfluidics driven via acoustics and ultrasonics," Rev. Mod. Phys., vol. 83, No. 2, Apr.-Jun. 2011, pp. 647-687.

Grover, WH, et al., "Monolithic membrane valves and diaphragm pumps for practical large-scale integration into glass microfluidic devices." Sensors and Actuators B: Chemical B 89, 2003, pp. 315-323.

(56) References Cited

OTHER PUBLICATIONS

Harrison, D.J., et al., "Capillary electrophoresis and sample injection systems integrated on a planar glass chip," Analytical chemistry 64 (17), 1992, pp. 1926-1932.
International Preliminary Report on Patentability dated Feb. 8, 2018 in Application No. PCT/US2016/039619.
International Preliminary Report on Patentability dated Feb. 8, 2018 in Application No. PCT/US2016/040071.
International Preliminary Report on Patentability dated Nov. 12, 2020 in Application No. PCT/US2019/029879.
International Search Report and Written Opinion dated Nov. 10, 2016 in Application No. PCT/US2016/040071.
International Search Report and Written Opinion dated Oct. 14, 2016 in Application No. PCT/US2016/39619.
International Search Report and Written Opinion dated Aug. 14, 2019, in PCT Application No. PCT/US2019/029879.
Irimia, D., "Capillary Force Valves," in Encyclopedia of Micro-and Nanofluidics edited by Li, Dongqing. 2008, 6 pages.
Johnson, R.D., et al., "Development of a fully integrated analysis system for ions based on ion-selective optodes and centrifugal microfluidics," Anal. Chem., 2001, vol. 73, pp. 3940-3946.
Kim, S.J., et al., "Preprogrammed capillarity to passively control system-level sequential and parallel microfluidic flows," Lab Chip., Jun. 7, 2013, vol. 13, pp. 2091-2098.
Leu, T-S et al., "Pressure barrier of capillary stop valves in micro sample separators," Sensors and Actuators A, vol. 115, 2004, pp. 508-515.
Luong, T-D., et al., "Surface Acoustic Wave Driven Microfluidics—A Review," Micro and Nanosystems, vol. 2(3), 2010, pp. 1-9.
Man, P. F., et al., "Microfabricated capillary-driven stop valve and sample injector," IEEE, 1998, pp. 45-50.
McNeely, et al., "Sample Processing with Hydrophobic Microfluidics," JALA, 1999, 4(4), pp. 30-33.
McNeely, et al., "Hydrophobic microfluidics." in Proc. SPIE, Ahn, C. H.; Frazier, A. B., Eds., 1999, 3877, pp. 210-220.
Melin, J., et al., "A liquid-triggered liquid microvalve for on-chip flow control," Sensors Actuators B, 2004, vol. 100, pp. 463-468.
Miller, et al., "A digital microfluidic approach to homogeneous enzyme assays," Anal Chem, 2008, vol. 80, pp. 1614-1619.
Mosadegh, B, et al., "Integrated Elastomeric Components for Autonomous Regulation of Sequential and Oscillatory Flow Switching in Microfluidic Devices," Nature Physics, Jun. 2010, vol. 6, pp. 433-437.
Oh K.W., et al., "A review of microvalves," Journal of Micromechanics and Microengineering, May 2006, vol. 16 (5), pp. 13-39.
Puckett, L. G, et al., "Investigation into the applicability of the centrifugal microfluidics platform for the development of protein-ligand binding assays incorporating enhanced green fluorescent protein as a fluorescent reporter," Anal. Chem., 2004, vol. 76, pp. 7263-7268.
Srinivasan, V., et al., "Droplet-based microfluidic lab-on-a-chip for glucose detection," Anal. Chem. Acta., 2004, vol. 507, pp. 145-150.
Teh, S. Y., et al., "Droplet microfluidics," Lab Chip, 2008, vol. 8, pp. 198-220.
Thorsen, T., et al., "Microfluidic large-scale integration," Science, Oct. 18, 2002, vol. 298, pp. 580-584.
Unger M. A., et al., "Monolithic microfabricated valves and pumps by multilayer soft lithography," Science, vol. 288, Apr. 7, 2000, 288 (5463): pp. 113-116.
U.S. Corrected Notice of Allowance dated Apr. 14, 2022 in U.S. Appl. No. 16/398,859.
U.S. Final Office Action dated Sep. 12, 2017 in U.S. Appl. No. 14/808,929.
U.S. Final Office Action dated Sep. 27, 2017 in U.S. Appl. No. 14/808,933.
U.S. Non Final office Action dated Aug. 2, 2021 in U.S. Appl. No. 16/398,859.
U.S. Notice of Allowance dated Feb. 17, 2022 in U.S. Appl. No. 16/398,859.
U.S. Notice of Allowance dated Feb. 22, 2018 in U.S. Appl. No. 14/808,933.
U.S. Notice of Allowance dated Feb. 28, 2022 in U.S. Appl. No. 16/398,859.
U.S. Notice of Allowance dated Jun. 29, 2017 in U.S. Appl. No. 14/808,939.
U.S. Notice of Allowance dated Mar. 20, 2018 in U.S. Appl. No. 14/808,929.
U.S. Notice of Allowance dated Mar. 25, 2022 in U.S. Appl. No. 16/398,859.
U.S. Office Action dated Mar. 20, 2017 in U.S. Appl. No. 14/808,929.
U.S. Office Action dated Mar. 21, 2017 in U.S. Appl. No. 14/808,933.
U.S. Office Action dated Mar. 23, 2017 in U.S. Appl. No. 14/808,939.
Yamada, M., et al., "Nanoliter-sized liquid dispenser array for multiple biochemical analysis in microfluidic devices," Anal. Chem., 2004, vol. 76, pp. 895-899.
Yokoyama Y, et al., "Thermal micro pumps for a loop-type micro channel," Sensors Actuators A, 2004, vol. 111, pp. 123-128.
CN Office Action dated Oct. 10, 2022 in Application No. CN201980044332 with English translation.
CN Office Action dated Mar. 31, 2023, in Application No. CN201980044332 with English translation.
CN Office Action dated Aug. 25, 2022, in application No. CN201680055786.4.

* cited by examiner

A

B

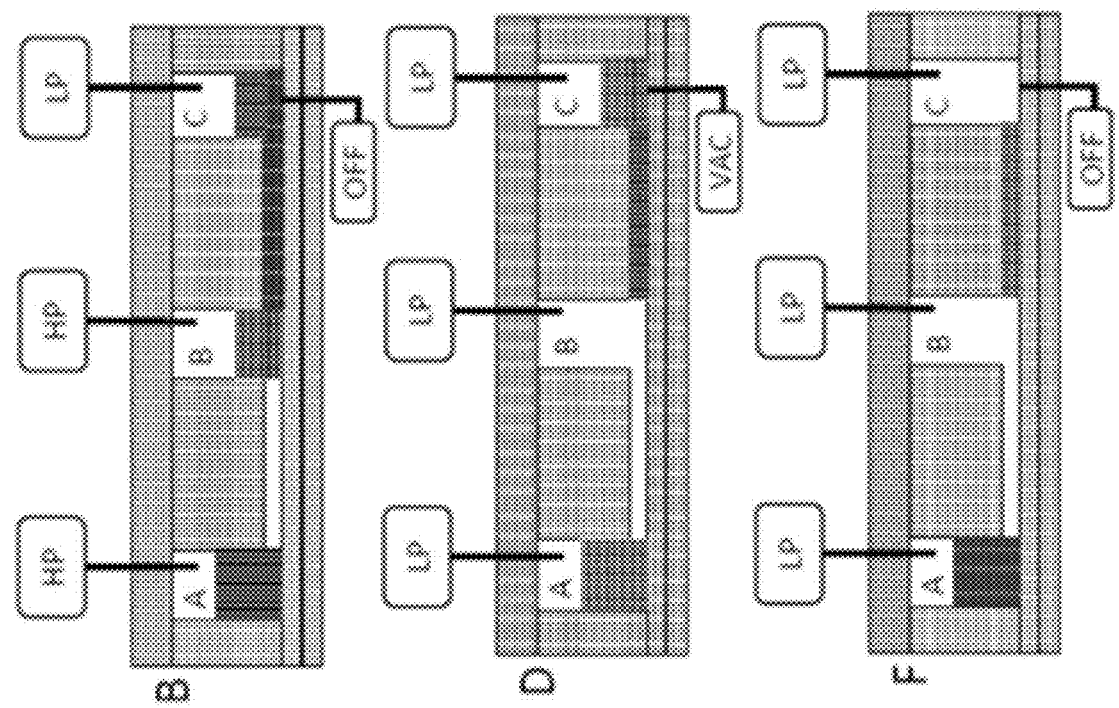
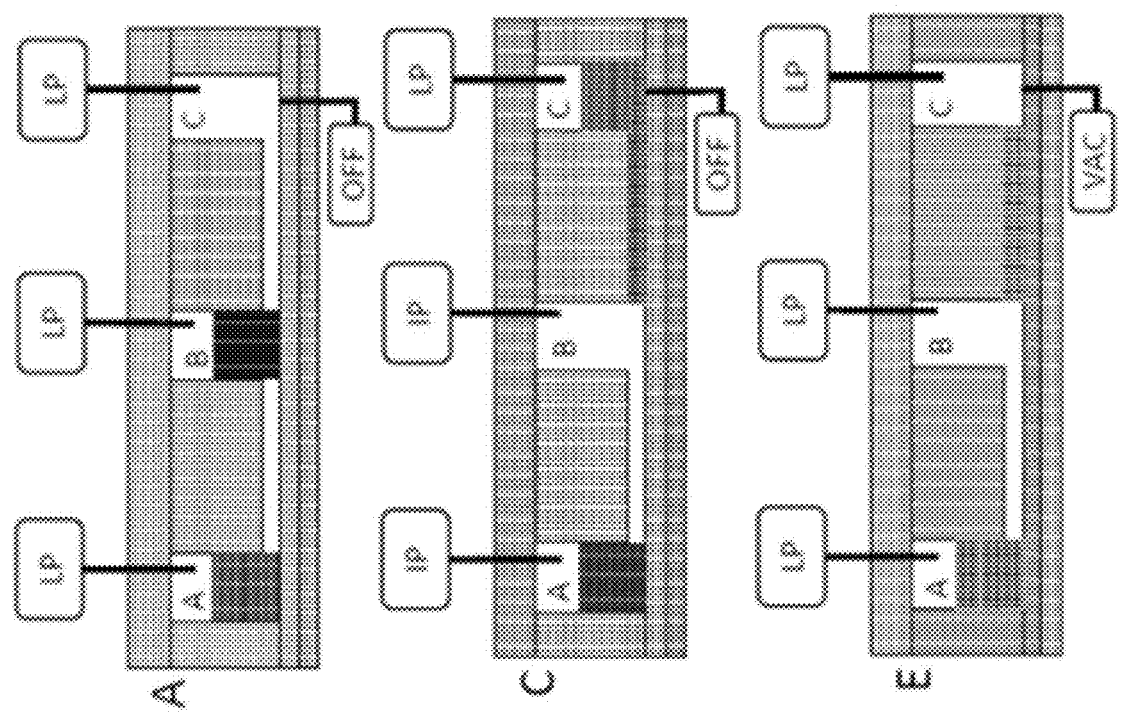
Fig. 6A-6F

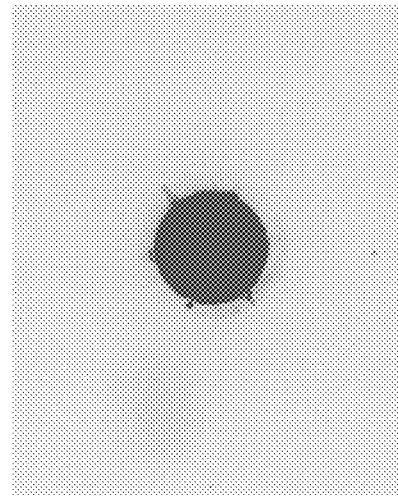
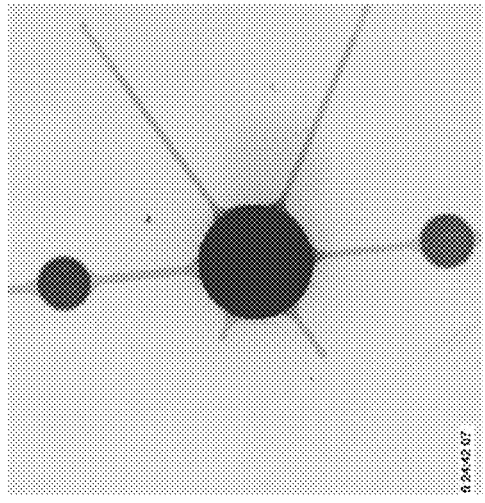
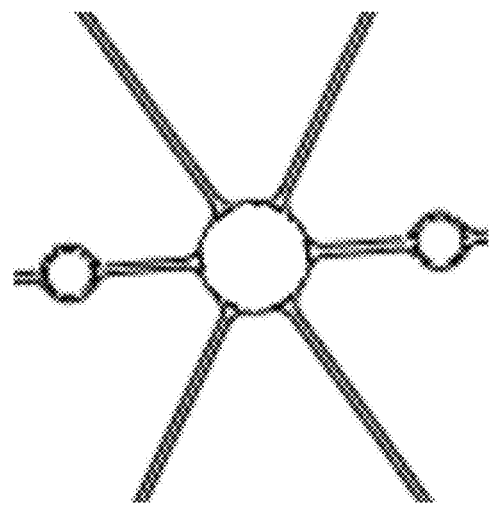
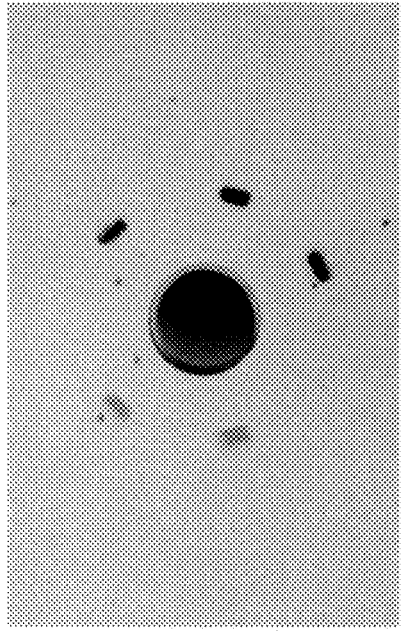
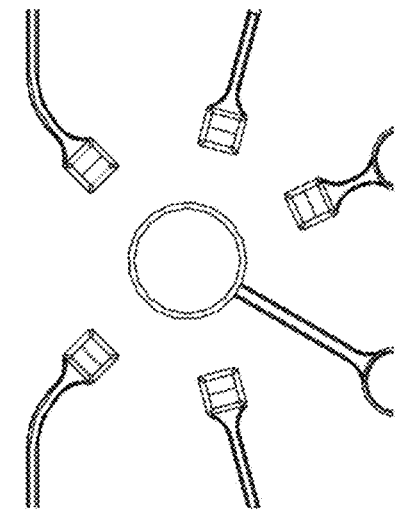
Fig. 16A-16B

$EC_{50}$ Values (μM)

| Compounds | IL-8 | IL-6 | MCP-1 |
|---|---|---|---|
| SB202190 | 25.5 ± 12.5 | 3.14 ± 0.74 | 29.2 ± 11.9 |
| MG-132 | no effect | 3.74 ± 0.696 | 0.223 ± 0.094 |
| AG-126 | 52.02 ± 199 | 24.4 ± 7.78 | 65.9 ± 64.8 |

*Fig. 20D*

IL-6 Assay Results

|  | FC-1 | FC-2 |
|---|---|---|
| Assay Window | 1.56 | 2.01 |
| StDev (OD) | 0.15 | 0.05 |
| LOD (pg/well) | 23 | 1.8 |

*Fig. 23B*

| EC$_{50}$, µM | IL-8 | IL-1β | TNFα |
|---|---|---|---|
| PDTC | 201 | 42 | 63 |
| SB202190 | 6.6 | 9.8 | 6.4 |
| Moxifloxacin | 17.4 | 9.9 | 17.9 |

*Fig. 25B*

VALVELESS FLUIDIC SWITCHING FLOWCHIP AND USES THEREOF

STATEMENT OF GOVERNMENTAL SUPPORT

This invention was made with government support under Contract No. EP-D-15-007 awarded by the United States Environmental Protection Agency. The government has certain rights in the invention.

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

STATEMENT OF JOINT RESEARCH AGREEMENT

The subject matter and the claimed invention were made by or on behalf of HJ Science & Technology, Inc. of Berkeley, CA and Protein Fluidics, Inc. of Burlingame, CA, under a joint research agreement titled "DEVELOPMENT AGREEMENT between HJ SCIENCE & TECHNOLOGY, INC. and PROTEIN FLUIDICS, INC." The subject matter disclosed was developed and the claimed invention was made by, or on behalf of, one or more parties to the joint research agreement that was in effect on or before the effective filing date of the claimed invention, and the claimed invention was made as a result of activities undertaken within the scope of the joint research agreement.

BACKGROUND

Reconfigurable microfluidic systems based on networks of hydrophobic channels using valve-less fluidic switching can be used for multiple applications. Challenges are encountered with implementation of this technology due to robustness of the hydrophobic barriers and the requirement of various fluid transfer events.

Currently known reconfigurable microfluidic systems utilize hydrophobic barriers (HPB) between connected wells and channels to control fluid movement. The devices use straight channels connected to wells, and processes for fluid control that implement three pressures: High, Low, and Vacuum, where the low pressure is nominally atmospheric pressure, the high gas pressure moves fluid from a source well, through a connecting channel, to a destination well, and the destination well is kept at low pressure (atmosphere) during this transfer. At the end of a pressure cycle step to move fluid from a source well to a destination well, the connecting channel has been emptied to reestablish the hydrophobic barrier between the source well and channel.

SUMMARY

In one aspect, provided is a valveless microfluidic flowchip. In some embodiments, the flowchip comprises one or more networks of microfluidic cavities connected by microfluidic channels, wherein reservoirs are cavities that are connected to only one channel each, and nodes are cavities that are connected to two or more channels each; wherein: i) a first plurality of the channels connect only two cavities each; ii) a second plurality of the channels comprise one or more fluid flow barrier structures or configurations; and iii) a plurality of the cavities include a gas pressure port. In some embodiments, the first and second pluralities of the channels can be the same, different, or partially the same (e.g., overlapping). In some embodiments, the one or more fluid flow barrier structures or configurations are located at or near an interface of the cavity with the channel. In some embodiments, the one or more fluid flow barrier structures or configurations increase channel resistance to fluid flow or the pressure required to move fluid by at least about 20%, e.g., at least about 25%, 30%, 35%, 40%, 45%, 50%, or more, e.g., in comparison to a channel that does not have a fluid flow barrier structure or configuration. In some embodiments, one or more of the microfluidic channels are hydrophobic or comprise a hydrophobic coating. In some embodiments, the one or more fluid flow barrier structures or configurations comprise a constriction or narrowing of the channel, ribs, and/or a non-linear path. In some embodiments, the one or more fluid flow barrier structures or configurations comprise a geometry selected from the group consisting of serpentine or S-curve geometry, a junction, a fishbone or a split channel. In some embodiments, the one or more fluid flow barrier structures or configurations comprise a void (e.g., a sealed cavity) located in-line with the channel. In some embodiments, one or more or a plurality of the cavities are not cylindrical and comprise a concave curvature at the junction of the cavity with one or more channels, such that the cavity forms peninsulas that extend from the cavity towards one or more channels (e.g., the cavity is in the shape of a lilypad). In some embodiments, one or more or a plurality of the cavities comprises a perpendicular entrance of one or more channels into the cavity, such that there is a sharp (e.g., of about 90°, e.g., not gradual or flared) change in geometry where the channel enters the cavity. In some embodiments, the nodes are configured such that entrance (e.g., input, transfer) channel and exit (e.g., output, assay) channel junctions are located in different vertical planes, e.g., where the input channel enters at the side of the node and the output channel exits from the center of the node. In some embodiments, a region is created between the entrance and exit channels that can retain a defined amount of fluid when a cavity is emptied during a transfer process. In some embodiments, the flowchip comprises a hydrophobic fluidic layer (115) comprised of one or more polymers selected from the group consisting of polypropylene (PP), a cyclic olefin polymer (COP), a cyclic olefin copolymer (COC); a fluoropolymer such as polytetrafluoroethylene (PTFE), fluorinated ethylene propylene (FEP, a copolymer of hexafluoropropylene and tetrafluoroethylene), perfluoro alkoxy polymer resin (PFA); and a silicone polymer such as polydimethylsiloxane (PDMS). In some embodiments, the polymers can be modified to increase their hydrophobicity through use of additives, surface coatings, or surface modifications. In some embodiments, one or more or a plurality of the cavities can be connected with up to 4, 5, 6, 7, 8, 9, 10, 11, 12, 13, 14, 15 or 16 channels each. In some embodiments, each network in the one or more networks comprises an input/output channel, the input/output channel having a greater resistance to fluid flow than that of the microfluidic channels. In some embodiments, each flowchip can contain a plurality of networks spaced at regular intervals with the number, spacing and density of networks defined by industry standards such as American National Standards Institute (ANSI) Society for Laboratory Automation and Screening (SLAS) 4-2004 (R2012).

In a further aspect, provided are valveless microfluidic systems. In some embodiments, the systems comprise a flowchip as described above and herein, wherein the system comprises a pressure sequencer including a set of gas valves, the pressure sequencer connected by pneumatic delivery channels to: (1) a high gas pressure gas source; (2) an intermediate gas pressure gas source; (3) a low pressure gas source; and optionally, (4) a partial vacuum pressure gas source; and to at least one cavity in the flow chip. In some embodiments, the systems comprise: a) a flowchip comprising: one or more networks of microfluidic cavities connected by microfluidic channels, wherein: reservoirs are cavities that are connected to only one channel each, and nodes are cavities that are connected to two or more channels each, wherein: i) a first plurality of the channels connect only two cavities each; ii) a second plurality of the channels have a greater resistance to fluid flow than that of the nodes; and iii) a plurality of the cavities include a gas pressure port; and b) a pressure sequencer comprising a set of gas valves, the pressure sequencer connected by pneumatic delivery channels to: (1) a high gas pressure gas source; (2) an intermediate gas pressure gas source; (3) a low gas pressure gas source; and optionally, (4) a partial vacuum pressure gas source; and to at least one cavity within the flowchip. In some embodiments, the first and second pluralities of the channels can be the same, different, or partially the same (e.g., overlapping). In some embodiments, the pressure sequencer is configured to apply a high gas pressure, an intermediate gas pressure, a low gas pressure, and optionally, a partial vacuum pressure to the at least one cavity according to pressure sequence data, where the high gas pressure is greater than the intermediate gas pressure, the intermediate gas pressure is greater than the low gas pressure, and the low gas pressure is greater than the partial vacuum gas pressure, and the partial vacuum pressure is less than atmospheric pressure. In some embodiments, the pressure sequencer is configured to concurrently apply a combination of gas pressure and partial vacuum to at least one cavity. In some embodiments, the second plurality of the channels comprises one or more fluid flow barrier structures or configurations. In some embodiments, the one or more fluid flow barrier structures or configurations are located at or near an interface of the cavity with the channel. In some embodiments, the one or more fluid flow barrier structures or configurations increase channel resistance to fluid flow or the pressure required to move fluid by at least 20%, e.g., at least about 25%, 30%, 35%, 40%, 45%, 50%, or more, in comparison to a channel that does not have a fluid flow barrier structure or configuration. In some embodiments, one or more of the microfluidic channels are hydrophobic or comprise a hydrophobic coating. In some embodiments, the one or more fluid flow barrier structures or configurations comprise a constriction or narrowing of the channel, ribs and/or a non-linear path. In some embodiments, the one or more fluid flow barrier structures or configurations comprises a geometry selected from the group consisting of serpentine or S-curve geometry, a junction, a fishbone or a split channel. In some embodiments, the one or more fluid flow barrier structures or configurations comprise a void (e.g., a sealed cavity) located in-line with the channel. In some embodiments, one or more or a plurality of the cavities comprises a perpendicular entrance of one or more channels into the cavity, such that there is a sharp (e.g., of about 90°, e.g., not gradual or flared) change in geometry where the channel enters the cavity. In some embodiments, the nodes are configured such that entrance (e.g., input, transfer) channel and exit (e.g., output, assay) channel junctions are located in different vertical planes, e.g., where the input channel enters at the side of the node and the output channel exits from the center of the node. In some embodiments, a region is created between the entrance and exit channels that can retain a defined amount of fluid when a cavity is emptied during a transfer process.

In a related aspect, provided is a system for moving a quantity of liquid from a source cavity to a destination cavity in a network of microfluidic cavities, wherein the source cavity and the destination cavity are separated by a valveless microfluidic channel having a resistance to fluid flow greater than that of the source cavity, the method comprising: (i) a receptacle for receiving and engaging with a flowchip comprising the network of microfluidic cavities; (ii) a pressure sequencer comprising a set of gas valves and configured to be connected to a first gas source for producing a high gas pressure in microfluidic cavities, a second gas source for producing a low pressure in microfluidic cavities, and a third gas source for producing an intermediate gas pressure in microfluidic cavities, and optionally, a fourth partial vacuum source wherein the high gas pressure is greater than the low pressure, the intermediate gas pressure is less than the high gas pressure but greater than the low pressure, and the intermediate gas pressure is insufficiently great overcome resistance to fluid flow in the microfluidic channel when the source cavity is substantially empty of the liquid, and the partial vacuum is less than atmospheric pressure, wherein the pressure sequencer can apply any pressure state to any cavity within the flowchip; and (iii) a controller configured to direct the pressure sequencer to: (a) apply the high gas pressure to the source cavity and to all other cavities connected to the source cavity excepting the destination cavity, while applying the low pressure to the destination cavity, to move a portion of the quantity of liquid from the source cavity, through the microfluidic channel, and to the destination cavity, and (b) apply an intermediate gas pressure to the source cavity before the quantity of liquid is completely removed from the source cavity, wherein the intermediate gas pressure is sufficiently great to push at least some of the quantity of liquid remaining after (a) to the destination cavity, but avoids introducing gas into the microfluidic channel. In some embodiments, the method comprises further applying partial vacuum to a destination cavity or other connecting cavity, the partial vacuum being applied for a time sufficient to evacuate fluid from the destination cavity. In some embodiments, a defined amount of fluid remains in the source cavity in a region between the entrance and exit channels.

In some embodiments of the systems, the pressure sequencer is configured to apply a one or more pressure modes selected from the group consisting of constant pressure, pulsing pressures, increased ramping pressures and decreased ramping pressures. In some embodiments, the pressure sequencer is configured to apply pulsing pressures and a pulse width modulation (PWM) with a duty factor in the range of from about 1% to about 5%, 10%, 20%, 30%, 40%, 50%, 60%, 70%, 80% or 90%. In some embodiments, the pressure sequencer is configured to apply increased and/or decreased ramping pressures comprising rise and/or fall times in the range of about 10 msec to about 20 msec, 50 msec, 100 msec, 250 msec, 500 msec, 750 msec or 1 sec. In some embodiments, one or more of the microfluidic channels are hydrophobic or comprise a hydrophobic coating. In some embodiments, the system comprises a flowchip as described above and herein. In some embodiments, i) the high gas pressure is in the range of about 5 kPa to about 10 kPa, 20 kPa, 30 kPa, 40 kPa, 50 kPa, 60 kPa, 70 kPa, 80 kPa, 90 kPa or 100 kPa, e.g., in the range of about 10 kPa to about 60 kPa; and/or ii) the intermediate gas pressure is in the range of about 0.5 kPa to about 1 kPa, 2 kPa, 3 kPa, 4 kPa, 5 kPa, 6 kPa, 7 kPa, 8 kPa, 9 kPa or 10 kPa; and/or iii) the optional partial vacuum pressure is in the range of about −5 kPa to about −10 kPa, −20 kPa, −30 kPa, −40 kPa, −50 kPa, −60 kPa, −70 kPa, −80 kPa, −90 kPa, or −100 kPa. Generally, the high gas pressure is greater than the intermediate gas pressure, the intermediate gas pressure is greater than the low gas pressure, and the low gas pressure is greater than the partial vacuum gas pressure, and the partial vacuum pressure is less than atmospheric pressure. In some embodiments, fluid flow rate under high gas pressure through the first plurality of microfluidic channels is from about 0.1 μL/second to about 0.2, 0.3, 0.4, 0.5, 0.6, 0.7, 0.8, 0.9, 1.0, 2.0, 3.0, 4.0, 5.0, 6.0, 7.0, 8.0, 9.0 or 10.0 μL/second. In some embodiments, fluid flow rate under intermediate gas pressure through the first plurality of microfluidic channels is from about 0.01 μL/second to about 0.05, 0.1, 0.2, 0.3, 0.4, 0.5, 0.6, 0.7, 0.8, 0.9 or 1.0 μL/second. Generally, the fluid flow rate under high gas pressure is faster than the fluid flow rate under intermediate gas pressure. In some embodiments, a plurality of the microfluidic channels present a hydrophobic pressure barrier to fluid flow that is less than the pressure difference between the high gas pressure and the low gas pressure. In some embodiments, the pressure sequencer is configured to apply or follow a fluid transfer rule in which: (1) high gas pressure is applied to an origin or source cavity from which a fluid is transferred and low gas pressure is applied to a destination cavity to which the fluid is transferred, the high gas pressure being applied for a time t(1) sufficient to overcome hydrophobic and/or hydrostatic barriers and start fluid flowing from the origin or source cavity into a microfluidic channel connecting the origin or source cavity to the destination cavity; (2) intermediate gas pressure is applied to the origin or source cavity and low pressure is applied to the destination cavity such that fluid continues to move through the connecting channel, the intermediate gas pressure being applied for a time t(2) sufficient to empty the origin or source cavity of fluid but of a pressure insufficient to expel fluid out of the channel; whereby the origin or source cavity is emptied of fluid and the fluid is moved into the channel and destination cavity. In some embodiments, a defined amount of fluid remains in the source cavity in a region between the entrance and exit channels. In some embodiments, the pressure sequencer is configured to follow a fluid transfer rule further in which: (3) partial vacuum is applied to the destination channel while low pressure is applied to the source cavity 210 such that fluid is evacuated or removed from the destination cavity 220 through the gas port. In some embodiments, the pressure sequencer is configured to concurrently apply a combination of gas pressure and partial vacuum to at least one cavity. In some embodiments, partial vacuum is applied to the destination cavity 220 through a port or channel in fluid communication with the bottom surface of the destination cavity 230 and fluid is evacuated or removed from the bottom surface of the destination cavity. See, e.g., FIGS. 5 and 6. In some embodiments, gas pressure is applied to the destination cavity 220 through a port or channel in fluid communication with the top opening of the destination cavity 240 (e.g., above or over the meniscus of the fluid in the destination cavity) concurrently with partial vacuum being applied to the destination cavity through a port or channel in fluid communication with the bottom surface of the destination cavity 230 (e.g., below or under the fluid in the destination cavity). In some embodiments, time t(1) is for a time period that is stopped or ended before the quantity of liquid is completely removed from the source cavity, e.g., a time period sufficient to drain at least about 10% and up to about 20%, 30%, 40%, 50%, 60%, 70%, 80% or 90% of the fluid volume from the origin or source cavity. In some embodiments, the pressure sequencer is further connected to a very high gas pressure source, and the pressure sequencer is configured to apply a very high gas pressure, wherein the very high gas pressure is greater than the high gas pressure. In some embodiments, the very high gas pressure is at least about 100 kPa, e.g., at least about 125 kPa, 150 kPa, 175 kPa, 200 kPa, or higher. In some embodiments, the pressure sequencer is configured to apply or follow a fluid transfer rule in which the partial vacuum gas pressure is applied to a destination cavity to which a fluid is drawn via its input/output channel and low gas pressure is applied to any other cavity connected to the destination cavity by a channel. In some embodiments, one or more networks comprise j rows and k columns of cavities, j and k being positive integers, cavities in each row or column being connected in series.

In a further aspect, provided are methods for arranging fluid in a microwell plate. In some embodiments, the methods comprise operating the valveless microfluidic system as described above and herein according to a set of pressure sequence data that causes the fluid to be drawn into the system from an origin or source cavity of the microwell plate and expelled into a destination cavity of the microwell plate, wherein air is not introduced into a microfluidic channel downstream of an origin or source cavity.

In a further aspect, provided are methods for performing a homogenous assay with j samples and k reagents. In some embodiments, the methods comprise operating the valveless microfluidic system as described above and herein, with pressure sequence data that causes each of the j samples to be exposed to the k reagents thereby producing j output solutions, wherein air is not introduced into a microfluidic channel downstream of an origin or source cavity.

In a further aspect, provided are methods for performing a multiplexed immunoassay. In some embodiments, the methods comprise operating the valveless microfluidic system as described above and herein, wherein the system comprises two or more networks, the system operated according to pressure sequence data such that the pressure sequencer directs fluid flows in the system that cause different kinds of sample-analyte-capture-analyte reactions to occur in different networks, but the same kind of detection reagent reaction to occur in a plurality of networks, wherein air is not introduced into a microfluidic channel downstream of an origin or source cavity. In some embodiments, the immunoassay fluid comprises a buffer having a pH in the range of 6-11, e.g., pH in the range of 6-9, e.g., a pH in the range of about 7-9 or a pH in the range of 9-11, one or more blocking agents or protein solutions and one or more surfactants. In specific embodiments, the immunoassay fluid comprises phosphate buffered saline (PBS), tris-buffered saline (TBS) or a bicarbonate buffer, albumin (e.g., bovine serum albumin (BSA)), Tween-20, Triton-X, or other surfactants and optionally glycerol.

In a further aspect, provided are methods of moving a quantity of liquid from a source cavity to a destination cavity in a network of microfluidic cavities. In some embodiments, the methods are executed using a valveless microfluidic flowchip having a source cavity and a destination cavity separated by a valveless microfluidic channel having a resistance to fluid flow greater than that of the source cavity. In some embodiments, the methods comprise: (a) applying a high gas pressure to the source cavity, and all other cavities connected to the source cavity excepting the destination cavity, while applying a low pressure to the destination cavity to move a portion of the quantity of liquid from the source cavity, through the microfluidic channel, and to the destination cavity, wherein the high gas pressure is greater than the low pressure; and (b) applying an intermediate gas pressure to the source cavity before the quantity of liquid is completely removed from the source cavity, wherein the intermediate gas pressure is lower than the high gas pressure but higher than low pressure, and wherein the intermediate gas pressure is sufficiently great to push at least some of the quantity of liquid remaining after (a) to the destination cavity, but insufficiently great overcome resistance to fluid flow in the microfluidic channel, and thereby avoid introducing gas into the microfluidic channel. In some embodiments, the pressure sequencer is configured to follow a fluid transfer rule further in which partial vacuum is applied to the destination channel while low pressure is applied to the source cavity such that fluid is evacuated or removed from the destination cavity through the gas port. In some embodiments, partial vacuum is applied to the destination cavity 220 through a port or channel in fluid communication with the bottom surface of the destination cavity 230 and fluid is evacuated or removed through the bottom surface of the destination cavity. In some embodiments, gas pressure is applied to the destination cavity 220 through a port or channel in fluid communication with the top opening of the destination cavity 240 (e.g., above or over the meniscus of the fluid in the destination cavity) concurrently with partial vacuum being applied to the destination cavity through a port or channel in fluid communication with the bottom surface of the destination cavity 230 (e.g., below or under the fluid in the destination cavity). In some embodiments, the one or more of the microfluidic channels are hydrophobic or comprise a hydrophobic coating. In some embodiments, the intermediate gas pressure is insufficiently great to introduce gas into the microfluidic channel even when all of the quantity of liquid has been removed from the source cavity. In some embodiments, less than about 90% of the liquid is removed from the source cavity before applying the intermediate gas pressure. In some embodiments, the method is performed using a system as described above and herein.

In a further aspect, methods of performing assays using cells or cellular structures are providing. The methods may involve providing a microfluidic flowchip comprising one or more networks of microfluidic cavities connected by microfluidic channels, wherein nodes are cavities that are connected to two or more channels each, wherein at least one node comprises a first junction with an input channel and a second junction with an output channel, wherein the first junction and the second junction are located at different vertical planes, and wherein the node includes a main region and a defined region having a defined volume, the defined region disposed below the main region; and directing cells or cellular structures from the main region to the defined region. In some embodiments, directing cells or cellular structures involves to the defined region comprises flowing fluid from the input channel through the defined region to the output channel. In some embodiments, directing cells or cellular structures comprises to the defined region includes introducing fluid from the input channel into the main region at an angle. In some embodiments, the method is performed using a flowchip or system as described above and herein.

These and other aspects are described below with reference to the drawings.

BRIEF DESCRIPTION OF THE DRAWINGS

FIGS. 6A-6F illustrate a schematic of an implementation for transferring fluid from a Source well (e.g., well B) to a Destination well (e.g., well C) through a connecting channel and then evacuating the fluid from the Destination well where the evacuation port is separate from the pressure port. HP=high pressure; IP=intermediate pressure; LP=low pressure, VAC=partial vacuum.

FIG. 15A shows a top view of a cavity with such junctions where the sharp edges (e.g., substantially perpendicular relative to the transfer channel, e.g., a sharp corner that is not flared or rounded) of an input (transfer) channel can be seen. FIG. 15B shows a bottom view of a cavity with multiple input (transfer) channels and a single output (assay) channel. FIG. 15C shows a cross section of a channel through an input (Transfer) and output (Assay) channel. The input junctions are located in a different vertical plane than the output junction providing enhanced isolation of the junctions. For example, one or more input channels can enter at or near the outer diameter of the node and an output channel can exit at or near the center of the node, e.g., as depicted in FIGS. 15A-15B. Fluid can also be transferred out of a cavity through an entrance port such that a defined amount of fluid remains in the cavity in a region between the entrance and exit ports.

FIG. 15C shows the defined region, which has a defined volume that determines the defined amount of fluid that remains in the cavity when fluid is transferred from the cavity to the transfer channel through the entrance port. It should be noted that while the junction between the transfer channel and the cavity in FIG. 15C is referred to an "entrance port" and the junction between the cavity and the assay channel is referred to as an "exit port" in this description, fluid may be transferred into or out of the cavity in any direction. In some embodiments, the dimensions of a junction may be different than that of the main part of the channel. In some embodiments, the dimensions of the a junction are smaller than the main part of the channel. This can further reduce leakage.

Figures 15A, 15B:
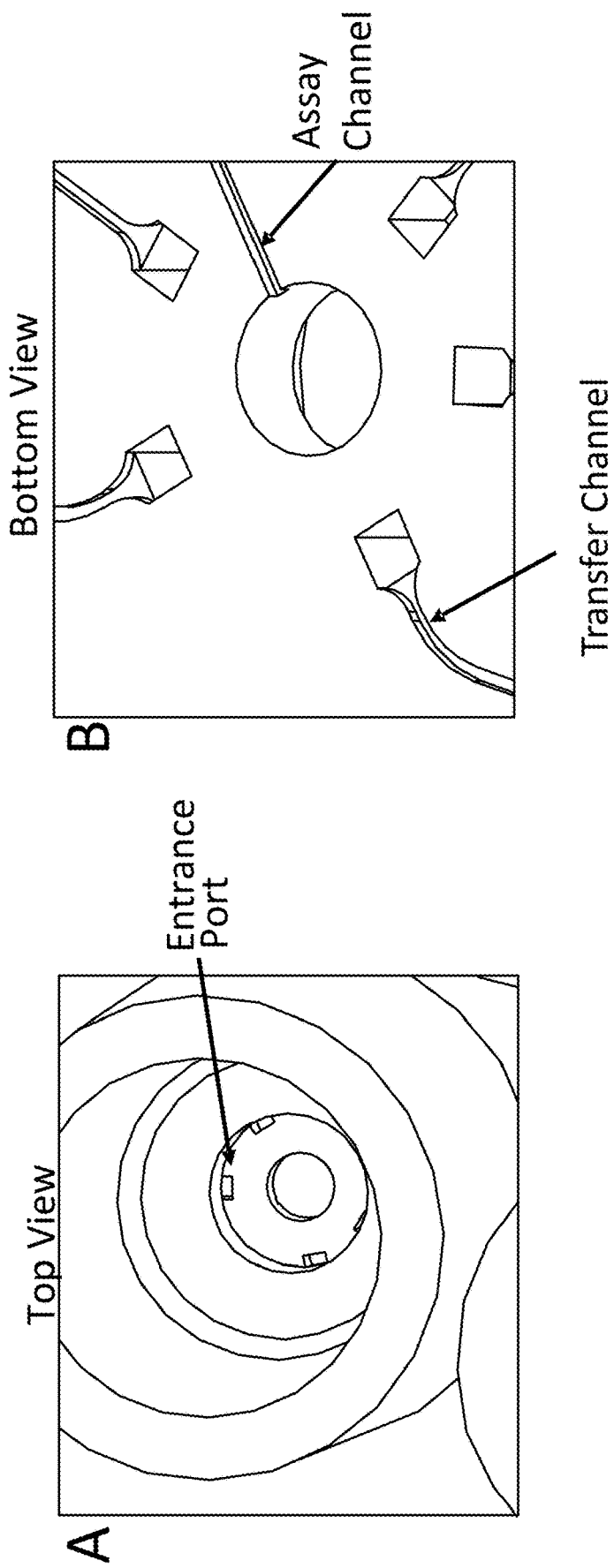
FIGS. 15A-15C illustrate a design for junctions between channels and cavities that includes multiple sharp angles for junctions of channels that transfer fluid into a cavity and a vertically isolated junction for a channel that transfers fluid out of a cavity (e.g., into an assay channel).
Figure 15C:
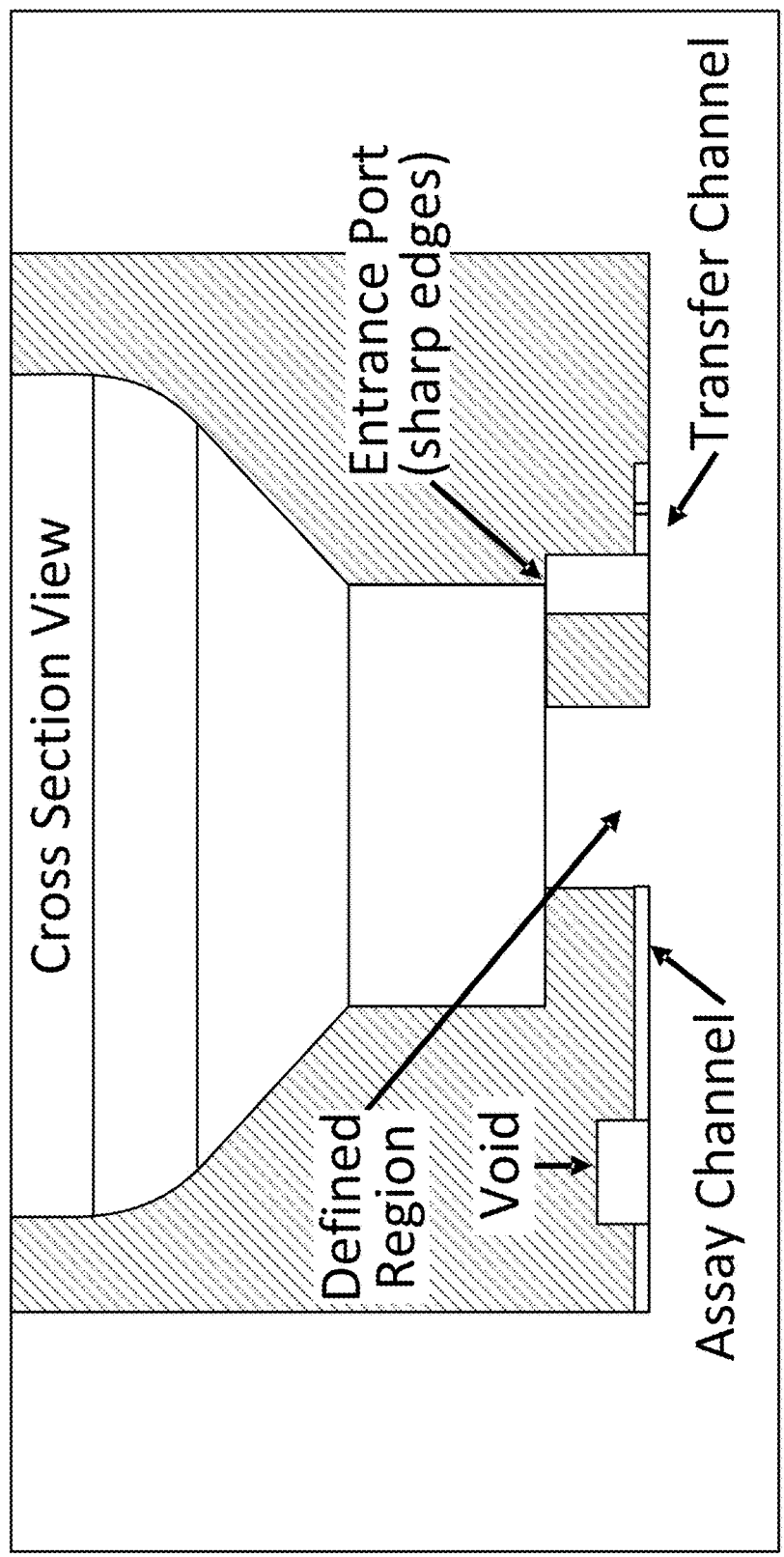

In some embodiments, a device including a defined region as shown in FIG. 15C may be used for assays that use cells or cellular structures such as spheroids, microtissues, islets, and organoids. The cells or cellular structures may be directed from the main portion of the cavity into the defined region, which is filled with a defined amount of fluid. This prevents the cells or cellular structures from being located on the sides of the main cavity region, for example, where they may be dried out when the main cavity is emptied of fluid. To direct the cells or cellular structures into the defined region, in some embodiments, a fluid may be introduced into one or more entrance ports (as shown in FIGS. 15A-C) at the top of the defined region and out of the exit port (into the assay channel of FIGS. 15A-C). This creates a fluid flow path that directs any cells or cellular structures that are in the main cavity into the defined region. The cavity volume that is above of the defined region may be described as the main region of the cavity.

In some embodiments, the entrance ports may introduce fluid into the cavity at an angle. For example, the vertical channel shown in FIG. 15C that connects the transfer channel to the cavity may be angled in a direction into the page. Fluid introduced into the cavity then can create a vortex that would "swirl" the cells or cellular structures to the center of the cavity and into the defined region.

FIGS. 16A-16B illustrate the improvement in fluid control provided by the geometrical features shown in FIG. 15A-15C. A fluid with high surfactant concentration and a fluorescent dye (fluorescein) is loaded into the wells and then after a period of 60 min the wells and channels are imaged with a fluorescence microscope (4× objective, 490 nm excitation, 530 nm emission). FIG. 16A shows results from a device with features shown in FIG. 14B. Significant passive leakage into the channels is seen with a native COC surface. The addition of surface coating that enhances the hydrophobic barrier reduces passive leakage. FIG. 16B shows results from a device with features shown in FIG. 15. No passive leakage is observed with native COC surface indicating a higher barrier to fluid movement.

Figures 17A, 17B:
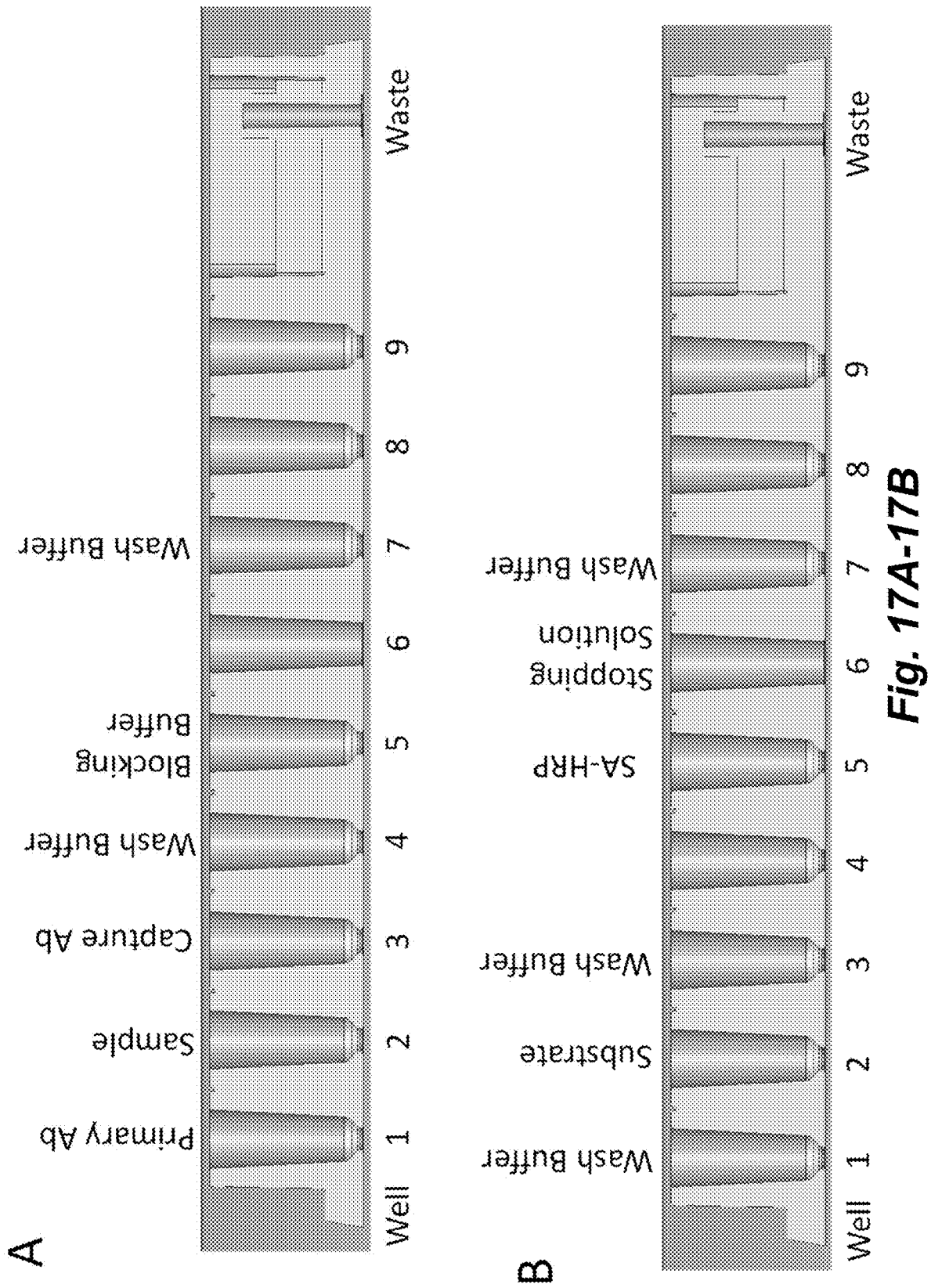

FIGS. 17A-17B illustrates the reagent loading configuration for performing a flowchip ELISA. The assay protocol is divided into a $1^{st}$ Half (FIG. 17A) and a $2^{nd}$ Half (FIG. 17B). Reagent locations are indicated on cross-sectional views of the flowchip shown in FIG. 1A. Well numbers are indicated below the flowchips.

Figure 18:
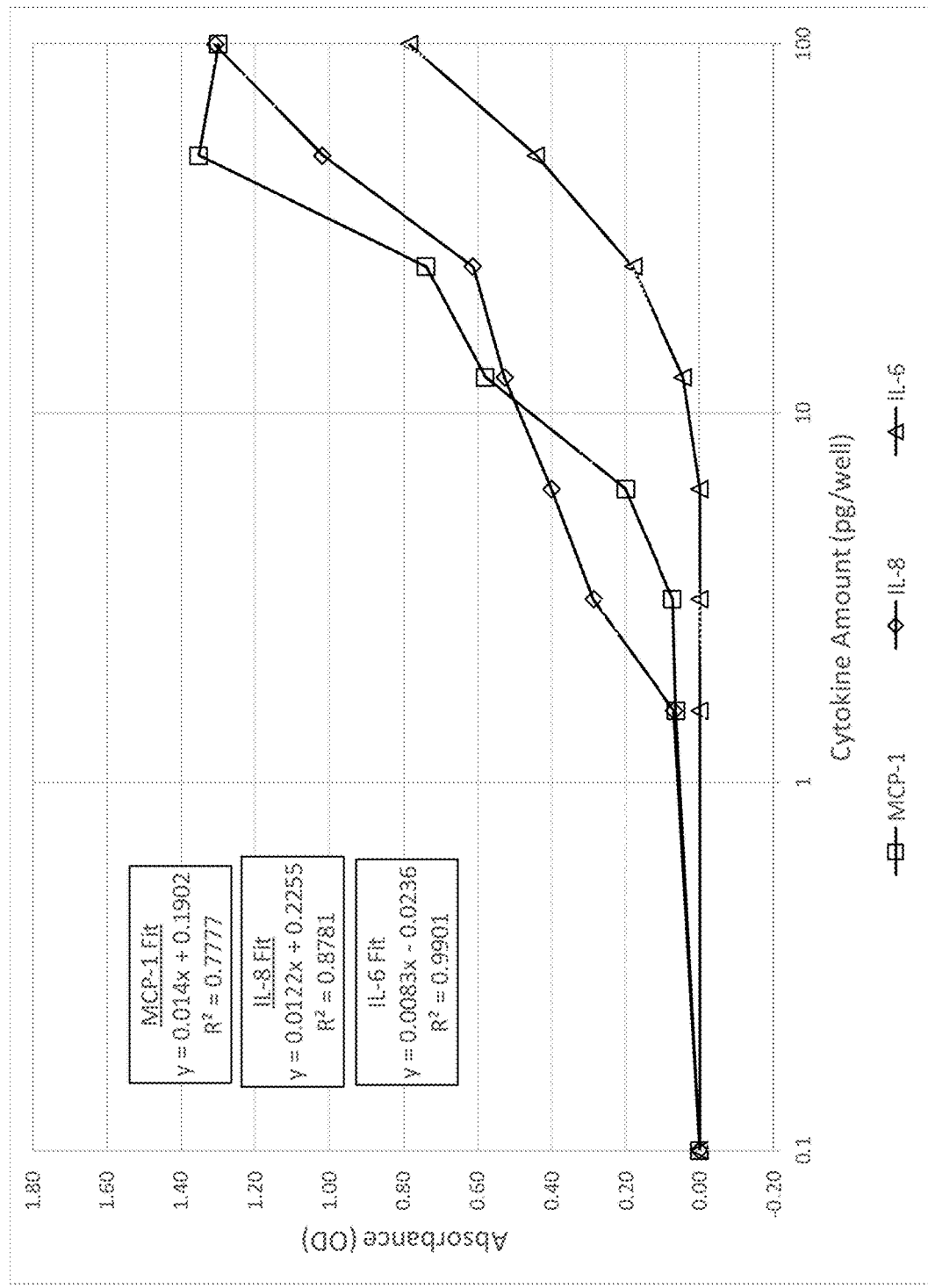

FIG. 18 shows the Standard Response Curves for MCP-1, IL-8, and IL-6 generated from the flowchip ELISA system. The linear fit parameters shown in the figure were used to quantify the amount of the cytokines present in cell supernatants for the multiparametric inflammation assay.

Figure 19:
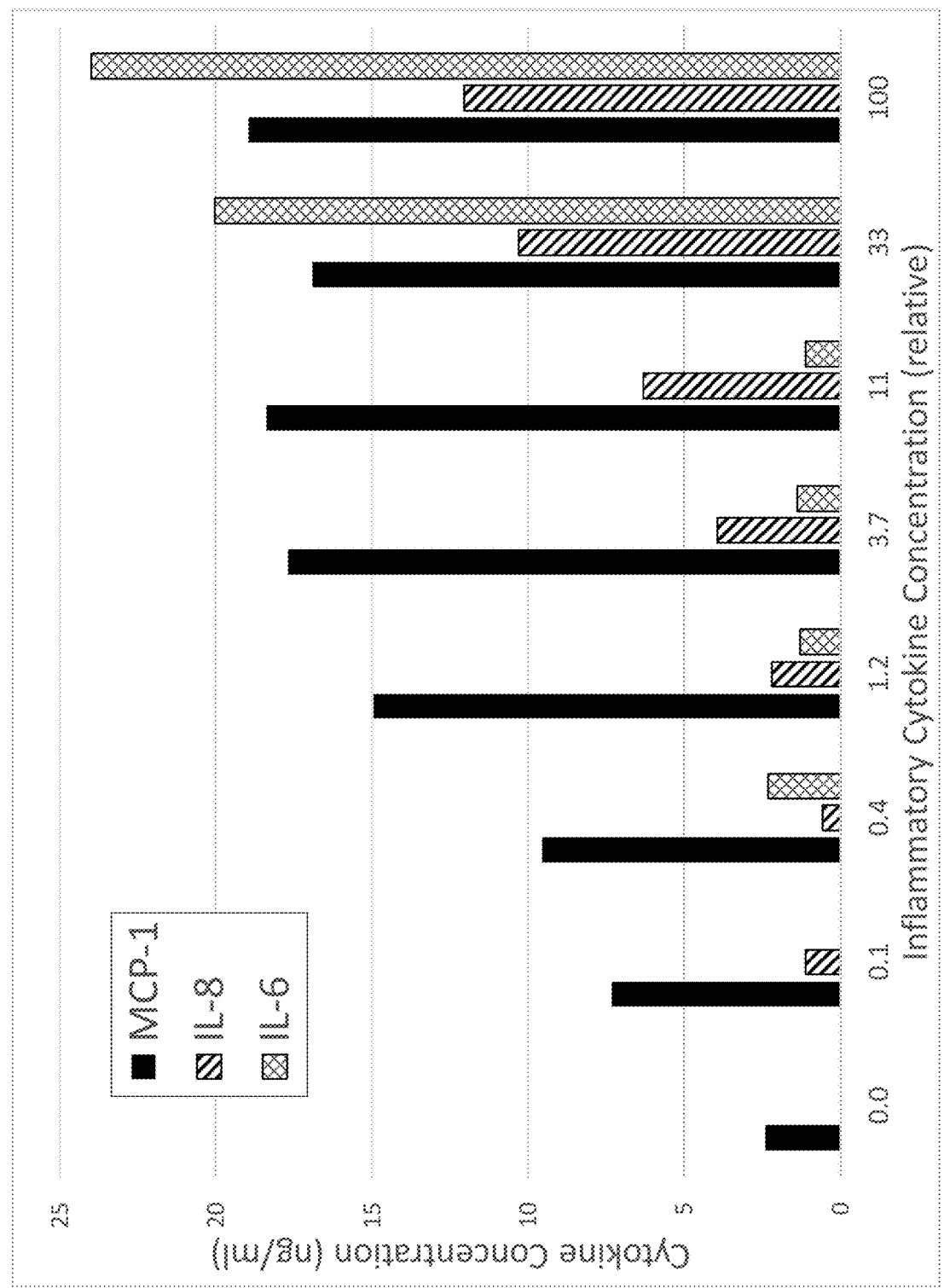

FIG. 19 shows the upregulation of MCP-1, IL-8, and IL-6 in HUVECs by an inflammatory cytokine mixture of TNF-α, IL-1β, and IFN-γ after about 20 hours at 37° C. The maximum concentrations of the compounds (relative value=100) were about 5 ng/well, about 1 ng/well, and about 100 ng/well respectively.

FIGS. 20A-20D shows the concentration dependent effect of anti-inflammatory compounds SB202190, MG-132, and AG-126 on HUVECs stimulated with an inflammatory cytokine mixture of TNF-α, IL-1β, and IFN-γ for 20 hours at 37° C. HUVEC inflammation response as shown by upregulation of IL-8 (FIG. 19A), IL-6 (FIG. 19B), and MCP-1 (FIG. 19C) was clearly diminished by all three compounds. Each curve was fit with a 4-Parameter function and the corresponding $EC_{50}$ values are shown in FIG. 19D.

Figure 21A:
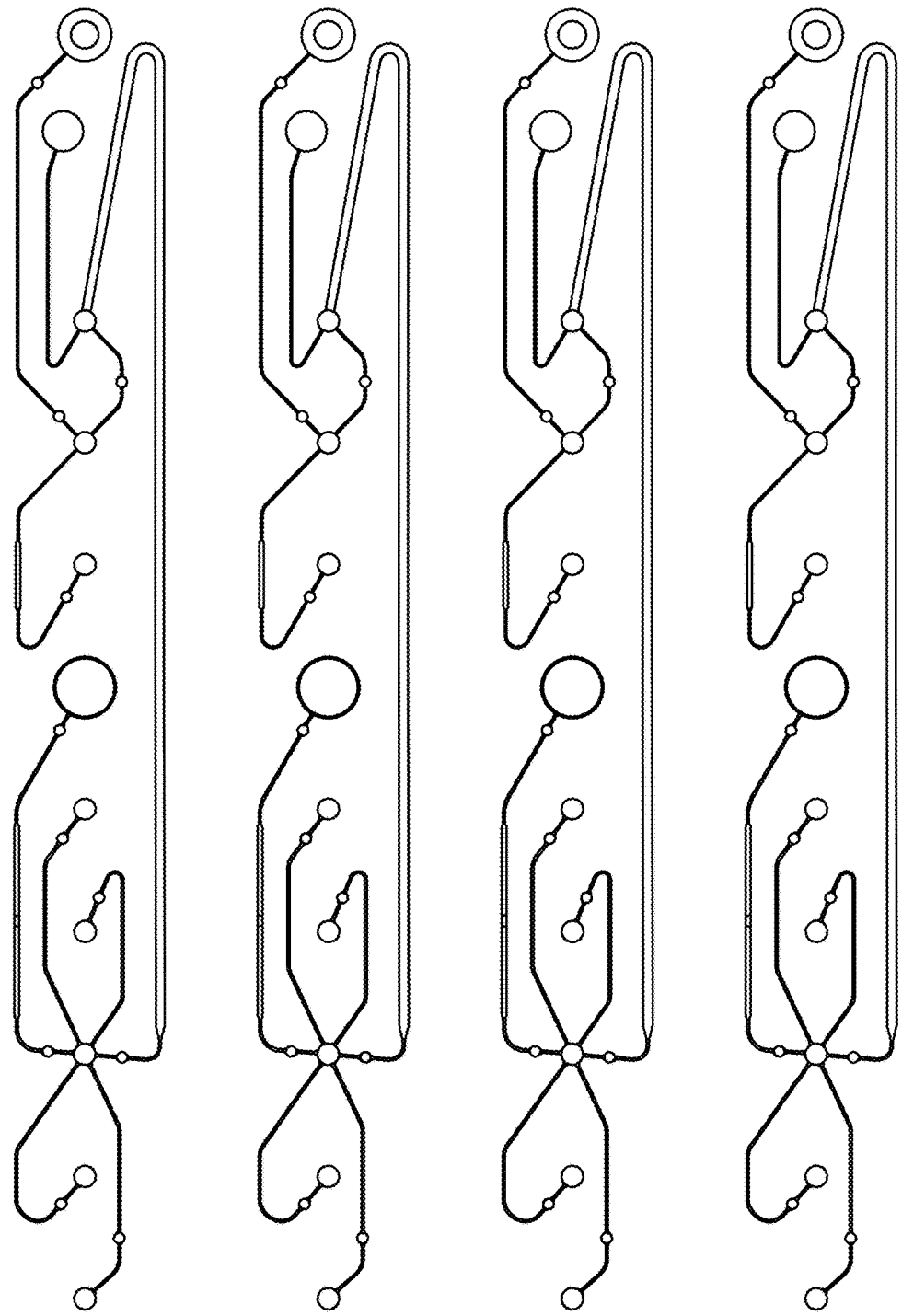
Figure 21B:
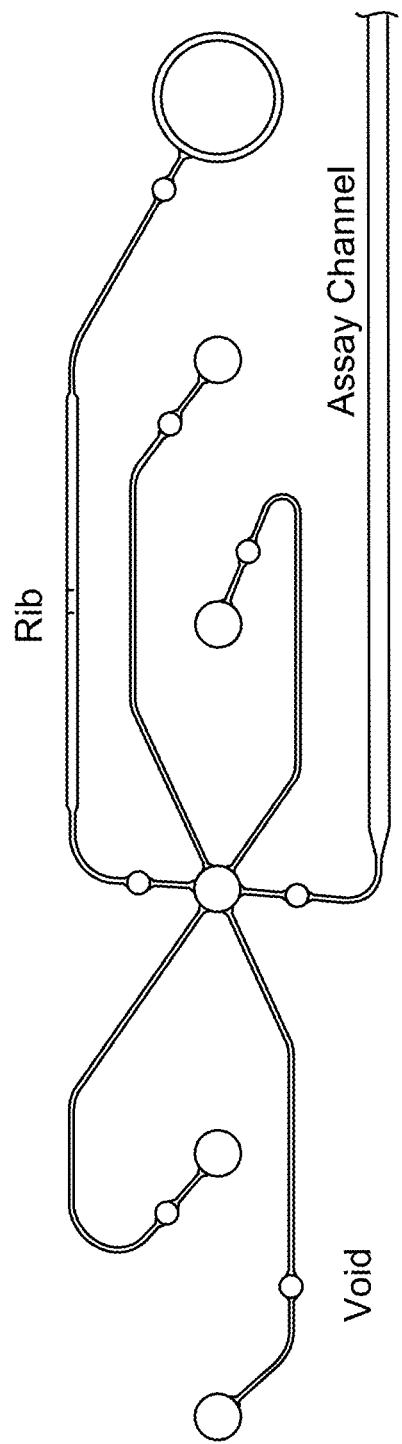

FIGS. 21A-21B illustrate a second example flowchip with improved fluid control features. A. An example flowchip depicting 4 microfluidic networks. B. A zoomed region of one microfluidic network showing the location of fluid flow barrier structure (voids and ribs) that were added to improve fluid control.

Figure 22:
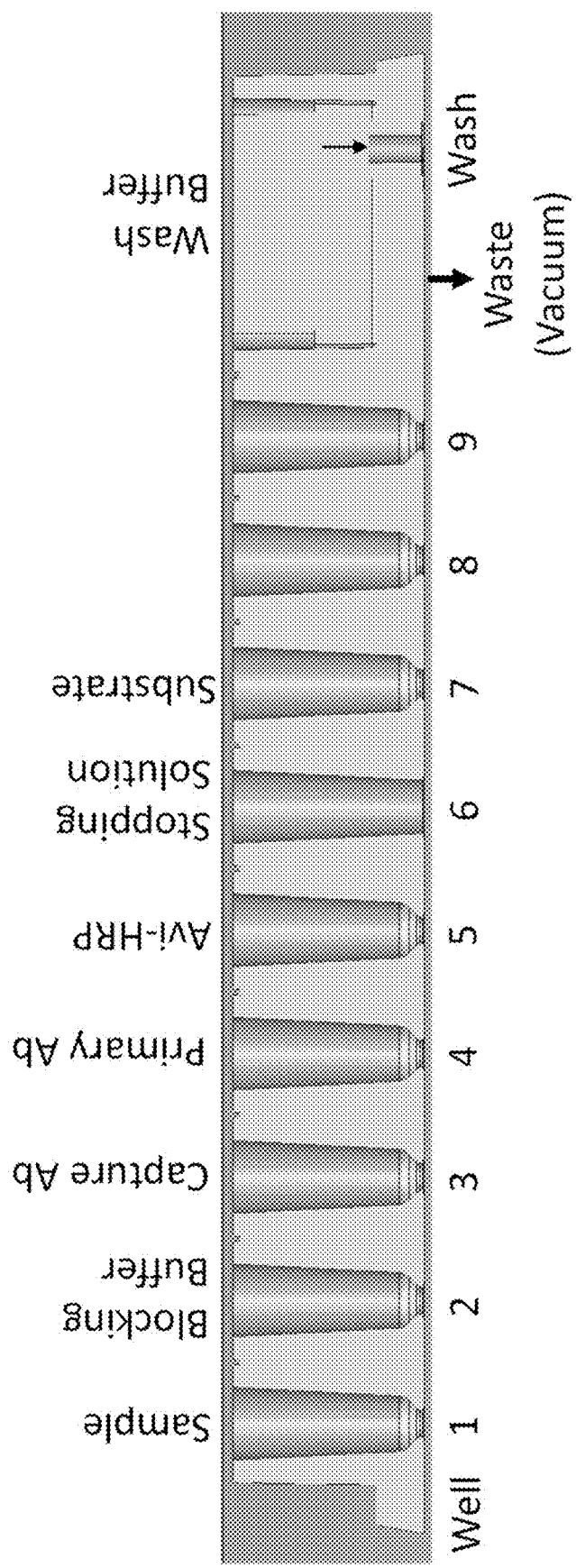

FIG. 22 illustrates the reagent loading configuration for performing a flowchip ELISA in the improved flowchip shown in FIG. 21. The assay protocol is performed with a single reagent loading step. Reagent locations are indicated on cross-sectional views of the flowchip. Well numbers are indicated below the flowchips.

Figure 23A:
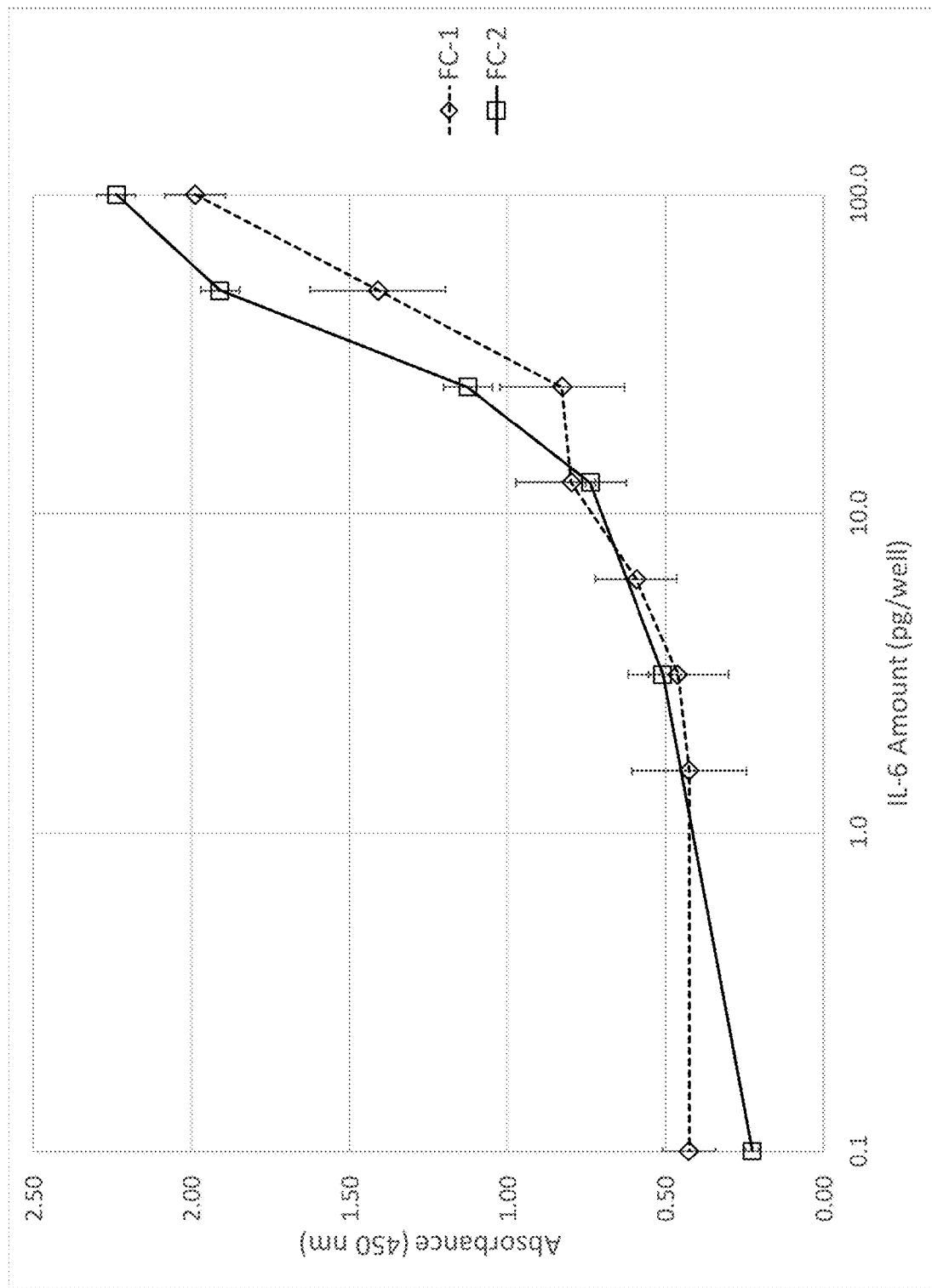

FIGS. 23A-23B illustrate the improvement in assay performance realized by the flowchip device shown in FIG. 21. FIG. 23A shows standard response curves for an IL-6 ELISA from the device shown in FIG. 1 (FC-1) and device shown in FIG. 21 (FC-2) with improved fluid control. Assay performance metrics are given in FIG. 23B showing significant assay improvement using a device with enhanced fluid control features.

Figure 24A:
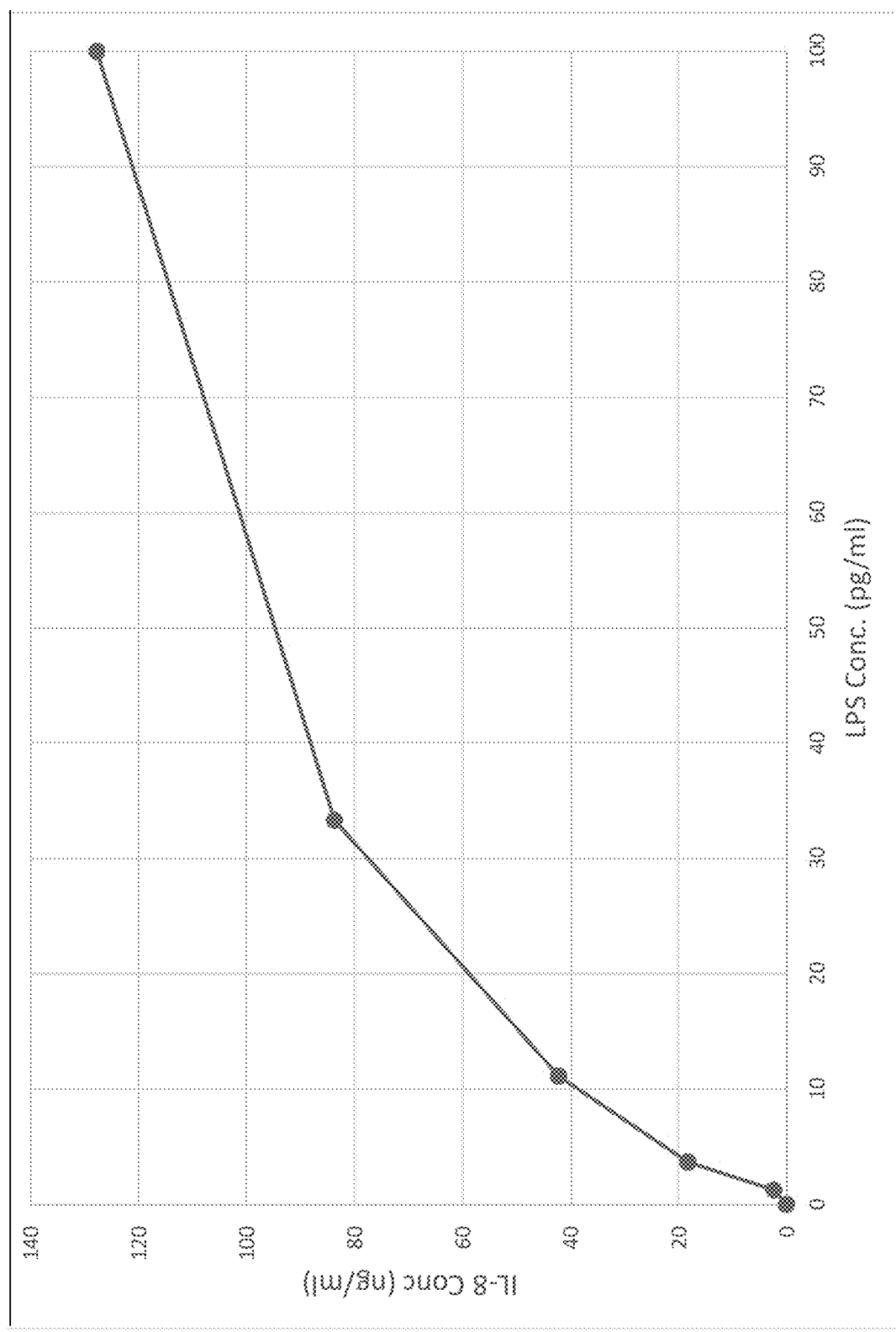
Figure 24B:
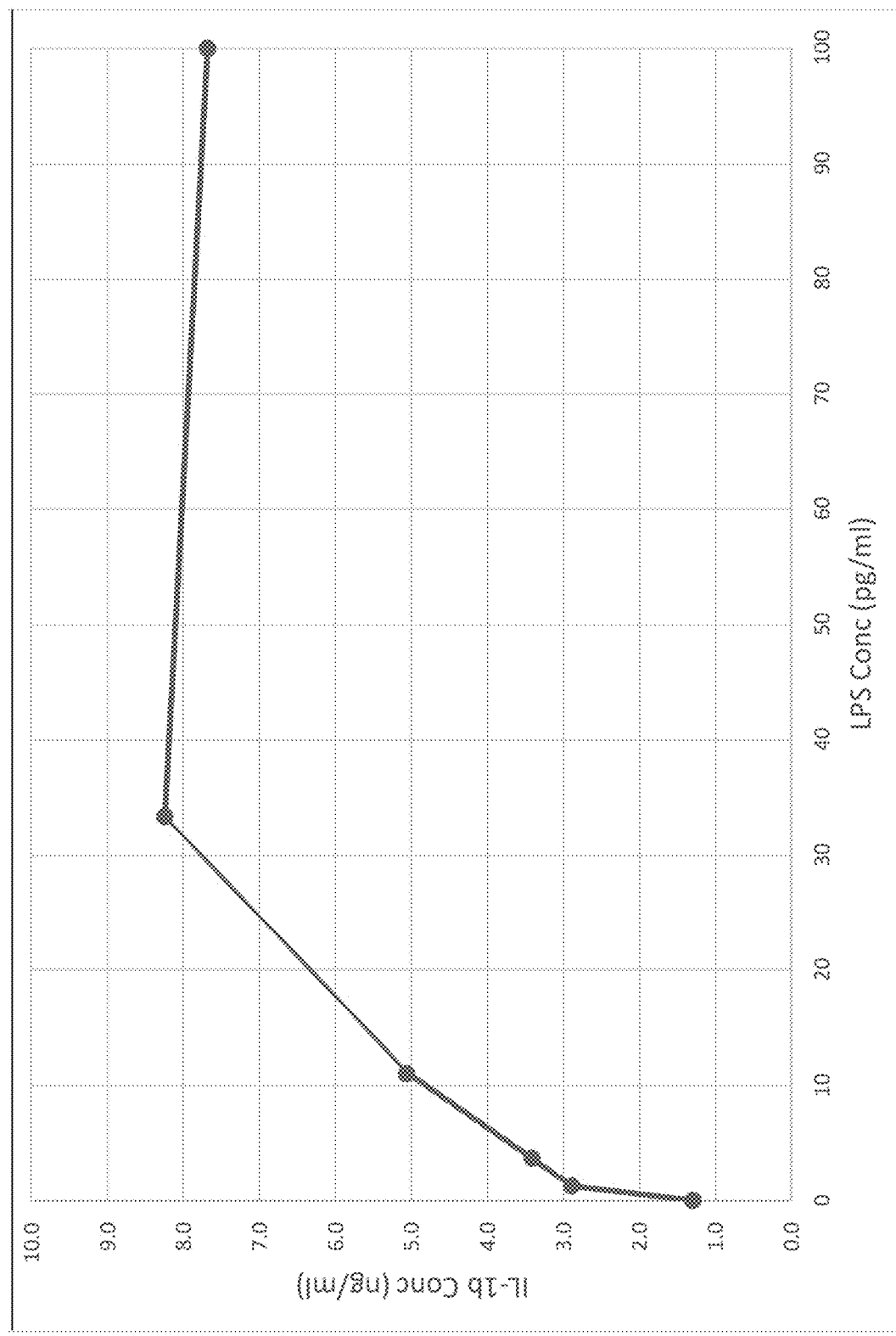

FIGS. 24A-24B show the upregulation of IL-8 (FIG. 24A) and IL-1b (FIG. 24B) in THP-1 cells after stimulation with different concentrations of LPS after about 20 hours at 37° C.

Figure 25A:
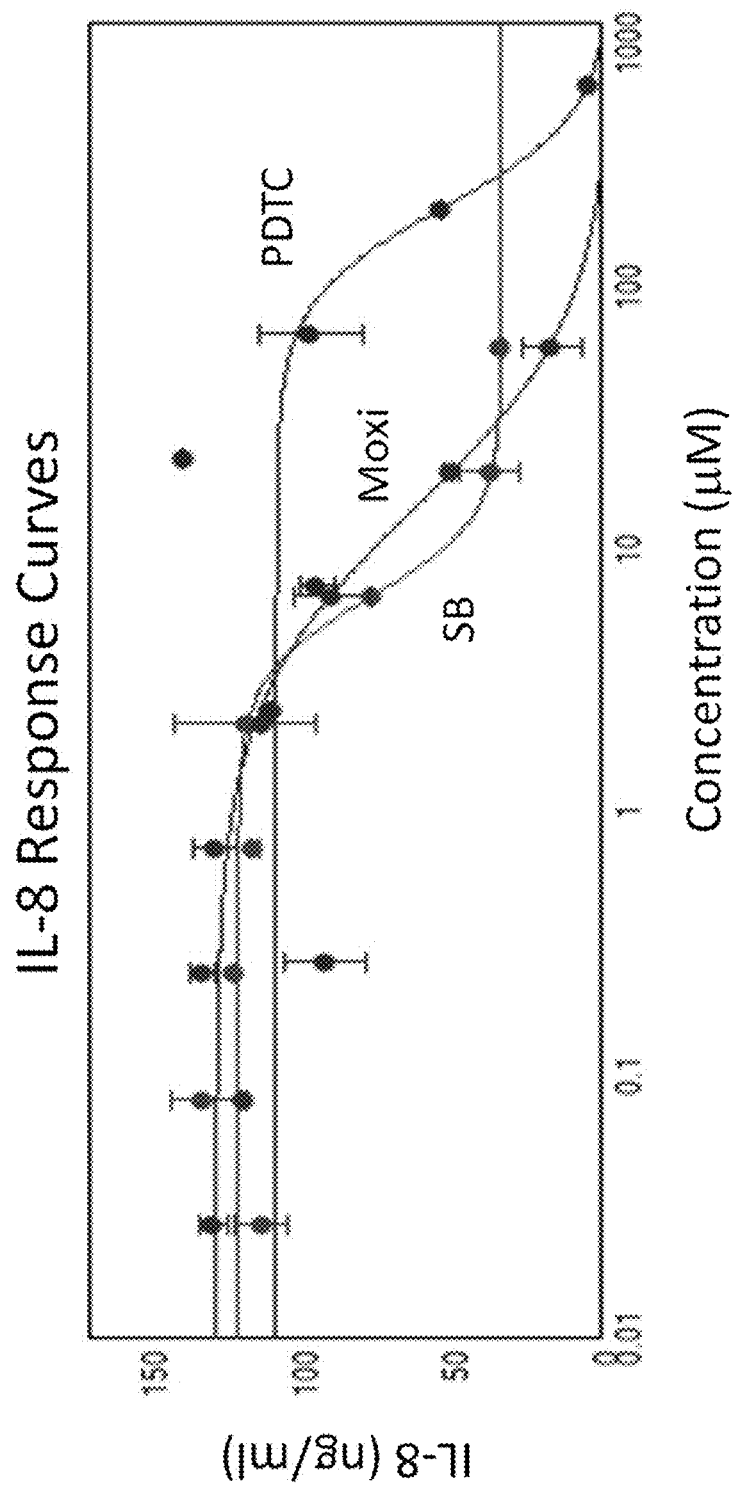

FIGS. 25A-25B show the concentration dependent effect of anti-inflammatory compounds SB202190, Moxifoxacin, and PDTC on THP-1 cells stimulated with PMA and LPS for 20 hours at 37° C. THP-1 cellular inflammation response as shown by upregulation of IL-8 (FIG. 25A) was clearly diminished by all three compounds. Each curve was fit with a 4-Parameter function and the corresponding $EC_{50}$ values are shown in FIG. 25B.

DETAILED DESCRIPTION

1. Introduction

The flowchips, systems and methods described herein address the challenges presented by the currently available reconfigurable microfluidic systems in that the high gas pressure needs to exert enough force to overcome the initial hydrostatic and hydrophobic barriers to move fluid through the channel, but insufficient force to force air through the destination well once the channel empties. The flowchips, systems and methods are based, in part, on the discovery and utilization of a narrow process window to achieve this balance, which can be adjusted by adjusting parameters, such as channel dimensions, flowchip material, and fluid composition. The present flowchips and systems are suitable for running multi-step assays (e.g., such as ELISAs), which can require flowchips with multiple channels of varying cross-sectional areas and lengths, and involve reagents with different physical characteristics (e.g., buffers, substrates, stopping solutions, blocking agents, etc).

Herein we describe methods for control of fluid movement in valveless microfluidic flowchips that use high, intermediate, low and vacuum pressure settings and surface tension induced fluid resistance at the well/channel interface (WCI) to improve robustness. Additionally, we provide a system and method for removing fluid from a flowchip using partial vacuum. Further, we provide flowchips with channels having structural fluid flow barrier structures or configurations that increase the hydrophobic and hydrostatic barriers without substantially compromising overall fluid flow.

2. Valveless Microfluidic Flowchips

Provided are valveless (e.g., capillary force driven) microfluidic flowchips. In some embodiments, the flowchips comprise one or more networks of microfluidic cavities connected by microfluidic channels, wherein reservoirs are cavities that are connected to only one channel each, and nodes are cavities that are connected to two or more channels each; wherein: i) a first plurality of the channels connect only two cavities each; ii) a second plurality of the channels comprise a fluid flow barrier structure or configuration; and iii) a plurality of the cavities include a gas pressure port. In some embodiments, the first and second pluralities of the channels can be the same, different, or partially the same (e.g., overlapping). A "fluid flow barrier structure or configuration" refers to a structural feature of a microfluidic channel having increased fluid flow resistance. The pressure required to push fluid through a channel from a source well to a destination well is referred to as the "breakthrough pressure". Often, the structural feature is a highly non-linear deviation from a straight path between adjacent cavities, a narrowing or constriction in the channel (whether straight or otherwise), a void (e.g., a sealed cavity) in the channel that introduces an abrupt and substantial change in geometry, including an increase in channel dimensions (height and width), and/or a variation in the channel's surface condition (e.g., a roughening). Increased fluid flow resistance can be due to one or more forces resisting flow, including without limitation, resistive forces resulting from static friction, surface energy, surface tension, fluid density, and/or fluid viscosity.

The presently described flowchips are improved over valveless microfluidic flowchips described in the art, e.g., U.S. Patent Publication Nos. US2017/0021351, US2017/0021352 and US2017/0021353 (issued as U.S. Pat. No. 9,733,239), hereby incorporated herein by reference in their entireties for all purposes, in that a plurality of the channels in the present flowchips comprise a fluid flow barrier structure or configuration allowing for more precise control of fluid flow and their use with intermediate positive pressures avoid introduction of air bubbles or air gaps into the channels.

The fluid flow barrier structure or configuration can be located anywhere along the length of a microfluidic channel. In some embodiments, a fluid flow barrier structure or configuration is located at or near an interface of the cavity with the channel. In some embodiments, a fluid flow barrier structure or configuration is located essentially at the interface of a cavity and a microfluidic channel, e.g., at a distance in the range of from about 0 mm to about 5 mm, 6 mm, 7 mm, 8 mm, 9 mm or 10 mm from a cavity. As appropriate, a microfluidic channel can have one, two or more fluid flow barrier structures or configurations. In a microfluidic channel having two or more fluid flow barrier structures or configurations, the fluid flow barrier structures or configurations can be the same or different. The fluid flow barrier structure or configuration can also incorporate an enhanced hydrophobic barrier.

Figures 7A, 7B, 7C:
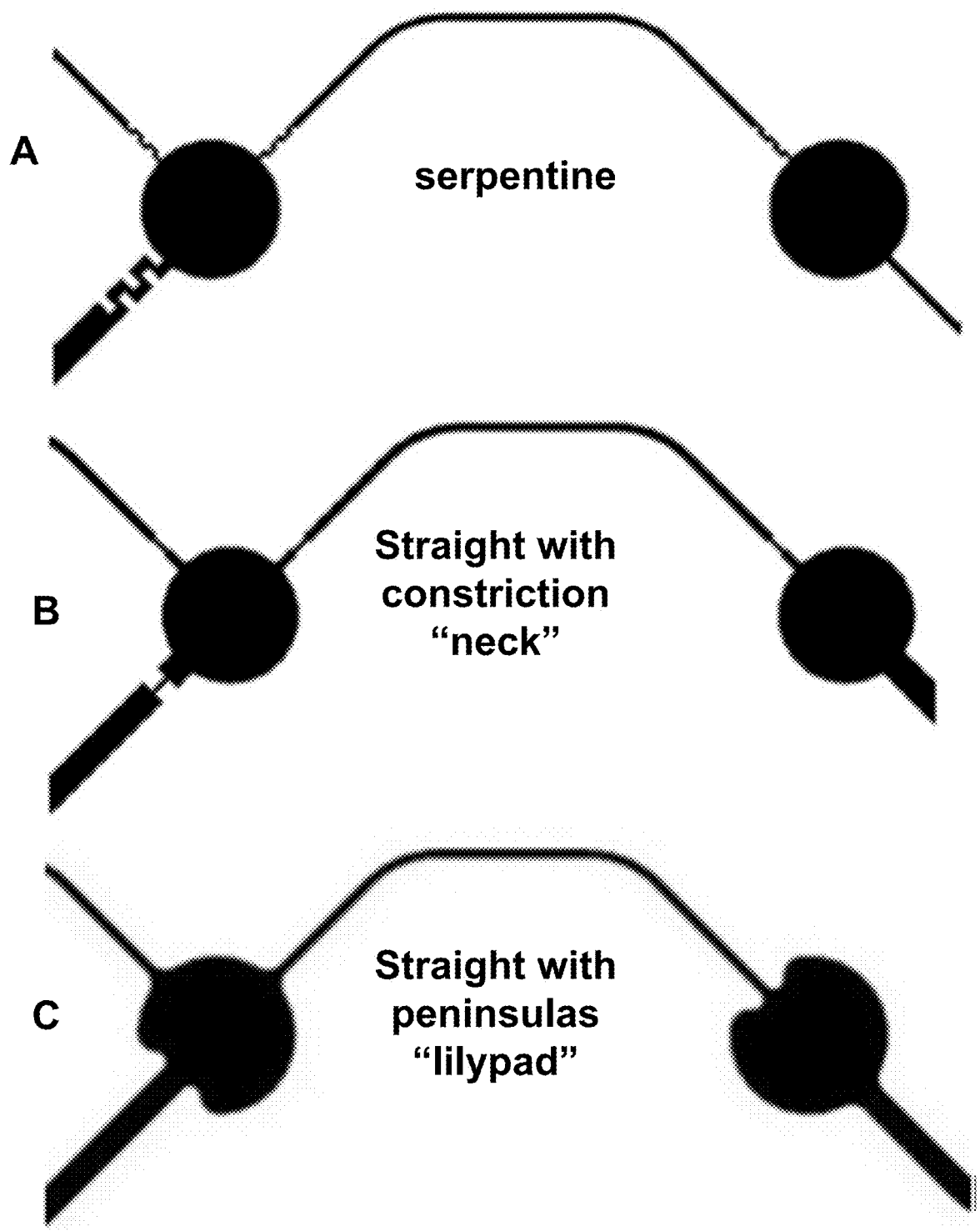
FIGS. 7A-7C illustrate different fluid flow barrier structures or configurations.
Figures 9A, 9B:
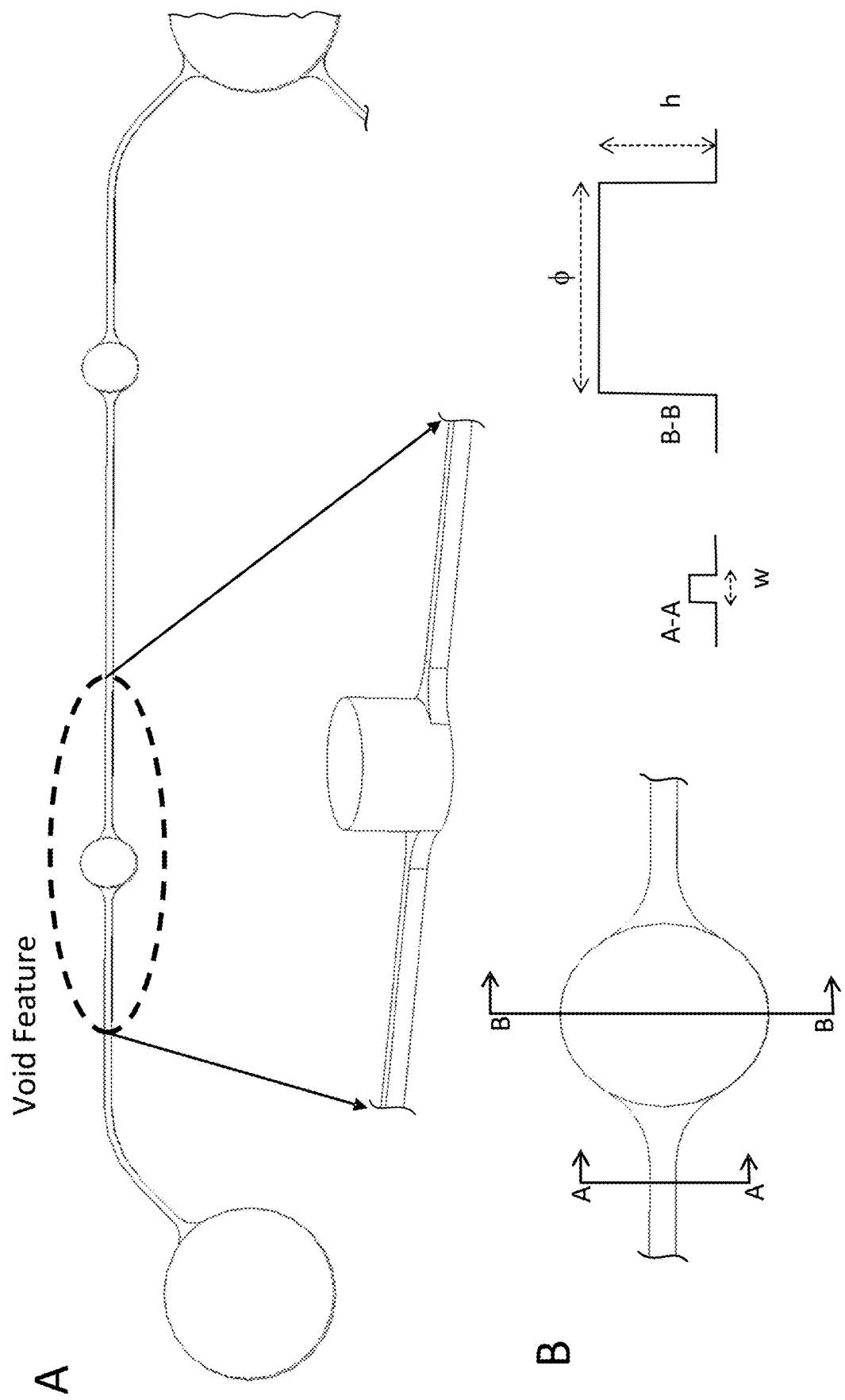
FIGS. 9A-9B illustrates a void feature (e.g., fluid flow barrier structure or configuration) that is used to increase hydrophobic barrier and hydrostatic resistance in channels. The Void diameters ($\phi$)) for an about 50 μm wide (w) channel range from about 100 to about 1500 μm. The Void heights (h) for an about 50 μm high channel range from about 50 to about 500 μm. The optimum diameter and height ranges are dependent on the input channel geometry. The Void cross sections can be circular or elliptical. The Void walls can be perpendicular to the channels or have slight angles (e.g., about 0 to about 20 degrees) to facilitate fabrication.

In some embodiments, the fluid flow barrier structure or configuration increases channel resistance to fluid flow or the pressure required to move fluid by at least about 20%, e.g., at least about 25%, 30%, 35%, 40%, 45%, 50%, or more, e.g., in comparison to a channel that does not have a fluid flow barrier structure or configuration (e.g., a straight, unconstricted channel). A fluid flow barrier structure or configuration can be any structural configuration of a microfluidic channel that increases the resistance of fluid flow, e.g., in comparison to a linear or substantially linear and substantially unconstricted microfluidic channel without the fluid flow barrier structure or configuration, e.g., in comparison to a linear microfluidic channel having constant and full width and height dimensions. In some embodiments, the fluid flow barrier structure or configuration comprises a constriction or narrowing of the channel, a rib feature, and/or a channel having a markedly non-linear path. In some embodiments, the non-linearity is characterized by an abrupt change in the direction of a channel, e.g., which can be from 45 degrees to 135 degrees, e.g., over a length of 1 to 5 channel widths. The number of changes, or turns in direction, can be from 1 to 10 or more in sequence. A fluid flow barrier structure or configuration that is a constriction or narrowing of the channel is illustrated in FIG. 7B; a rib feature is illustrated in FIG. 11. In some embodiments, the fluid flow barrier structure or configuration comprises a geometry selected from the group consisting of serpentine or S-curve geometry, a junction, a fishbone or a split channel. A serpentine or S-curve fluid flow barrier structure or configuration is illustrated in FIG. 7A. In some embodiments, the fluid flow barrier structure or configuration comprises a void (e.g., a sealed cavity) located in-line with the channel. A void fluid flow barrier structure or configuration introduces an abrupt and substantial change in geometry, including increases in height and width dimensions, as illustrated in FIGS. 9A-9B. In some embodiments, one or more or a plurality of the cavities are not cylindrical and comprise a concave curvature at the junction of the cavity with one or more channels, such that the cavity forms peninsulas that extend from the cavity towards one or more channels (e.g., the cavity is in the shape of a lilypad). See, e.g., FIG. 7C. In some embodiments, a sealed cavity or void is incorporated into a channel, e.g., as depicted in FIGS. 9A-9B. In some embodiments, a region of reduced height (e.g., a rib feature) is incorporated into a channel, e.g., as depicted in FIG. 11. In some embodiments, a channel can have multiple fluid flow barrier structures or configurations, e.g., 2, 3, 4 or more fluid flow barriers.

Figures 14A, 14B:
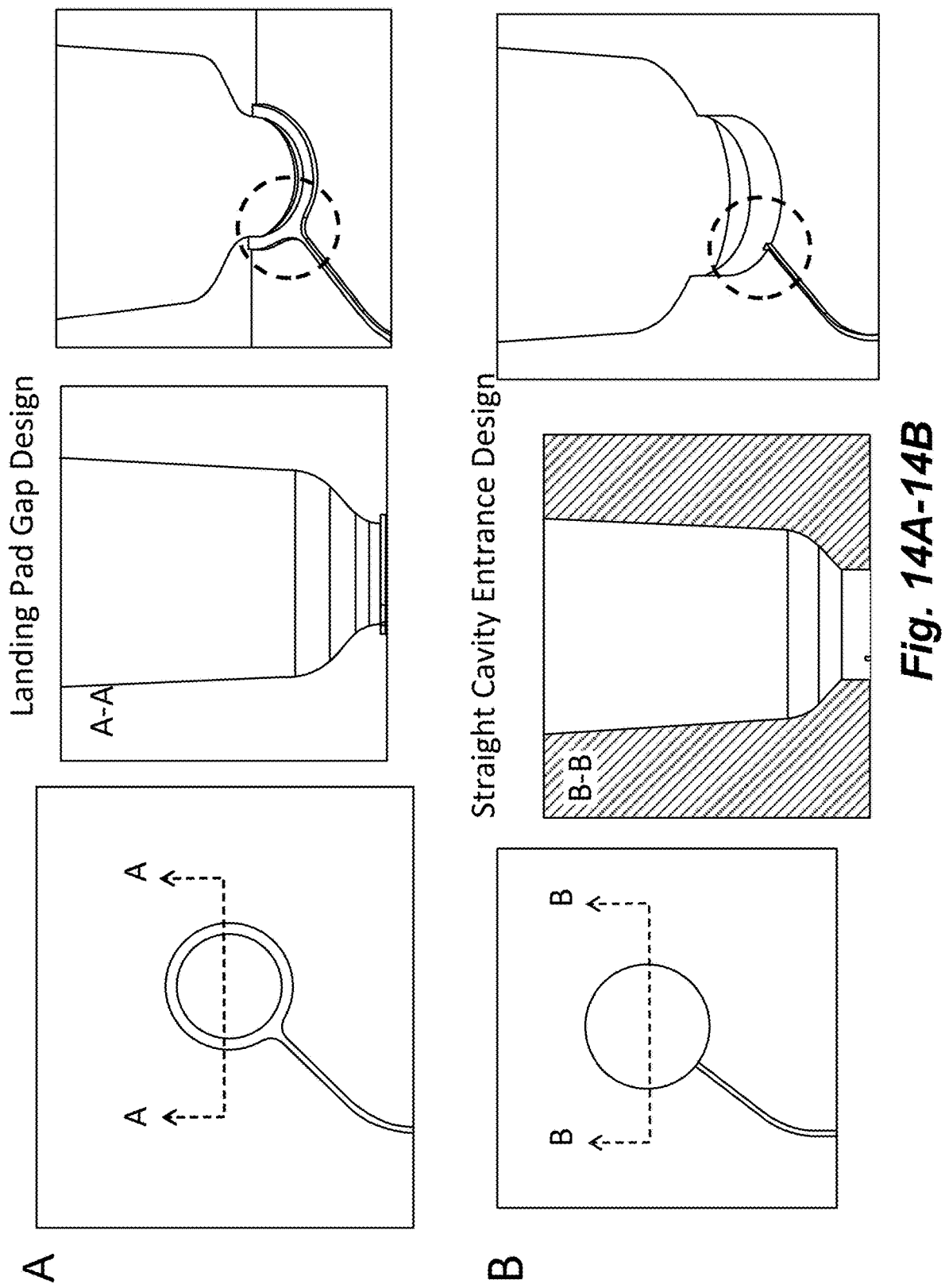
FIGS. 14A-14B illustrate two designs for junctions between channels and cavities. Depicted are the molds around which a cavity-channel junction is formed. A. A "Landing Pad" gap exists between the channel and cavity causing a more gradual change of geometry between the channel and cavity and providing a microcapillary connection to other channel junctions. In this version, when the pin is removed, the "landing pad" mold leaves a "lip" where the bottom surface diameter is wider than the walls of the cavity. Further, the channel is flared at the junction with the cavity. B. No gap exists in the plane of the channel and the channel enters straight into the cavity. In this version, the mold does not leave any lip, and the bottom surface diameter is equal to the walls of the cavity. Moreover, there is a sharp change in geometry between the channel and cavity, because the junction of the channel with the cavity is perpendicular. No microcapillary connection exists to other channel junctions.

In some embodiments, one or more or a plurality of the cavities include a straight and perpendicular entrance of one or more channels into the cavity, such that there is a sharp change in geometry (e.g., 90° where the channel enters the cavity, e.g., as depicted in FIGS. 14A-14B. Perpendicular includes the intersection of a straight channel region with a small segment of a curved surface, as shown in FIGS. 14A-14B. In some embodiments, the nodes are configured such that entrance (input, transfer) channel and exit (output, assay) channel junctions are located in different vertical planes, e.g., as depicted in FIGS. 15A-15B. For example, the input (transfer) channels can enter at one or more entrance points of the space above the node and the output (assay) channels can exit at one or more exit points at the bottom of the node. The input channels are located at or near the outer diameter of the cavity (e.g., within about 1 mm of the outer edge of a 3 mm diameter cavity, e.g., within the outer ⅓ of the diameter of the cavity) while the output channel is located at or near the center of the cavity (e.g., within about 1 mm of the center, e.g., within the inner ⅓ of the diameter of the cavity). In some embodiments, a defined amount of fluid remains in the source cavity in a region between the entrance and exit channels.

Similar to the microfluidic systems described in U.S. Patent Publication Nos. US2017/0021351, US2017/0021352 and US2017/0021353 (issued as U.S. Pat. No. 9,733,239), the valveless microfluidic flowchips described herein are based on networks of microfluidic cavities connected by microfluidic channels, which can be hydrophobic. Each cavity can be classified as either a reservoir or a node, and includes a pressure port via which gas pressure may be applied. Sequences of gas pressures, applied to reservoirs and nodes according to fluid transfer rules, enable fluid to be moved from any reservoir to any other reservoir in a system.

The valveless microfluidic flowchips can be designed from the basic components of reservoirs, nodes and channels to perform many different microfluidic tasks including, e.g., homogenous and inhomogeneous assays and microwell plate interfacing. The systems are scalable to any number of fluid inputs and outputs, and they can be used to manipulate very small fluid volumes necessary for multiplexing samples with analytes to perform multiple simultaneous assays.

A microfluidic cavity is an internal volume for accumulating fluid in the microfluidic flowchips. A reservoir is a microfluidic cavity that is connected to only one microfluidic channel. A node is a microfluidic cavity that is connected to more than one microfluidic channel. Finally, a channel is a microfluidic passageway between nodes or reservoirs. Each channel in the present valveless microfluidic system connects at least two cavities. Contemplated are flowchip designs where there are channel intersections and fluid flow is controlled by differential resistance in different channels.

Nodes are designed to present lower resistance to fluid flow than are channels. The fluid flow resistance of a cavity or channel is inversely proportional to the square of its cross sectional area. Therefore the difference in flow resistance between a channel and a reservoir, or between a channel and a node, may be engineered via different cross sectional areas.

Reservoirs store fluids; e.g., samples or reagents. Nodes, on the other hand, can store a fluid initially and also can store other fluids during a sequence of fluid transfer steps. Provisions for automated loading fluid into, or unloading fluid from, a reservoir may be provided, with a small plastic tube extending from a reservoir to a glass bottle or with an automated pipette station being examples.

The valveless microfluidic flowchips can be implemented in a variety of ways as long as: reservoirs, nodes, channels and pressure ports are provided; and resistance to fluid flow is greater in the channels than in the nodes. In some embodiments, the channels are hydrophobic, e.g., to prevent fluid flow when pressures at the two ends of a channel are equal or nearly so. In the present flowchips, fluid flow through microfluidic channels is controlled by gas pressure differences applied to the cavities, e.g., reservoirs and nodes. Fluid flow through a hydrophobic channel exhibits a pronounced threshold effect. At first, no fluid flows as the pressure difference from one end of the channel to the other is increased. However, once a threshold pressure difference is reached, fluid flow rate through the channel increases in proportion to applied pressure difference. The hydrophobicity of channels sets the threshold pressure difference, and the difference between high and low pressures used in a system is designed to be greater than the hydrophobic threshold pressure. When the pressure is high at the source cavity end of a channel and low at the destination cavity end, fluid flows in the channel from the source cavity to the destination cavity. Intermediate gas pressure is insufficient to overcome the hydrophobic threshold, but if fluid is already flowing (e.g., by subjecting the source cavity to high gas pressure), intermediate gas pressure is sufficient to continue allowing the fluid flow, albeit at a reduced rate. If fluid is already flowing and the pressure is reduced to intermediate gas pressure at the source cavity end of a channel and remains low at the destination end of the channel, fluid continues flowing in the channel from the source cavity to the destination cavity, but air is not introduced into the channel.

The hydrophobic threshold pressure of hydrophobic channels keeps fluid in nodes and reservoirs from leaking into the channels when no pressure differences are applied. The threshold pressure is designed to be great enough to prevent fluid flow that might be driven by the hydrodynamic pressure caused by the weight of fluid in a reservoir or node, or by residual pressure differences that might exist when applied pressures are switched between high and low. Thus a "hydrophobic channel" is defined as one that exhibits a pressure threshold that prevents fluid from leaking into the channel when the pressure difference between the two ends of the channel is less than a designated or threshold pressure. In an example valveless microfluidic system, channels were designed to have about 1 kPa hydrophobic threshold pressure.

Figure 2:
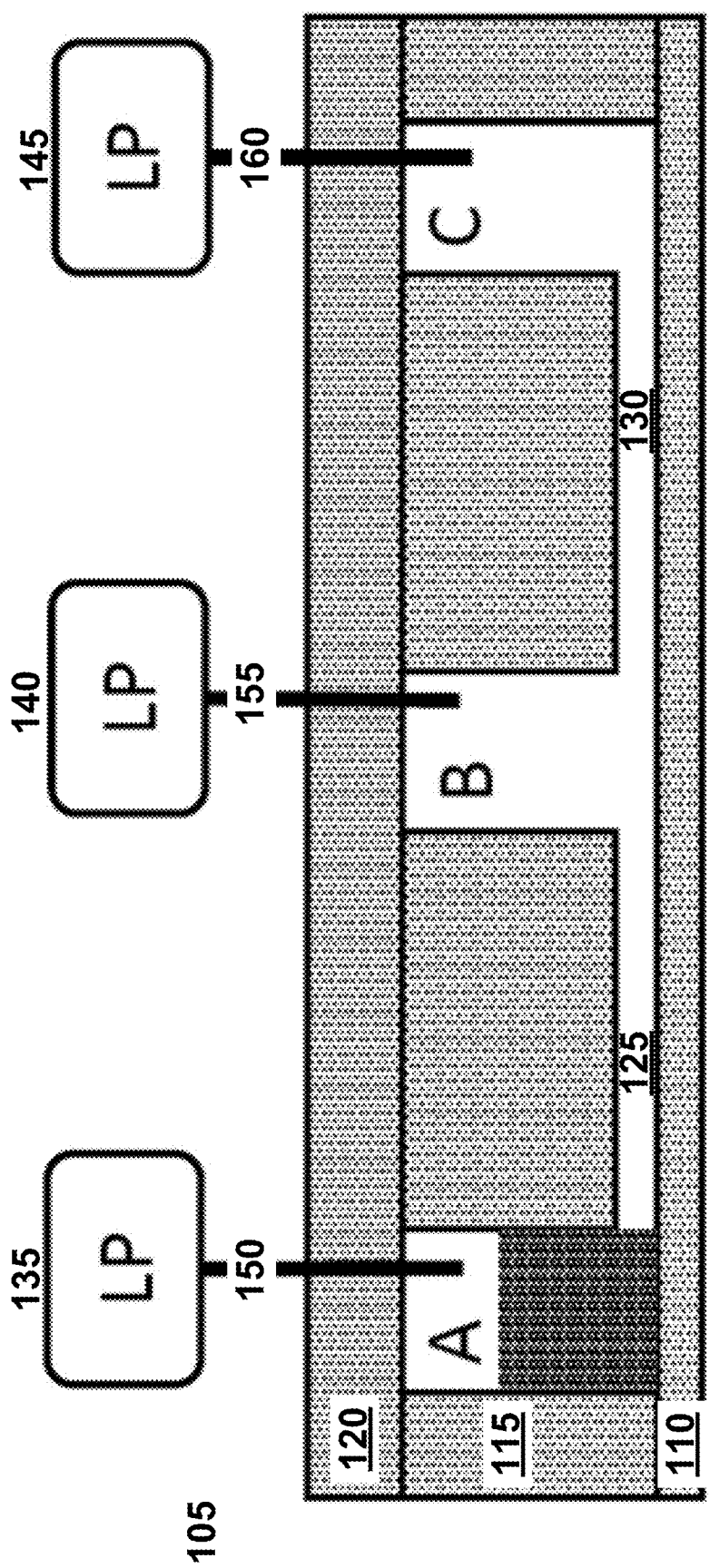
FIG. 2 illustrates a valveless microfluidic flowchip, seen in cross section. The fluid state depicted in this cross-sectional view is identical to FIG. 3A.

One implementation of a valveless microfluidic flowchip includes a substrate layer, a hydrophobic fluid layer, and a pneumatic layer. FIG. 2 illustrates a valveless microfluidic flowchip, seen in cross section. In FIG. 2, microfluidic flowchip 105 includes a substrate layer 110, a hydrophobic fluidic layer 115, and a pneumatic layer 120. Cavities in the hydrophobic fluidic layer are labeled A, B and C in FIG. 2 and in FIGS. 3A-3F. Cavities A and B are connected by channel 125 while cavities B and C are connected by channel 130. Cavities A and C are classified as reservoirs because they are connected to only one channel each. Cavity B is classified as a node because it is connected to more than one channel: B is connected to both channel 125 and channel 130.

Pressure sources 135, 140 and 145 are connected to reservoir A, node B and reservoir C, respectively, via gas tubes 150, 155 and 160, respectively. Each of the three pressure sources is capable of providing at least two different pressures: a high gas pressure and a low pressure. Labels HP, IP and LP in FIG. 2 and in FIGS. 3A-3F refer to the capability of a pressure source to provide high, intermediate or low pressures, respectively. Pressure source 145 is also capable of providing a pressure that is less than atmospheric pressure; e.g., a partial vacuum.

Several different ways of making a structure like microfluidic flowchip 105 are possible. As a first example, substrate 110 may be made of glass, polydimethylsiloxane (PDMS), polyethylene terephthalate (PET), or plastic. Hydrophobic fluidic layer 115 may be made from PDMS. A mold for casting PDMS to define hydrophobic microfluidic channels may be produced with a programmable cutter for vinyl decals or defined photolithographically in an epoxy-based negative photoresist such as SU-8. After patterned PDMS is cured and removed from a mold, it may be bonded to a flat substrate. Pneumatic layer 120 may also be made from PDMS. Gas tubes may be made from polyetheretherketone (PEEK) tubing which forms convenient seals when inserted in appropriately sized holes in PDMS. Hydrophobic materials that are suitable alternatives to PDMS include polypropylene (PP), a cyclic olefin polymer (COP), a cyclic olefin copolymer (COC), fluorinated ethylene propylene (FEP) and polytetrafluoroethylene (PTFE). Published water contact angles for these materials are provided in Table 1.

TABLE 1

| Polymer Name | Critical Surface Tension (dynes/cm) | Water Contact Angle (deg) |
| --- | --- | --- |
| Cyclic Olefin Polymer (COP)/ Cyclic Olefin Copolymer (COC) | 30 | 88 |
| Polypropylene | 31.6 | 102.1 |
| Polydimethylsiloxane | 20.1 | 107.2 |
| Fluorinated ethylene propylene | 10.1 | 108.5 |
| Polytetrafluoroethylene | 10.4 | 109.2 |

In some embodiments, the polymers can be modified to increase their hydrophobicity through use of additives, surface coatings, or surface modifications.

In example microfluidic flowchips, the cross-sectional dimensions of channels 125 and 130 can be in the range of about 25 µm to about 50 µm, 100 µm, 150 µm, or 200 µm (height) by about 25 µm to about 50 µm, 100 µm, 150 µm, 200 µm, 250 µm, 300 µm, 350 µm, 400 µm, 450 µm, or 500 µm (width). The sizes of reservoirs A and C, and of node B can be between about 1 mm to about 2 mm, 2.5 mm, 3 mm, 3.5 mm, 4 mm, 4.5 mm, 5 mm, 5.5 mm, or 6 mm in diameter. The distance between reservoir A and node B can be between about 5 mm to about 25 mm, 50 mm, 75 mm or 100 mm; the distance between node B and reservoir C can be within the same range. The cross-sectional areas of the cavities in typical flowchips are approximately 100 to 400 times greater than the cross-sectional areas of the channels. Therefore the flow resistance of the channels is about 10,000 to 160,000 times greater than the flow resistance of the cavities. Alternative designs for channels and cavities including fluid flow barrier structures or configurations lead to the flow resistance of such channels being about 20%, 50%, 100%, 200%, 500%, or 1000% greater than the flow resistance of non-altered channels.

Another way to make a structure like microfluidic flowchip 105 involves hot embossing a hydrophobic thermoplastic polymer such as polypropylene (PP) or cyclic olefin polymer/copolymer (COP/COC) followed by solvent-assisted lamination to form enclosed, hydrophobic channels. A third way to make a structure like microfluidic flowchip 105 is injection molding a hydrophobic polymer such as PP, COP or COC. Finally, hydrophilic microfluidic channels, formed in polycarbonate for example, may be made hydrophobic via chemical surface treatment. There are, no doubt, other ways to make a structure containing cavities connected by hydrophobic microfluidic channels.

In some embodiments, one or more or a plurality of the cavities can be connected with up to 4, 5, 6, 7, 8, 9, 10, 11, 12, 13, 14, 15 or 16 channels each. In some embodiments, each network in the one or more networks comprises an input/output channel, the input/output channel having a greater resistance to fluid flow than that of the microfluidic channels.

3. Systems Comprising Valveless Microfluidic Flowchips

Further provided are systems comprising valveless microfluidic flowchips, including those known in the art and the valveless microfluidic flowchips described above and herein. Additionally, the systems comprise a pressure sequencer connected by pneumatic delivery channels to: (1) a high gas pressure gas source; (2) an intermediate gas pressure gas source; (3) a low pressure gas source; and optionally, (4) a partial vacuum pressure gas source; and to at least one cavity, e.g., at least two cavities, in the flowchip.

In some embodiments, the pressure sequencer is configured to apply a high gas pressure, an intermediate gas pressure, a low gas pressure, and optionally, a partial vacuum pressure to at least one cavity according to pressure sequence data, where the high gas pressure is greater than the intermediate gas pressure, the intermediate gas pressure is greater than the low gas pressure, and the low gas pressure is greater than the partial vacuum gas pressure, and the partial vacuum pressure is less than atmospheric pressure. In implementing the present systems, the flowchip can but need not additionally comprise microfluidic channels comprising a hydrostatic resistance barrier. In some embodiments, the pressure sequencer is configured to concurrently apply a combination of gas pressure and partial vacuum to at least one cavity.

Fluid transfer between cavities, e.g., between reservoirs and nodes is accomplished by switching pressures applied to each reservoir and node in a system according to a specific pattern. The following terminology aids discussion of a fluid transfer rule for the present valveless microfluidic systems. The origin or source cavity is a reservoir or node from which fluid is to be transferred. The destination cavity is the reservoir or node to which fluid is to be transferred. In some embodiments of the present systems, at least three gas pressures are used: high gas pressure, intermediate gas pressure and low gas pressure. In some embodiments of the present systems, at least four gas pressures are used: high gas pressure, intermediate gas pressure, low gas pressure and partial vacuum.

A fluid transfer rule for the present valveless microfluidic systems may be summarized in the following steps:

Step 0: Apply low pressure to all cavities.

Step 1: Apply high gas pressure to the origin or source cavity and any cavity connected to the origin or source cavity by a microfluidic channel, other than the destination cavity for a time t(1) which is a time period that is stopped or ended before the quantity of liquid is completely removed from the source cavity, e.g., a time period sufficient to allow at least about 10% and up to about 20%, 30%, 40%, 50%, 60%, 70%, 80% or 90% of the total volume of fluid in the origin or source cavity to drain into the microfluidic channel connecting the source cavity with the destination cavity. Apply low pressure to the destination and any cavity connected to the destination, other than the origin.

Step 2: Apply intermediate gas pressure to the origin or source cavity for a time t(2) sufficient to push or expel all the remaining fluid in the source cavity to drain into the microfluidic channel connecting the source cavity with the destination cavity. The application of intermediate gas pressure on the source cavity is insufficient pressure to force air into the connecting microfluidic channel. No air gap is introduced into the microfluidic channel.

Step 3: (Optional) Apply partial vacuum to the destination cavity for a time t(3) sufficient to evacuate all fluid from the cavity. This can be done with or without applying pressure to other wells depending on the desired extent of fluid removal.

Step 4: Return to Step 0 to prepare for the next fluid transfer operation.

As explained herein, the fluid transfer rule may be executed by a pressure sequencer that is configured to execute the required sequence of pressures to accomplish any desired fluid transfer operation. The pressure sequencer receives pressure sequence data and/or instructions from, e.g., a controller. These data or instructions includes step by step instructions specifying what pressure is to be applied to each reservoir and node in device in order to carry out a specific fluid transfer operation. Fluid can be moved from any reservoir to any other reservoir in a reconfigurable microfluidic system by repeating the steps of the fluid transfer rule.

In some implementations, a controller is part of a microfluidics system as described herein. Such system may be integrated with electronics or other processing logic for controlling their operation before, during, and after processing by a pressure sequencer. The processing logic may be referred to as the "controller," which may control various components or subparts of the system or systems. The controller, depending on the processing requirements and/or the type of system, may be programmed to control any of the processes disclosed herein, including the delivery of gases, pressure settings, vacuum settings, power settings, flow rate settings, fluid delivery settings, volume settings, positional and operation settings connected to or interfaced with a specific microfluidics system.

The controller may be implemented in any of various integrated circuits, logic, memory, and/or software that receive instructions, issue instructions, control operation, enable endpoint measurements, and the like. The integrated circuits may include chips in the form of memory that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a particular process. The controller may have access to computer readable media such as storage media, computer storage media, or data storage devices (removable and non-removable) such as, for example, magnetic discs, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile discs (DVD) or other optical storage, magnetic cassettes, magnetic tape, magnetic disk storage or other magnetic storage devices, or any other medium which can be used to store the information and which can be accessed by an application, module, or both. Any such computer storage media may be part of the device or accessible or connectable thereto. The computer storage media may be located remotely, e.g., cloud storage, and accessed via a network or internet connection. Any method, application or module herein described may be implemented using computer readable/executable instructions that may be stored or otherwise held by such computer readable media and executed by the one or more processors.

The controller, in some implementations, may be a part of or coupled to a computer that is integrated with, coupled to the system, otherwise networked to the system, or a combination thereof. For example, the controller may be in the "cloud" or all or a part of a host computer system, which can allow for remote access of the pressure sequencer. In some embodiments, the host computer system and/or the controller can be connected to the internet (e.g., via a wired or wireless connection). The computer may enable remote access to the system to monitor current progress of fluidic operations, examine a history of past pressure sequencing operations, examine trends or performance metrics from a plurality of pressure sequencing operations, to change parameters of current processing, to set processing steps to follow a current processing, or to start a new process. In some examples, a remote computer (e.g. a server) can provide pressure sequencing recipes to a system over a network, which may include a local network or the internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations. It should be understood that the parameters may be specific to the type of process to be performed and the type of tool that the controller is configured to interface with or control. Thus as described above, the controller may be distributed, such as by comprising one or more discrete controllers that are networked together and working towards a common purpose, such as the processes and controls described herein. An example of a distributed controller for such purposes would be one or more integrated circuits locally associated with one or more pressure sequencers in communication with one or more integrated circuits located remotely (such as part of a remote computer) that combine to control one or more pressure sequences.

As noted above, depending on the process step or steps to be performed by the pressure sequencer, the controller might communicate with one or more of other pressure sequencers in fluid communication with one or more microfluidic chips, in sequence or in parallel, a main computer, or another controller.

In addition to pressure sequencing, the controller may assist in detection of assay parameters (e.g., reservoir pressures, reservoir volumes, fluid flow rate), and biomarker detection (e.g., when performing an immunoassay). In some cases, the controller may host a user-accessible platform for invoking services, such as reporting and analysis services, and for providing computational resources to effect machine learning techniques on the detection data.

In various embodiments, the pressure sequencer can be implemented as a set of electronically controlled pneumatic valves, e.g., that are programmed using software (e.g., LabVIEW, National Instruments Corporation, MATLAB, Mathworks, Visual BASIC, C#, Python, or Java)), e.g., running on a personal computer, a microcontroller or microprocessor. In various embodiments, the pressure sequence data necessary to move fluid from one reservoir to another in a reconfigurable microfluidic device can be programmed or worked out manually. In various embodiments, a graphical software program may be written that allows a user to select origin and destination reservoirs, with the program then generating appropriate pressure sequence data by repeated application of the fluid transfer rule. In this way an intuitive system may be created that permits users to perform arbitrary microfluidic experiments without needing to understand the fluid transfer rule or other system operation details.

Examples herein show how the fluid transfer rule is used to perform common fluid transfer experiments.

FIGS. 3A-3F illustrate an implementation using the herein described systems and flowchips for transferring fluid from a source cavity (A) to a destination cavity (B) through a connecting channel. A high gas pressure (HP) is applied for a time t(1) to overcome the hydrostatic and hydrophobic barriers between the source cavity (A) and connected channel and start fluid flowing through the channel to the destination cavity (B) (See, e.g., FIGS. 3A-3C). The pressure on the source cavity (A) is then switched to an intermediate gas pressure (IP) for a time t(2) that will continue to move fluid through the channel and empty the source cavity (A) (See, e.g., FIGS. 3D-3E). The force exerted by IP is less than the amount required to overcome the resistance or fluid flow barrier(s) at the channel/cavity interface when the source cavity (A) has emptied so fluid is not pushed down the channel. The destination cavity (B) is kept at low pressure (LP, atmospheric or ambient) during this transfer. At the end of this transfer event, the source cavity (A) is empty, the connecting channel is full, and the destination cavity (B) has been filled with fluid (See, e.g., FIG. 3F). The total volume in the destination cavity (B) is the volume in the source cavity (A) minus the volume in the channel. The time t(1) is set so that at least about 10% up to about 70%, 75%, 80%, 85% or 90%, e.g., between about 30% and about 70%, of the fluid in the source cavity (A) has been transferred. The time t(2) is set for a time period that is longer than the time required to transfer the remaining fluid in the source cavity (A).

FIGS. 4A-4F illustrate an implementation using the herein described systems and flowchips for transferring fluid from a source cavity (B) to a destination cavity (C) through a connecting channel and then evacuating or removing fluid from the destination cavity (C). A high pressure (HP) is applied for a time t(1) to cavities A and B to overcome the fluid flow barriers between the source cavity (B) and channel connected to cavity C and start fluid flowing through the channel to the destination cavity (C) (See, e.g., FIGS. 4A-4B). In this scenario fluid will remain in cavity A. The pressure on cavities A and B is then switched to an intermediate pressure (IP) for a time t(2) that will continue to move fluid through the B-C channel and empty the source cavity (B) (See, e.g., FIG. 4C). The force exerted by IP is less than the amount required to overcome the resistance or fluid flow barrier(s) at the channel/cavity interface when the source cavity (B) has emptied so fluid is not pushed down the channel. The destination cavity (C) is kept at low pressure (LP, atmospheric or ambient) during this transfer. At the end of this transfer event, cavity A remains full, the source cavity (B) is empty, the connecting channel is full, and the destination cavity (C) has been filled with fluid (See, e.g., FIG. 4C). The total volume in the destination cavity (C) is the volume in the source cavity (B) minus the volume in the channel. The time t(1) is set so that at least about 10% up to about 70%, 75%, 80%, 85% or 90%, e.g., between about 30% and about 70%, of the fluid in the source cavity (B) has been transferred. The time t(2) is set for a time period that is longer than the time required to transfer the remaining fluid in the source cavity (C). The pressure on the source cavity (C) is then switched to partial vacuum (VAC) for a time t(3) and fluid is removed from the source cavity (C) and channel B-C through the gas port (See, e.g., FIGS. 4D-4E). At the end of this event, cavity A remains full and the source cavity (B), channel B-C, and destination cavity (C) are empty (See, e.g., FIG. 4F).

Figure 5:
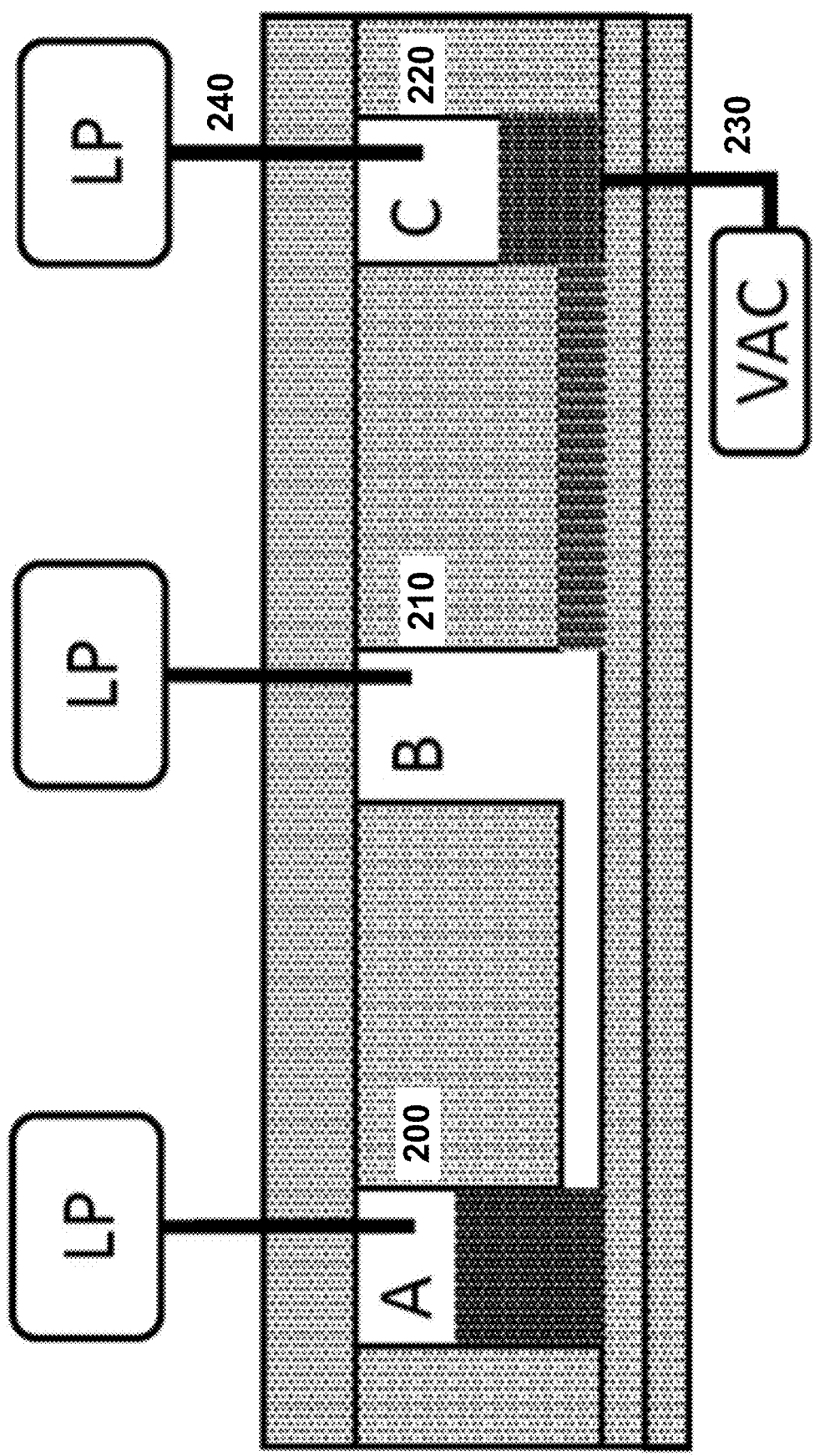
FIG. 5 illustrates a valveless microfluidic flowchip, seen in cross section with a second manifold interfaced to the bottom of the flowchip. The fluid state depicted in this cross-sectional view is identical to FIG. 6D.

Use of a single gas port to both apply pressure to and evacuate fluid from a cavity has certain limitations. If residual fluid remains in a gas line after an evacuation step, then that fluid can be pushed down into the cavity during a subsequent step when pressure is applied and gas moves through that gas line into the cavity. This can introduce undesirable effects such as cross-contamination. Furthermore, the design of a manifold and sealing to a flowchip is more complex when it needs to handle both pressure and partial vacuum. Such a system is more prone to pressure leakage over multiple fluid transfer cycles which can lead to fluid transfer errors. An improved system, shown in FIG. 5, has separate gas ports for applying pressure to and evacuating fluid from a cavity. A second manifold is interfaced to the bottom of the flowchip. A gas port is connected to this manifold at one or more cavities. Connection of the cavity to the manifold can be done through pre-formed holes in the bottom seal of the cavity or by penetration through the bottom seal of the flowchip when the flowchip is mounted on the bottom manifold (e.g., with a hollow needle). The bottom manifold can be connected to the same pressure and partial vacuum sources used for the top manifold or have separate pressure and partial vacuum sources.

FIGS. 6A-6F illustrate an implementation using the herein described systems and flowchips for transferring fluid from a source cavity (B) to a destination cavity (C) through a connecting channel and then evacuating or removing fluid from the destination cavity (C) where destination cavity (C) has separate gas ports for applying pressure and evacuating fluid. A high pressure (HP) is applied for a time t(1) to cavities A and B to overcome the hydrostatic and hydrophobic barriers between the source cavity (B) and channel connected to cavity C and start fluid flowing through the channel to the destination cavity (C) (See, e.g., FIGS. 6A-6B). In this scenario fluid will remain in cavity A. The pressure on cavities A and B is then switched to an intermediate pressure (IP) for a time t(2) that will continue to move fluid through the B-C channel and empty the source cavity (B) (See, e.g., FIG. 6C). The force exerted by IP is less than the amount required to overcome the resistance or fluid flow barrier(s) at the channel/cavity interface when the source cavity (B) has emptied so fluid is not pushed down the channel. The destination cavity (C) is kept at low pressure (LP, atmospheric or ambient) during this transfer. At the end of this transfer event, cavity A remains full, the source cavity (B) is empty, the connecting channel is full, and the destination cavity (C) has been filled with fluid (See, e.g., FIG. 6C). The pressure on the bottom gas port of source cavity (C) is then switched to partial vacuum (VAC) while the pressure on the top gas port is kept at low pressure for a time t(3) and fluid is removed from the source cavity (C) through the bottom gas port (See, e.g., FIGS. 6D-6E). At the end of this event, cavity A remains full, the channel B-C remains full, and the source cavity (B) and destination cavity (C) are empty (See, e.g., FIG. 6F).

Accordingly, provided is a system for moving a quantity of liquid from a source cavity to a destination cavity and evacuation of fluid from the destination cavity in a network of microfluidic cavities, wherein the source cavity and the destination cavity are separated by a valveless microfluidic channel having a resistance to fluid flow greater than that of the source cavity, the method comprising: (i) a receptacle for receiving and engaging with a flowchip comprising the network of microfluidic cavities; (ii) a pressure sequencer comprising a set of gas valves and configured to be connected to a first gas source for producing a high pressure in microfluidic cavities, a second gas source for producing a low pressure in microfluidic cavities, and a third gas source for producing an intermediate pressure in microfluidic cavities, and optionally a fourth source for producing a partial vacuum, wherein the high pressure is greater than the low pressure, the intermediate pressure is less than the high pressure but greater than the low pressure, and the intermediate pressure is insufficiently great to overcome resistance or barrier(s) to fluid flow in the microfluidic channel when the source cavity is substantially empty of the liquid, wherein the pressure sequencer can apply any pressure state to any cavity; and (iii) a controller configured to direct the pressure sequencer to: (a) apply the high pressure to the source cavity and to all other cavities connected to the source cavity excepting the destination cavity, while applying the low pressure to the destination cavity, to move a portion of the quantity of liquid from the source cavity, through the microfluidic channel, and to the destination cavity, and (b) apply an intermediate pressure to the source cavity before the quantity of liquid is completely removed from the source cavity, wherein the intermediate pressure is sufficiently great to push at least some of the quantity of liquid remaining after (a) to the destination cavity, but avoids introducing gas into the microfluidic channel, and (c) optionally apply a partial vacuum to evacuate fluid from one or more cavities. While not wishing to be bound by any theory, it is believed that an air-liquid interface at the entrance to the microfluidic channel (adjacent the source cavity) provides an increased resistance or barrier(s) to fluid flow that prevents further fluid transfer when the source cavity is first emptied (or substantially emptied) of the liquid. Thus, the intermediate pressure is sufficient to push fluid out of the source cavity only so long as there is fluid in the cavity. When that cavity is emptied, the resistance to fluid transfer increases such the intermediate pressure is no longer sufficient to drive fluid through the channel.

In some embodiments, the pressure sequencer is configured to apply or follow a fluid transfer rule in which: (1) high gas pressure is applied to an origin or source cavity from which a fluid is transferred and low gas pressure is applied to a destination cavity to which the fluid is transferred, the high pressure being applied for a time t(1) sufficient to overcome hydrophobic and/or hydrostatic barriers and start fluid flowing from the origin or source cavity into a microfluidic channel connecting the origin or source cavity to the destination cavity; (2) intermediate pressure is applied to the origin or source cavity and low pressure is applied to the destination cavity such that fluid continues to move through the connecting channel, the intermediate pressure being applied for a time sufficient to empty the origin or source cavity of fluid but of a pressure insufficient to expel fluid out of the channel; whereby the origin or source cavity is emptied of fluid and the fluid is moved into the channel and destination cavity; and (3) optionally, partial vacuum is applied to the destination channel while low pressure is applied to the source cavity such that fluid is evacuated from the destination cavity through the gas port. In some embodiments, partial vacuum is applied to the destination cavity through a separate port or channel located on the bottom surface of the destination cavity 220, or opposite side of the pressure ports, e.g., so that less stress is applied to the manifold/flowchip interface, and fluid is evacuated from the bottom of the cavity. In some embodiments, gas pressure is introduced into the destination cavity from the gas port above the top surface of the flowchip to facilitate removal of fluid from, and drying of the destination cavity by the partial vacuum port below the flowchip. As used herein, the terms "above" and "below" are relative because the flowchip could be held in a vertical configuration. Gas pressure is applied above the meniscus of the fluid in the destination cavity and partial vacuum is concurrently applied below the fluid in the destination cavity, e.g., on opposite sides of the fluid in the destination cavity, facilitating evacuation with continuous flow of fluid.

While not wishing to be bound by any theory, it is believed that an air-liquid interface at the entrance to the microfluidic channel (adjacent the source cavity) provides an increased resistance or barrier(s) to fluid flow that prevents further fluid transfer when the source cavity is first emptied (or substantially emptied) of the liquid. Thus, the intermediate gas pressure is sufficient to push fluid out of the source cavity only so long as there is fluid in the cavity. When that cavity is emptied, the resistance to fluid transfer increases such the intermediate gas pressure is no longer sufficient to drive fluid through the channel.

In some embodiments of the systems, the pressure sequencer is configured to apply one or more pressure modes selected from the group consisting of constant pressure, pulsing pressures, increased ramping pressures and decreased ramping pressures. In some embodiments, the pressure sequencer is configured to control applied pressure by applying pulsing pressures and using pulse width modulation (PWM), which may have a duty factor chosen to provide the desired pressure. For example, during operation, the duty factor may be adjusted to being in the range of about 1%, 5%, 10%, 20%, 30%, 40%, 50%, 60%, 70%, 80% or 90%. In some embodiments, the pressure sequencer is configured to apply increased and/or decreased ramping pressures comprising rise and/or fall times in the range of about 10 msec to about 20 msec, 50 msec, 100 msec, 250 msec, 500 msec, 750 msec or 1 sec.

As an example, high pressure can be in the range of about 5 kPa to about 100 kPa, intermediate pressure can be in the range of about 1.0 kPa to about 10 kPa, low pressure can be about 0 kPa or atmospheric or ambient pressure, and partial vacuum pressure can be less than atmospheric pressure, e.g., about −6 kPa or lower, where all pressures are gauge pressures. In some embodiments, the high pressure is in the range of about 5 kPa to about 60 kPa, 70 kPa, 80 kPa, 90 kPa or 100 kPa, e.g., in the range of about 10 kPa to about 60 kPa. In some embodiments, the intermediate pressure is in the range of about 1 kPa to about 5 kPa, 6 kPa, 7 kPa, 8 kPa, 9 kPa or 10 kPa. In some embodiments, the partial vacuum pressure is in the range of about −5 kPa to about −10 kPa, −20 kPa, −30 kPa, −40 kPa, −50 kPa, −60 kPa, −70 kPa, −80 kPa, −90 kPa, or −100 kPa. In some embodiments, fluid flow rate under high gas pressure through the first plurality of microfluidic channels is from about 0.1 µL/second to about 0.2, 0.3, 0.4, 0.5, 0.6, 0.7, 0.8, 0.9, 1.0, 2.0, 3.0, 4.0, 5.0, 6.0, 7.0, 8.0, 9.0 or 10.0 µL/second. In some embodiments, fluid flow rate under intermediate pressure through the first plurality of microfluidic channels is from about 0.01 µL/second to about 0.05, 0.1, 0.2, 0.3, 0.4, 0.5, 0.6, 0.7, 0.8, 0.9 or 1.0 µL/second. In some embodiments, a plurality of the microfluidic channels present a hydrophobic pressure barrier to fluid flow that is less than the pressure difference between the high gas pressure and the low gas pressure.

In some embodiments, the pressure sequencer is configured to apply or follow a fluid transfer rule in which: (1) high gas pressure is applied to an origin or source cavity from which a fluid is transferred and low gas pressure is applied to a destination cavity to which the fluid is transferred, the high gas pressure being applied for a time t(1) sufficient to overcome hydrophobic and/or hydrostatic barriers and start fluid flowing from the origin or source cavity into a microfluidic channel connecting the origin or source cavity to the destination cavity; and (2) intermediate gas pressure is applied to the origin or source cavity and low pressure is applied to the destination cavity such that fluid continues to move through the connecting channel, the intermediate gas pressure being applied for a time t(2) sufficient to empty the origin or source cavity of fluid but of a pressure insufficient to expel fluid out of the channel; whereby the origin or source cavity is emptied of fluid and the fluid is moved into the channel and destination cavity. In some embodiments, time t(1) is for a time period that is stopped or ended before the quantity of liquid is completely removed from the source cavity, e.g., a time period sufficient to drain at least about 10% and up to about 90% of the fluid volume from the origin or source cavity. In some embodiments, partial vacuum is applied to the destination cavity through a separate port or channel located on the bottom surface of the destination cavity 220, or opposite side of the pressure ports, e.g., so that less stress is applied to the manifold/flowchip interface, and fluid is evacuated from the bottom of the cavity. In some embodiments, gas pressure is introduced into the destination cavity from the gas port above the top surface of the flowchip to facilitate removal of fluid from, and drying of the destination cavity by the partial vacuum port below the flowchip. Again, the terms "above" and "below" are relative because the flowchip could be held in a vertical configuration. Gas pressure is applied above the meniscus of the fluid in the destination cavity and partial vacuum is concurrently applied below the fluid in the destination cavity, e.g., on opposite sides of the fluid in the destination cavity, facilitating evacuation with continuous flow of fluid.

In some embodiments, the pressure sequencer is further connected to a very high gas pressure source, and the pressure sequencer is configured to apply a very high gas pressure, wherein the very high gas pressure is greater than the high gas pressure. In some embodiments, the very high gas pressure is at least about 100 kPa, e.g., at least about 125 kPa, 150 kPa, 175 kPa, 200 kPa, or higher.

In some embodiments, the pressure sequencer is configured to apply or follow a fluid transfer rule in which the partial vacuum gas pressure is applied to a destination cavity to which a fluid is drawn via its input/output channel and low gas pressure is applied to any other cavity connected to the destination cavity by a channel.

In some embodiments, one or more networks comprise j rows and k columns of cavities, j and k being positive integers, cavities in each row or column being connected in series.

4. Methods of Use

In a further aspect, provided are methods of moving a quantity of liquid from a source cavity to a destination cavity in a network of microfluidic cavities. The methods are applicable for use in the valveless microfluidic flowchips and applying the microfluidic systems described herein, and in currently available valveless microfluidic flowchips and systems. In some embodiments, the methods employ a microfluidic flowchip having a source cavity and a destination cavity separated by a valveless microfluidic channel having a resistance to fluid flow greater than that of the source cavity. In some embodiments, the methods comprise: (a) applying a high gas pressure to the source cavity, and all other cavities connected to the source cavity excepting the destination cavity, while applying a low pressure to the destination cavity to move a portion of the quantity of liquid from the source cavity, through the microfluidic channel, and to the destination cavity, wherein the high gas pressure is greater than the low pressure; and (b) applying an intermediate gas pressure to the source cavity before the quantity of liquid is completely removed from the source cavity, wherein the intermediate gas pressure is lower than the high gas pressure but higher than low pressure, and wherein the intermediate gas pressure is sufficiently great to push at least some of the quantity of liquid remaining after (a) to the destination cavity, but insufficiently great overcome resistance to fluid flow in the microfluidic channel, and thereby avoid introducing gas into the microfluidic channel. In some embodiments, the one or more of the microfluidic channels are hydrophobic or comprise a hydrophobic coating. In some embodiments, the intermediate gas pressure is insufficiently great to introduce gas into the microfluidic channel even when all of the quantity of liquid has been removed from the source cavity. In some embodiments, less than about 90% of the liquid is removed from the source cavity before applying the intermediate gas pressure. In some embodiments, a defined amount of fluid remains in the source cavity in a region between the entrance and exit channels. In some embodiments, the method is performed using a system as described above and herein.

In a further aspect, provided are methods for arranging fluid in a microwell plate. In some embodiments, the methods comprise operating the valveless microfluidic system as described above and herein according to a set of pressure sequence data that causes the fluid to be drawn into the system from an origin or source cavity of the microwell plate and expelled into a destination cavity of the microwell plate, wherein air is not introduced into a microfluidic channel downstream of an origin or source cavity.

In a further aspect, provided are methods for performing a homogenous assay with j samples and k reagents. In some embodiments, the methods comprise operating the valveless microfluidic system as described above and herein, with pressure sequence data that causes each of the j samples to be exposed to the k reagents thereby producing j output solutions, wherein air is not introduced into a microfluidic channel downstream of an origin or source cavity.

In a further aspect, provided are methods for performing a multiplexed immunoassay. In some embodiments, the methods comprise operating the valveless microfluidic system as described above and herein, wherein the system comprises two or more networks, the system operated according to pressure sequence data such that the pressure sequencer directs fluid flows in the system that cause different kinds of sample-analyte-capture-analyte reactions to occur in different networks, but the same kind of detection reagent reaction to occur in a plurality of networks, wherein air is not introduced into a microfluidic channel downstream of an origin or source cavity. In some embodiments, the immunoassay fluid comprises a buffer having a pH in the range of 6-11, e.g., pH in the range of 6-9, e.g., a pH in the range of about 7-9 or a pH in the range of 9-11, one or more blocking agents or protein solutions and one or more surfactants. In specific embodiments, the immunoassay fluid comprises phosphate buffered saline (PBS), tris-buffered saline (TBS) or a bicarbonate buffer, albumin (e.g., bovine serum albumin (BSA)), Tween-20, Triton-X, or other surfactants and optionally glycerol.

In some embodiments, the methods can be executed analogously to the methods described in U.S. Patent Publication Nos. US2017/0021351, US2017/0021352 and US2017/0021353, with the improvement that the pressure sequencer is configured to switch from high gas pressure mode to intermediate gas pressure mode before the quantity of liquid is completely removed from the source cavity, thereby avoiding introduction of air bubbles into the microfluidic channel that connects the origin cavity with the destination cavity.

EXAMPLES

The following examples are offered to illustrate, but not to limit the claimed invention.

Example 1

Methods and Valveless Microfluidic Flowchips for Improved Fluid Control

Figures 3A, 3B, 3C, 3D, 3E, 3F:
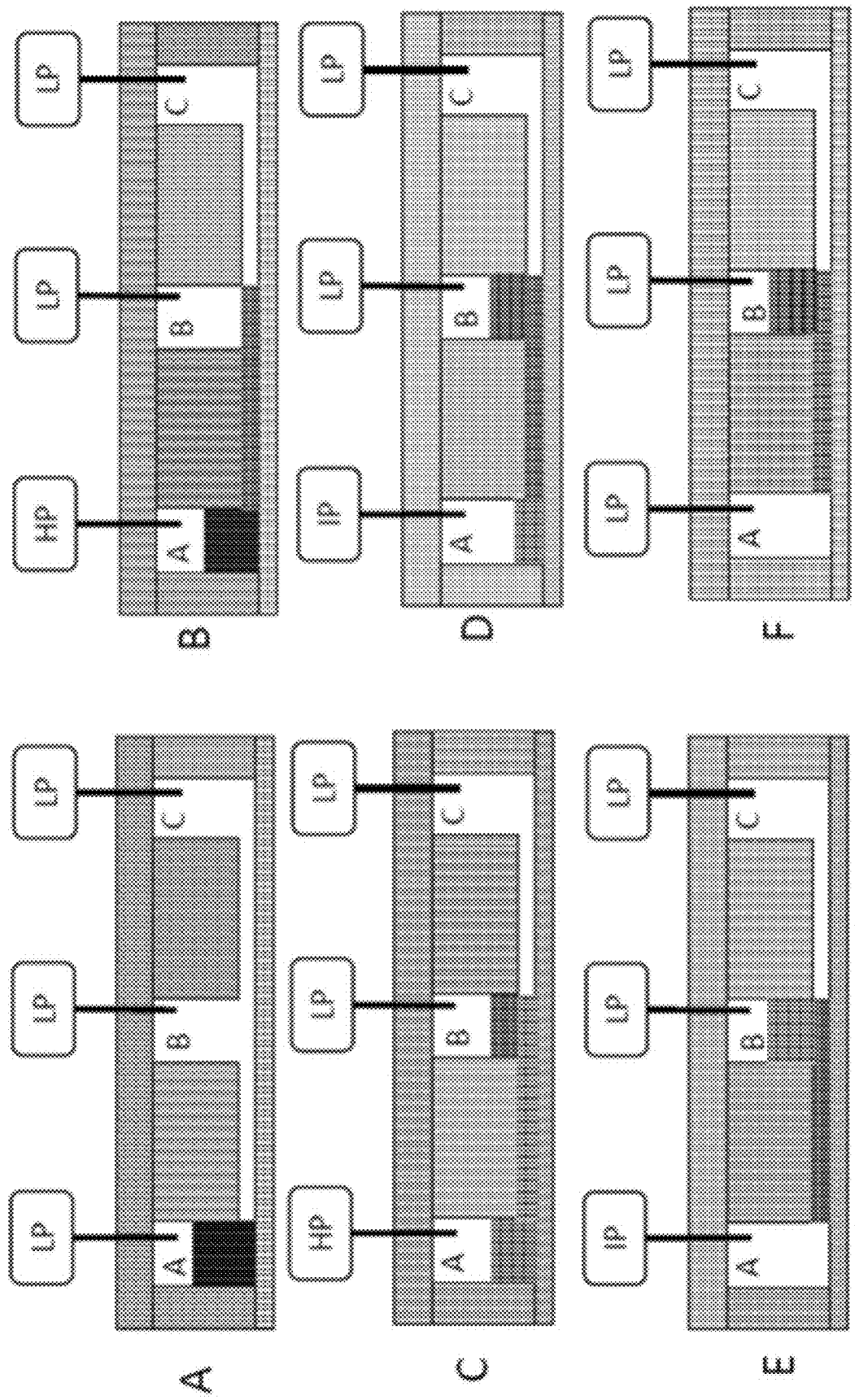
FIGS. 3A-3F illustrate a schematic of an implementation for transferring fluid from a Source well (e.g., well A) to a Destination well (e.g., well B) through a connecting channel. HP=high pressure; IP=intermediate pressure; LP=low pressure.
Figures 4A, 4B, 4C, 4D, 4E, 4F:
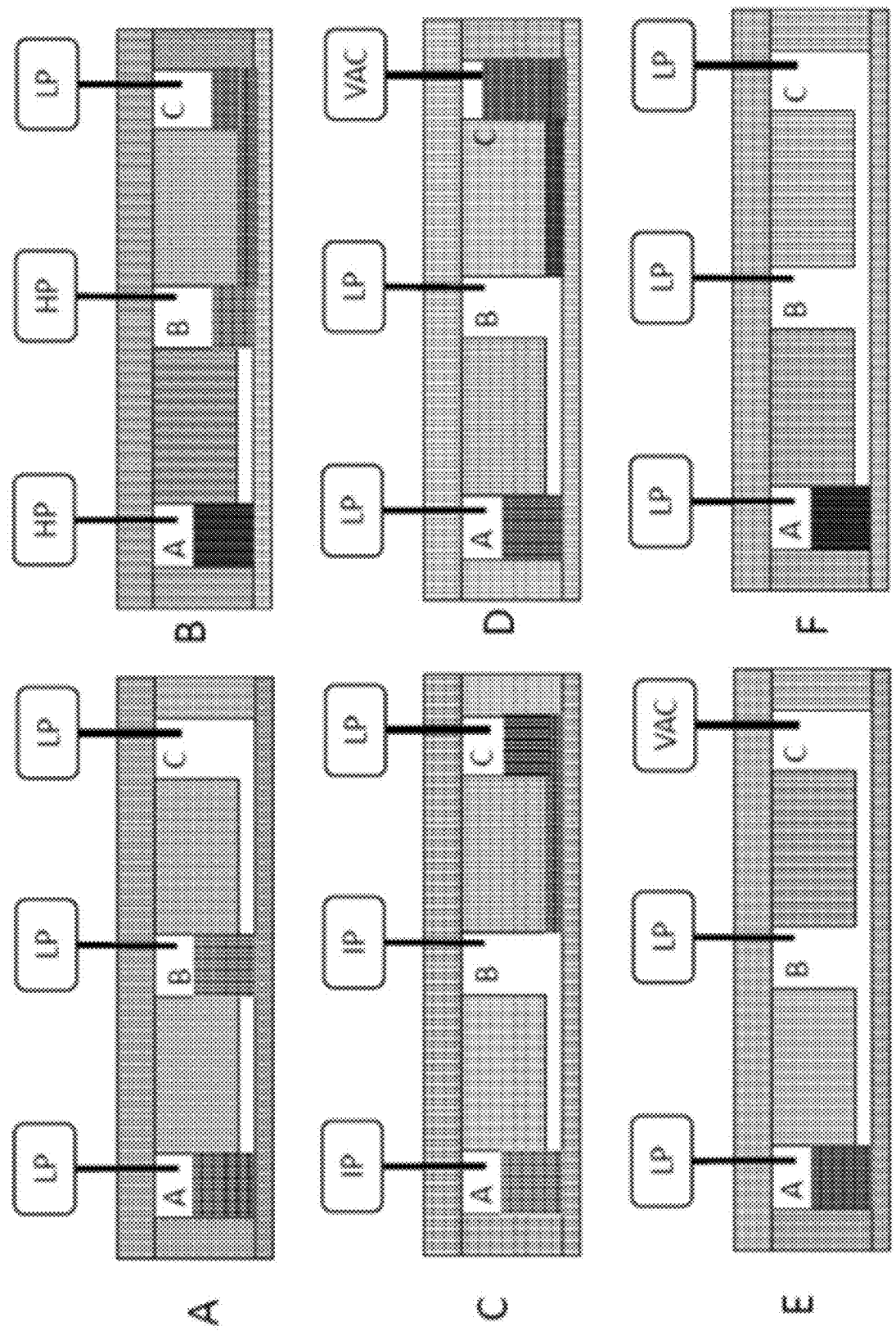
FIGS. 4A-4F illustrate a schematic of an implementation for transferring fluid from a Source well (e.g., well B) to a Destination well (e.g., well C) through a connecting channel and then evacuating the fluid from the Destination well. HP=high pressure; IP=intermediate pressure; LP=low pressure, VAC=partial vacuum.

This example illustrates implementation for transferring fluid from a source cavity to a destination cavity through a connecting channel. A schematic representation of this process is shown in FIGS. 3A-3F. A high gas pressure (HP), e.g., in the range of about 5 kPa or 10 kPa to about 60 kPa or 100 kPa, is applied for a time t(1) to overcome the hydrophobic and hydrostatic barriers between the source cavity and connected channel and start fluid flowing through the channel to the destination cavity (FIGS. 3A-3C). The pressure on the source cavity is then switched to a second, intermediate gas pressure (IP), e.g., in the range of about 0.5 kPa or 1.0 kPa to about 5 kPa or 10 kPa, for a time t(2) that will continue to move fluid through the channel and empty the source cavity (FIGS. 3D-3E). The force exerted by an intermediate gas pressure (IP) is less than the amount required to overcome the resistance or fluid flow barrier(s) at the cavity/channel interface when the source cavity has emptied so fluid is not pushed down the channel. The destination cavity is kept at a low pressure (LP, e.g., atmospheric) during this transfer. At the end of this transfer event, the source cavity is empty, the connecting channel is full, and the destination cavity has been filled with fluid (FIG. 3F). The total volume in the destination cavity is the volume in the source cavity minus the volume in the channel. The time t(1) is set so that 10% to 90% of the fluid in the source cavity has been transferred. The time t(2) is set so that is much longer than the time required to transfer the remaining fluid in the source cavity.

In one implementation using a polypropylene (PP) flowchip with channel dimensions 200 µm×50 µm×25 mm (W×H×L) the HP=30 kPa and IP=1.5 kPa which gives flow rates through the channel of about 2 µl/sec and about 0.1 µl/sec respectively. For a transfer of 20 µl, t(1)=7 sec and t(2)=120 sec. Nominally, 14 µl of fluid is transferred by HP and 6 µl of fluid by IP. The fluid should be completely transferred during the IP step after about 60 sec. The excess IP time accommodates for variation in fluid transfer rates caused by channel dimensional variations, presence of artifacts or contamination in channels, presence of air bubbles in channels, or other effects. The times t(1) and t(2) are configured so that the source cavity will not empty during the HP step and the total transfer time is minimized. The measured flowrate variation over multiple channels and multiple flowchips is approximately 12%, which gives a "3-sigma" maximum HP flowrate of 2.72 µl/sec. Under the above conditions the maximum amount of fluid transferred during HP will be 19 µl so the source cavity will not be emptied. The "3-sigma" minimum HP flowrate is 1.28 µl/sec, making the expected minimum amount of fluid transferred to be 9 µl. This means 11 µl will be transferred at the IP rate which will take 110 sec which is less than t(2). This method assures that all of the fluid will be transferred out of the source cavity, but air will not be forced through the channel and into the destination cavity. The time t(2) can be increased if desired to accommodate variations in the IP flowrate.

The resistance at the WCI is a function of the surface and fluid properties and the channel dimensions. The rectangular cross-section fluidic resistance formula is:

$$R_h = \frac{12\mu L}{\omega h^3 \left(1 - \frac{0.63h}{\omega}\right)}.$$

In this formula µ: fluid viscosity; L: channel length; ω: channel width; and H: channel height. The fluid viscosity can be optimized to increase this resistance and allow higher values of IP to be used in the process. Additives such as glycerol, and other higher viscosity fluids have been mixed into assay reagents in order to increase this resistance. These fluids will evacuate from channels at higher IP values. A useful "assay buffer" solution for flowchips made from polypropylene (PP) contains PBS+0.1% BSA+0.001% Tween 20. A useful "assay buffer" solution for flowchips made from cyclic olefin copolymer (COC) contains PBS+0.1% BSA+0.001% Tween 20+10% glycerol.

Figures 8A, 8B, 8C:
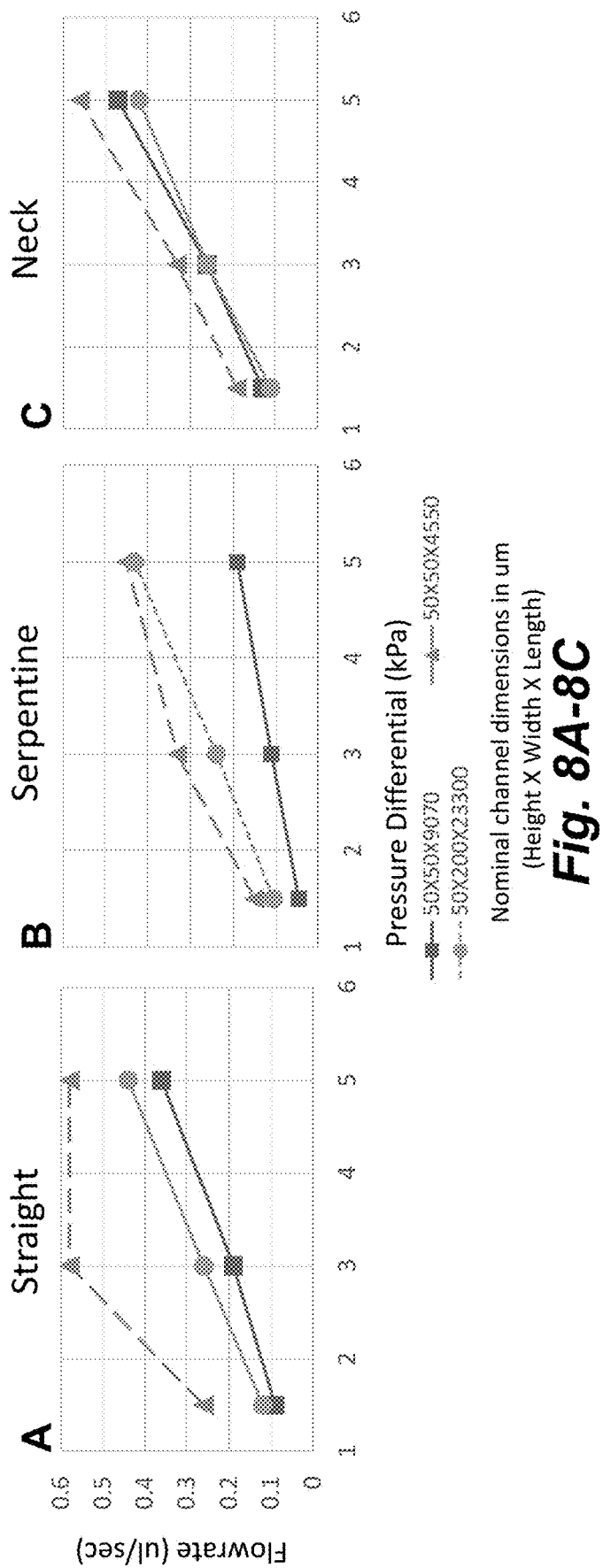
FIGS. 8A-8C illustrates the results of flowrates for an assay buffer that were measured for the three structures at different applied pressures.

In addition, the channel geometry can be modified to increase the hydrostatic barrier (HSB) for example by introducing a "neck" or a "serpentine" structure at or near the WCI. Examples of these are shown in FIGS. 7A-7C. The HSB pressures were measured for polydimethylsiloxane (PDMS) devices with these geometries and the results are given in Table 2, below, and which is also depicted in FIG. 8.

TABLE 2

|  | HPB (kPa) | HSB (kPa) |
| --- | --- | --- |
| Straight | 1.3 | 2.0 |
| Neck | 2.1 | 4.0 |
| Serpentine | 3.0 | 3.8 |

HPB-Hydrophobic Barrier
HSB-Hydrostatic Barrier

The hydrostatic resistance or fluid flow barrier structures are designed so that there is an increase in both the hydrophobic barrier (HPB), which relates to the resistance of liquid moving from a cavity into a channel, and the hydrostatic barrier (HSB), which relates to the resistance of moving liquid from a channel. It is also critical to maintain adequate flowrates so that the fluid transfers can be performed in a reasonable amount of time, however. This is especially important for time-sensitive steps in an immunoassay like the substrate incubation time. The flowrates for an assay buffer were measured for the three structures at different applied pressures and the results are shown in FIG. 8. Some reduction in flowrates were observed, but were within an acceptable range.

Figure 10:
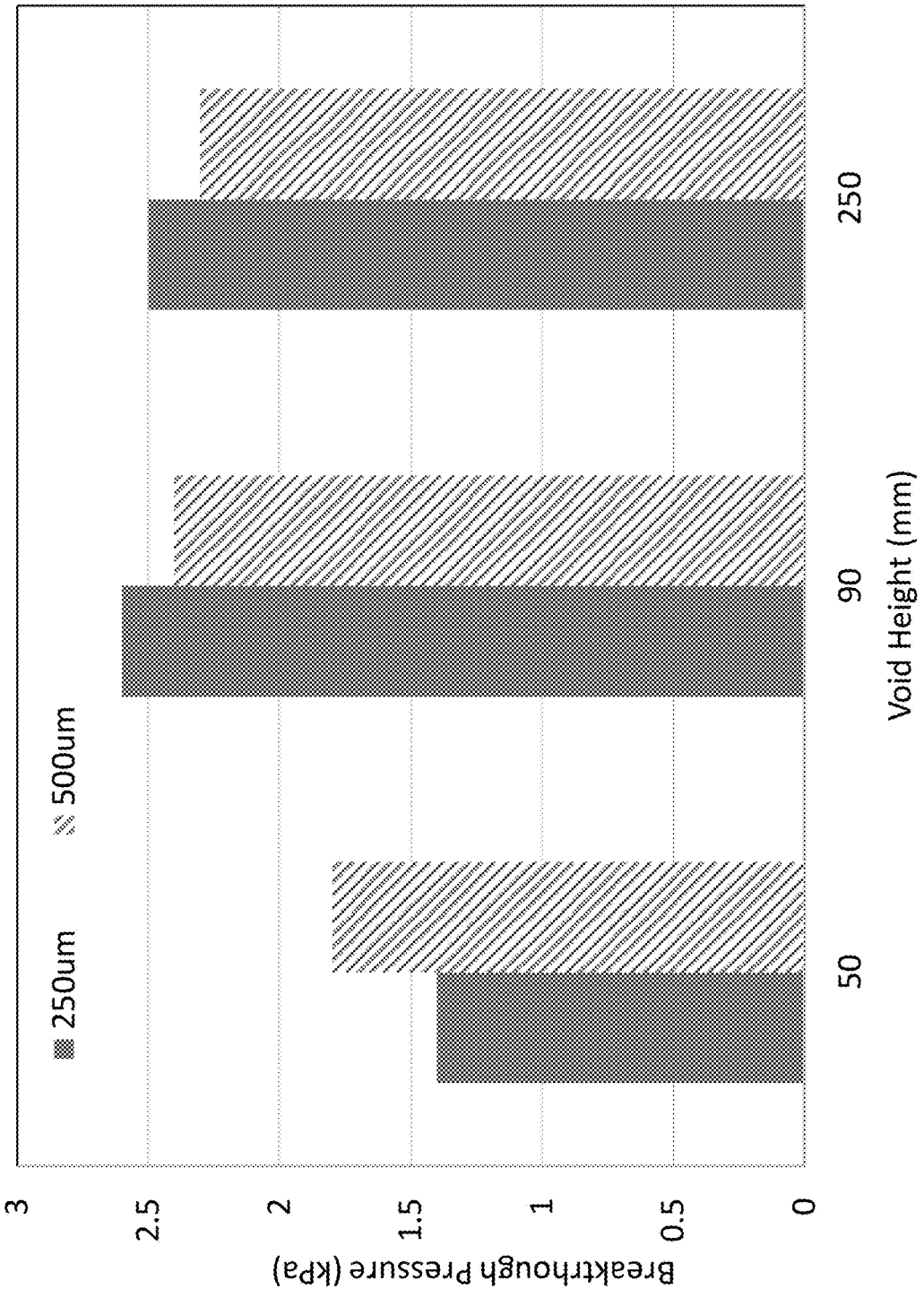
FIG. 10 illustrates the results of breakthrough pressures for void features of different heights.

In addition, the channel geometry can be modified to include a sealed cavity, or void, along the length of the channel between two regular cavities. An example of this is shown in FIGS. 9A-9B. A void is characterized by its diameter and height and the presence of a void in a channel leads to an increase in the breakthrough pressure (BP) of the channel. The BP is defined as the pressure required to move fluid from a source cavity to a destination cavity. The BPs were measured for polydimethylsiloxane (PDMS) devices with void diameters of 250 µm and 500 µm, and void heights of 90 µm and 250 µm and the results are given in FIG. 10. In these cases the channel width and height were 50 µm.

Figures 11A, 11B:
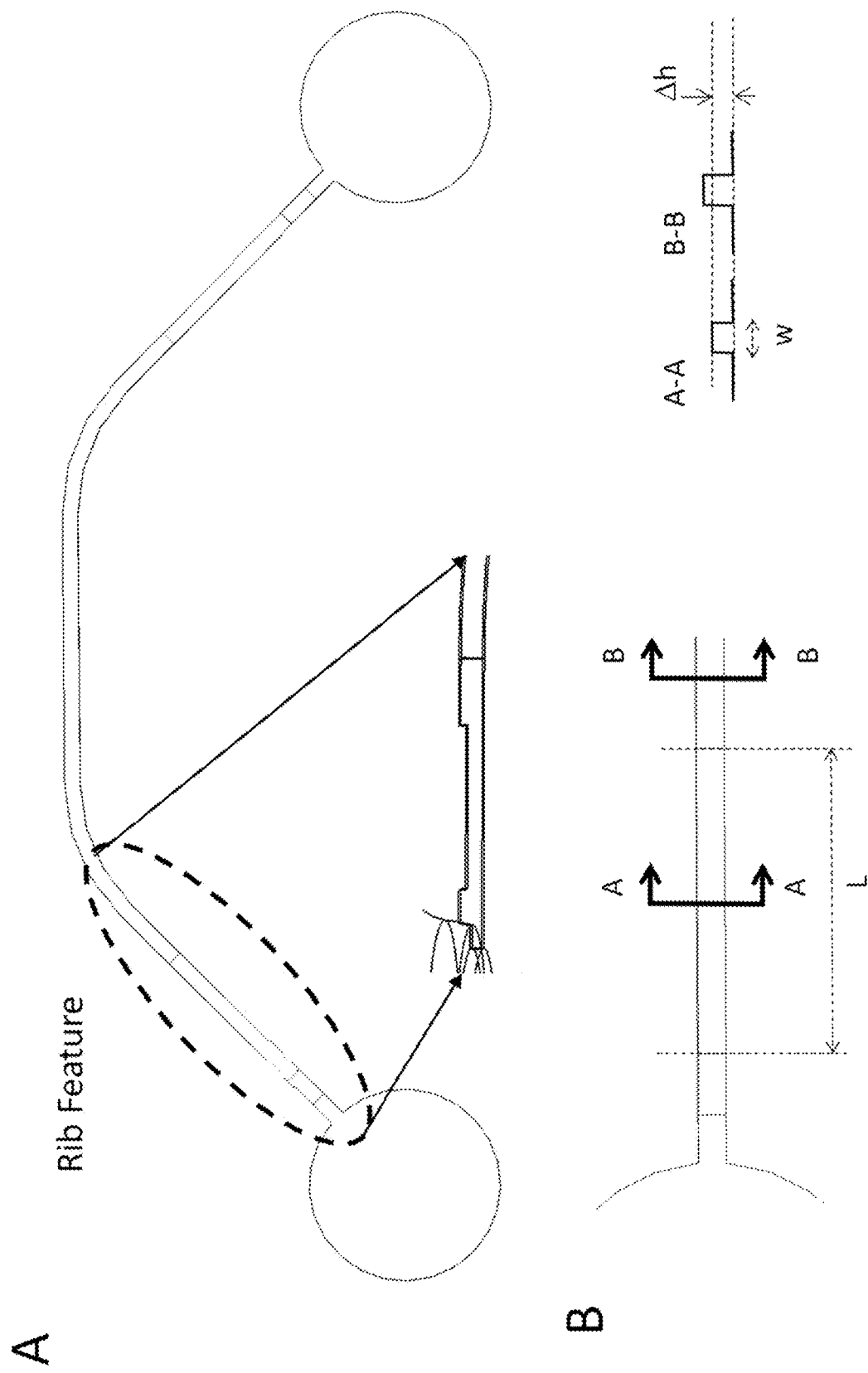
FIG. 11A-11B illustrate a rib feature that is used to increase hydrophobic barrier and hydrostatic resistance in channels. The Rib height constriction ($\Delta h$) for an about 50 μm high channel ranges from about 5 to about 40 μm. The length of the Rib constriction (L) for an about 50 μm wide (w) channel can range from about 100 to about 1000 μm. Height and length ranges are dependent on the input channel geometry.
Figure 12:
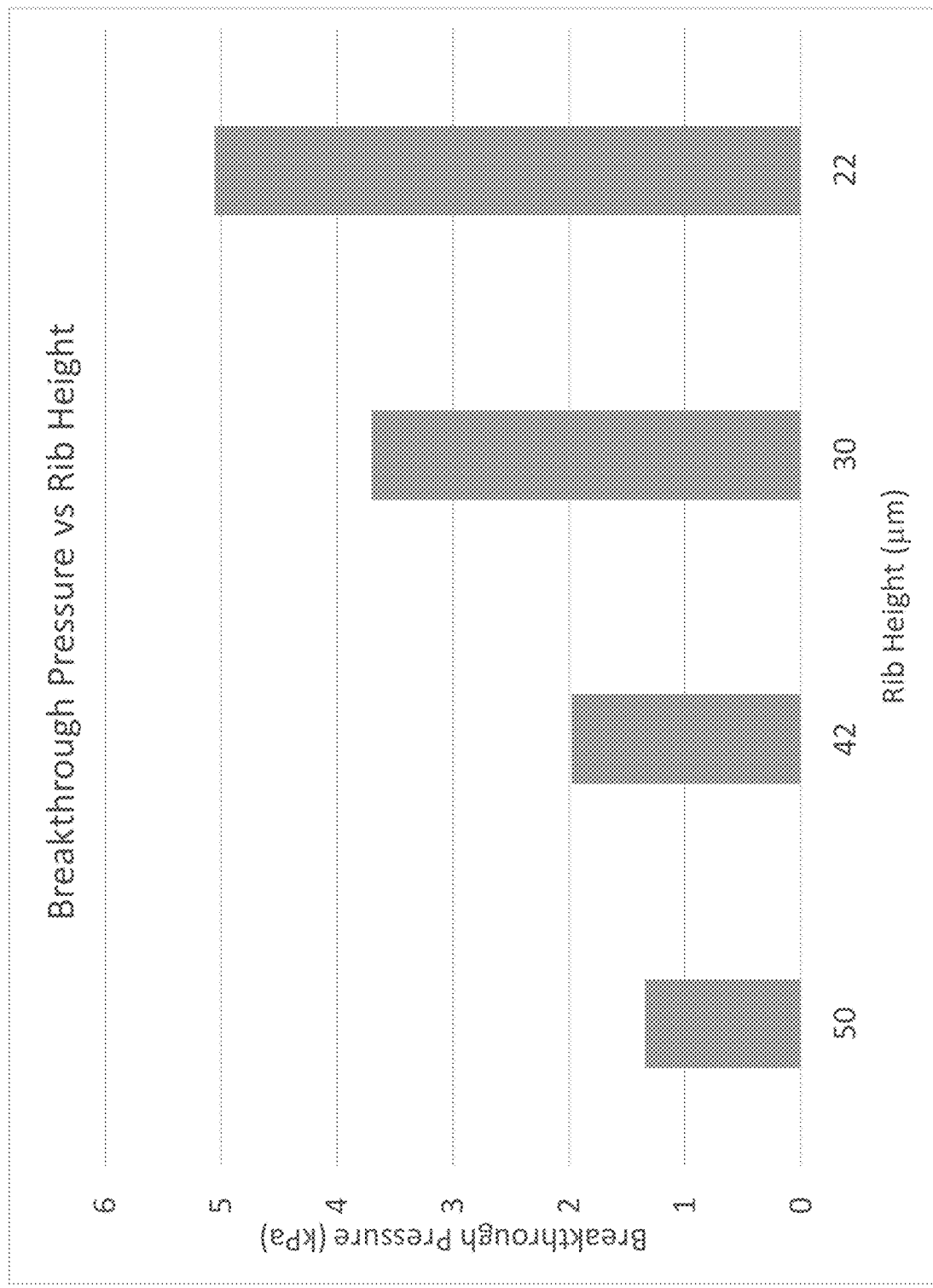
FIG. 12 illustrates the results of breakthrough pressures for rib features of different heights.
Figure 13:
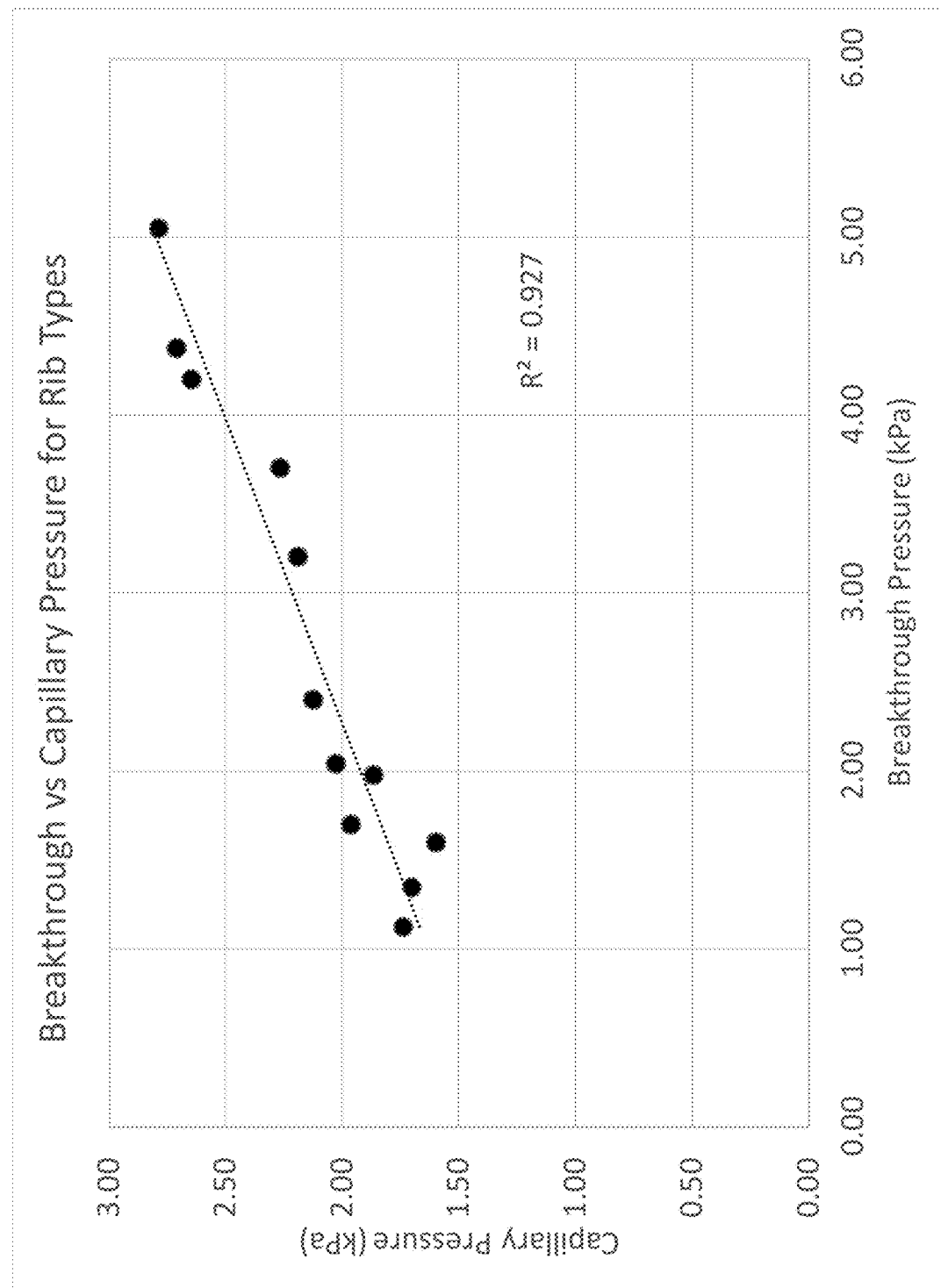
FIG. 13 illustrates the relationship between breakthrough pressure and calculated capillary pressure for rib features of different dimensions.

In addition, the channel geometry can be modified to include a region of reduced height (referred to herein as a rib or a rib feature), along the length of the channel between two cavities. An example of this is shown in FIGS. 11A-11B. A rib is characterized by its length, width, and height and the presence of a rib in a channel leads to an increase in the breakthrough pressure (BP) and capillary pressure of the channel. The BPs were measured for polydimethylsiloxane (PDMS) devices with channel widths of 50 µm and channel heights from 22 µm to 50 µm and the results are given in FIG. 12. The BPs were also compared to calculated capillary pressures for various rib geometries and those results are given in FIG. 13. A good correlation (R2=0.927) was observed between the BP and capillary pressure.

The mold for injection molded microfluidic devices is typically formed by sandwiching two sides together: an A-side and a B-side. A standard method is to have the A-side contain fluidic channel features and the B-side contain cavity and support features. Cavities are commonly formed by cylindrical pins and junctions between cavities and channels are made where the end of these pins press against raised features, or landing pads, on the A-side that define the bottom of the cavities and channel connections. Limitations of alignment of the A-side and B-side requires that the landing pads be larger than the ends of the pins so that there is always a complete connection (i.e., full contact between surfaces) between those items. An example of this is shown in FIG. 14A. The Left image in FIG. 14A shows a bottom view of the junction between a pin and a landing pad that has a single channel connection; the Middle image shows a cross sectional view of that region; the Right image shows a 3-dimensional top view of that region. A consequence of this assembly method is the formation of a lip which creates a microfluidic "ring" at the base of a cavity that is nominally the same height as the connecting channel (e.g., 50 µm). Fluid can be drawn through this ring by microcapillary forces and if two or more channels are connected to the same cavity (e.g., a node) the ring can form a microfluidic connection between those channels that can circumvent the hydrophobic barrier established between the cavity and channel. In addition, the connection geometry is flared with a radius of curvature defined by the machine tooling used to create the mold (see FIG. 14A—Right). This smoothing of the channel junction can reduce the fluid flow barrier at the WCI.

An improved device is shown in FIG. 14B. In this case, the B-side pin is larger than the A-side landing pad. This provides the necessary tolerance for alignment of the two mold sides while eliminating the lip at the base of the cavity formed by those items. This removes microfluidic connections between two or more channels that have junctions with the same cavity. An additional improvement is that channels now go straight into the cavities making a sharp change in geometry between the channel and cavity, because the junction of the channel with the cavity is perpendicular. This increases fluid flow barriers into and out of a cavity and improves the ability to control fluid transfers.

The design in FIG. 14B has all the WCIs in one plane at the bottom of a cavity. The lack of a microfluidic landing pad gap connection between channels reduces potential wicking, but fluidic connections can still be formed between two or more channels that lead to adverse effects on assay performance (e.g., cross-contamination). A further improvement of such junctions is shown in FIGS. 15A-15B. FIG. 15A shows a top 3-dimensional view of a cavity with entrance ports close to the bottom of the cavity. FIG. 15B shows a bottom 3-dimensional view of channels and their junctions with a cavity. FIG. 15C shows a cross sectional view of a Transfer Channel entrance port and an exit junction to an Assay Channel. A feature of this device is the Transfer channels enter the cavity in a plane that is above the bottom of the cavity. Fluid then exits the cavity into the Assay Channel at the bottom of the cavity. This provides a vertical separation between the junctions and further reduces the likelihood of fluidic connection between Transfer Channels and the Assay Channel. The geometry of the Entrance Port is also such that more sharp edges are formed then in the case of the device in FIG. 14B. This will further increase fluid flow barriers into and out of these channels and improve ability of the device to control fluid transfers.

Improvement in fluid control provided by the cavity features shown in FIG. 15 was measured by observing passive leakage of a high surfactant fluid from a cavity into connecting channels. Images from this study are shown in FIGS. 16A and B. An aqueous solution with 0.1% Tween 20 and fluorescein dye (for visualization) was loaded into various cavities of flowchips and let to stand for 60 minutes. The bottoms of the cavities were imaged using a fluorescence microscope (Lumascope with 4× objective, 490 excitation, 530 nm emission from Etaluma, Carlsbad CA). A positive result for passive leakage was determined if fluid was observed to travel more than 1 mm into the channel. The percentage of channels exhibiting passive leakage was used to gauge the flowchip performance. For the device shown in FIG. 14B with native COC surfaces approximately 50% of channels were observed to have passive leakage. The addition of hydrophobic surface coatings reduced this to less than 17%. The device shown in FIG. 15 with native COC surfaces exhibited no passive leakage.

The method described in this example can be extended to use of n different HP settings where n>2. This can allow for more exquisite control of fluid movements for running assays in flowchips with a wide variety of cavity and channel dimensions and multiple fluid types. For example, multiple lower HP values can be used if both low and high surface tension fluids are required to perform an assay. In another example, multiple higher HP values can be used if there are different hydrophobic barriers present in a flowchip. In one implementation a very high hydrophobic and/or hydrostatic barrier (or other barrier) can be used to keep fluids in a cavity for long term storage and/or transport. A much higher HP (e.g., >100 kPa) can be used to break this barrier. Then the assay can be performed as normal with a high HP of about 30 kPa. Vacuum can also be used in the process to evacuate fluid from cavities and channels in order to restore hydrophobic and/or hydrostatic barriers and reduce potential mixing of residual fluids in channels.

Example 2

Multiparametric Immunoassay Results

Inflammation is a complex event in which cells respond to various endogenous and exogenous stimuli. Factors such as tumor necrosis factor alpha (TNF-α), interleukin-1 beta (IL-1β), and interferon gamma (IFN-γ) activate signaling pathways leading to the expression of cell-surface antigens that facilitate binding of immune cells to blood vessels. The ability to monitor up-regulation of molecules such as the cytokines MCP-1, IL-8, IL-6 with endothelial cells provides an important physiological read-out for cell-based models of inflammation. We present results from a multiparametric primary human cell-based assay that uses immunoassays for secreted cytokines to evaluate the effect of different mediators on inflammatory response. Expression of the inflammation markers from primary human umbilical vein endothelial cells (HUVEC) stimulated with inflammation cytokines (TNF-α, IFN-γ, and IL-1β) was quantified by microfluidic-based ELISAs.

Figure 1A:
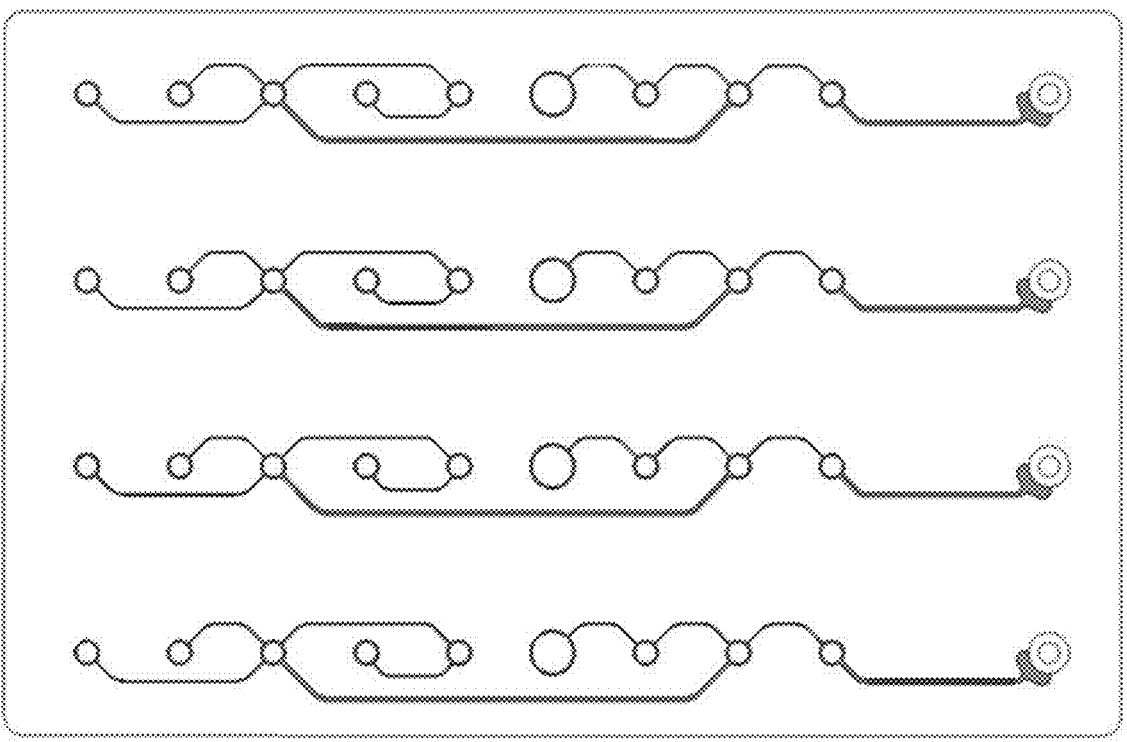
FIGS. 1A-1B. A. An example flowchip depicting 4 microfluidic networks. B. An illustrative configuration of two cavities and emanating microfluidic channels that do not have any fluid flow barrier structures or configurations.
Figure 1B:
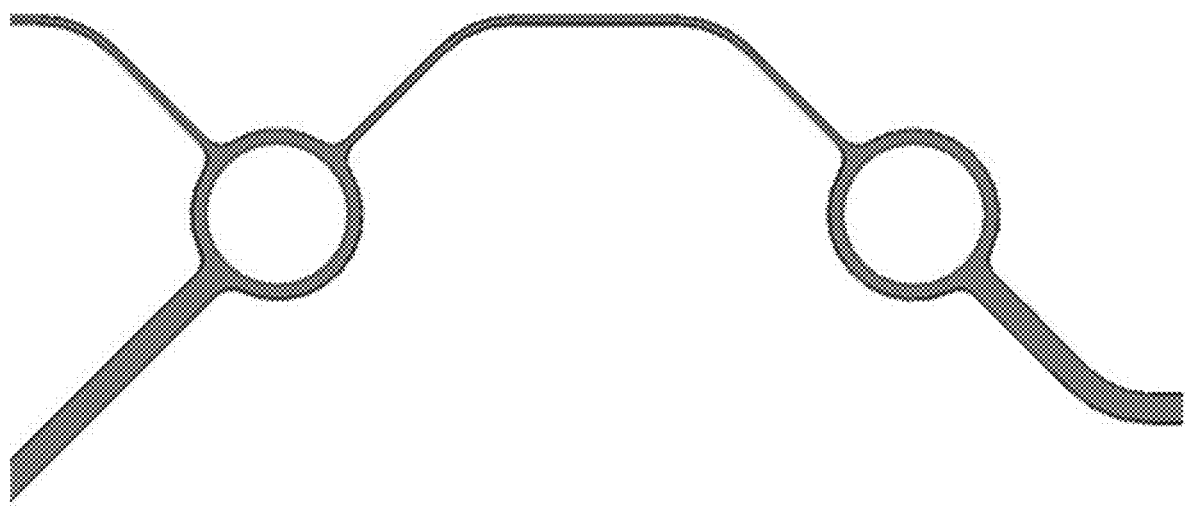

A microfluidic flowchip was designed containing multiple reservoirs and nodes that accommodate the reagents required to perform an ELISA assay. The channel layout is shown in FIG. 1A. The assay channel (from Well 3 to Well 8) has a cross-section of 50 μm by 200 μm while the other transfer channels have cross-sections of 50 μm by 50 μm. The flowchip was made out of COC using injection molding and the bottom surface was sealed with a COC film. Each reservoir has a capacity of ~30 μl and was filled with 20 μl of the appropriate assay reagent. Assays were performed using two separate protocols designated $1^{st}$ Half and $2^{nd}$ Half. In the $1^{st}$ Half the following reagents were loaded in wells as shown in FIG. 17A: Capture Antibody (W3), Blocking Buffer (W5), Sample (W2), Primary Antibody (W1), Wash 1 (W4), and Wash 2 (W7). In the $2^{nd}$ Half the following reagents were loaded in wells as shown in FIG. 17B: Wash 3 (W3), Streptavidin (SA) HRP (W5), Wash 4 (W1), Wash 5 (W7), Substrate (W2), and Stop Solution (W6). The flowchips were fully evacuated and dried in between the $1^{st}$ and $2^{nd}$ halves to reduce contamination and re-establish hydrophobic barriers at the entrance and exit of each reservoir.

The Capture and Primary antibodies are specific to each immunoassay and matched antibody pairs for the MCP-1, IL-8, and IL-6 assays were obtained from a commercial source (Biolegend, San Diego, CA). The buffers and Stop Solution are common to all three assays and were made using materials obtained from Sigma-Aldrich. The SA-HRP (Becton Dickenson, San Diego, CA) and Substrate (Abcam, Cambridge, MA) were also common to each assay. The Capture Ab's were used at a concentration of 10 μg/ml and made by diluting stock Ab in a Coating Buffer solution containing phosphate buffered saline (PBS). The Primary Ab's were used at a concentration of 1 μg/ml and made by diluting stock Ab in an Assay Buffer solution containing PBS, bovine serum albumin (BSA), and Tween20. The Blocking Buffer consisted of BSA diluted in PBS. The SA-HRP was also diluted in Assay Buffer and used at a concentration of 200 ng/ml. The Substrate solution was used as provided.

The fluid transfer steps in the protocols for the $1^{st}$ Half and $2^{nd}$ Half assays are listed in Table 3. The Source (S) and Destination (D) well numbers for each step are given in parentheses (S-D).

TABLE 3

| 1st Half Protocol | 2nd Half Protocol |
|---|---|
| 1. Incubate Capture Ab (3-8) | 1. Wash Assay Channel (3-8) |
| 2. Remove Capture Ab (8-Waste) | 2. Remove 3rd Wash (8-Waste) |
| 3. Transfer Blocking Buffer (5-3) | 3. Transfer SA-HRP (4-5, 5-3) |
| 4. Incubate Blocking Buffer (3-8) | 4. Incubate SA-HRP (3-8) |
| 5. Remove Blocking Buffer (8-Waste) | 5. Remove SA-HRP (8-Waste) |
| 6. Transfer Sample (2-3) | 6. Transfer 4th Wash (1-3) |
| 7. Incubate Sample (3-8) | 7. Wash Assay Channel (3-8) |
| 8. Remove Sample (8-Waste) | 8. Remove 4th Wash (8-Waste) |
| 9. Transfer Primary Ab (1-3) | 9. Transfer 5th Wash (7-8) |
| 10. Incubate Primary Ab (3-8) | 10. Wash Assay Channel (8-3, 3-8) |
| 11. Remove Primary Ab (8-Waste) | 11. Remove 5th Wash (8-Waste) |
| 12. Transfer 1st Wash (4-5, 5-3) | 12. Transfer Substrate (2-3) |
| 13. Wash Assay Channel (3-8) | 13. Incubate Substrate (3-8) |
| 14. Remove 1st Wash (8-Waste) | 14. Transfer Substrate (8-7, 7-6) |
| 15. Transfer 2nd Wash (7-8) | |
| 16. Wash Assay Channel (8-3, 3-8) | |
| 17. Remove 2nd Wash (8-Waste) | |
| 18. Dry Flowchip using vacuum | |

In some steps, two transfers occur as indicated by two sets of numbers in the parentheses. Each fluid transfer step, from a source well to a destination well, followed a fluid transfer rule that included a HP portion to move the majority of fluid through a given channel followed by a longer LP portion to empty the source well without emptying the channel as described previously. The HP portion typically was between 5 and 20 sec while the LP portion typically was between 30 and 300 sec. Incubation in the assay channel was done using a different fluid transfer rule that included successive short HP transfers followed by a delay between transfers to allow interaction of the reagents with the assay channel walls. Delay times were typically between 5 and 60 sec with a total of 15 to 30 cycles used during an Incubation step. The total incubation time (number of cycles×delay time) is dependent on the assay and sensitivity required: longer incubation times in general provide higher sensitivity. A LP portion was used after the HP cycles of an Incubation step in order to empty the source well. The Removal steps were accomplished by applying a vacuum to the Waste reservoir and sealing off Well 9. The time to remove 20 μl from Well 8 was typically between 15 and 30 sec. The total time for the $1^{st}$ Half protocol was approximately 90 min and the total time for the $2^{nd}$ Half protocol approximately 45 min. At the end of the $2^{nd}$ Half protocol the flowchips were removed from the system, placed in a plate reader (Tecan, Switzerland) and the absorbance at 450 nm was read through Well 6 using a pre-defined protocol.

Multiparametric inflammation response of primary human vascular endothelial cells (HUVEC) was characterized after 20 hours of stimulation with known inflammatory cytokines. HUVEC cells were cultured for 48 hours in 96-well multiwell plates (MWP) and then were incubated with a cocktail of TNF-α, IL-β, and IFN-γ at maximum concentrations of 5 ng/well, 1 ng/well, and 100 ng/well respectively. After stimulation, the cell supernatants were removed and the amount of IL-6, 11-8, and MCP-1 was measured in the supernatants using the microfluidic ELISA system. Supernatants were diluted by 4× in Assay Buffer and the amount of cytokine was quantified using a standard curve. Standard curves and fitting parameters for IL-6, 11-8, and MCP-1 are shown in FIG. 18. The upregulation of IL-6, IL-8, and MCP-1 as a function of relative cytokine mixture concentration is shown in FIG. 19. All three response cytokines were found to be upregulated at the highest inflammatory cytokine mixture concentrations after 20 hours of incubation at 37° C.

Figure 20A:
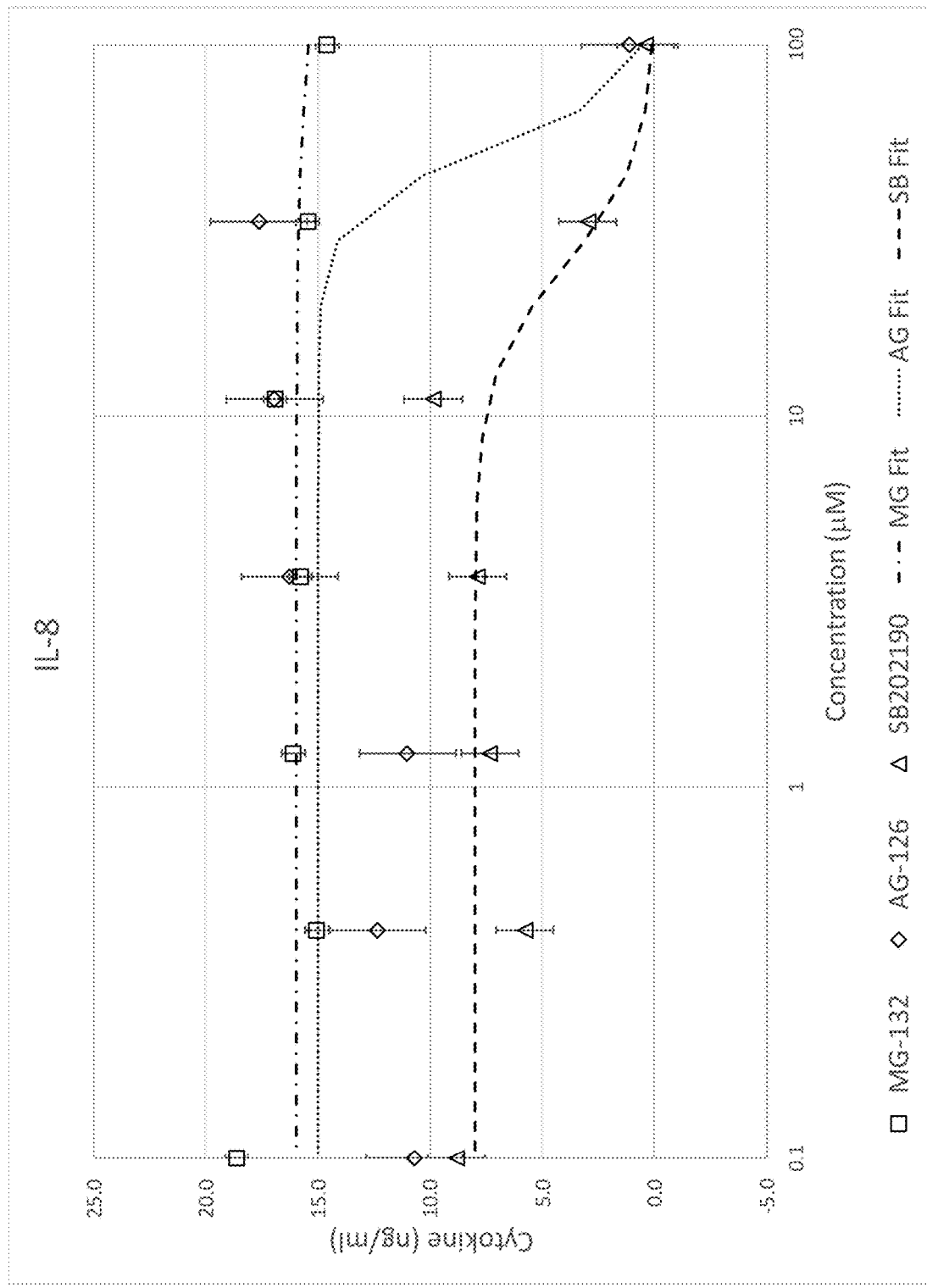
Figure 20B:
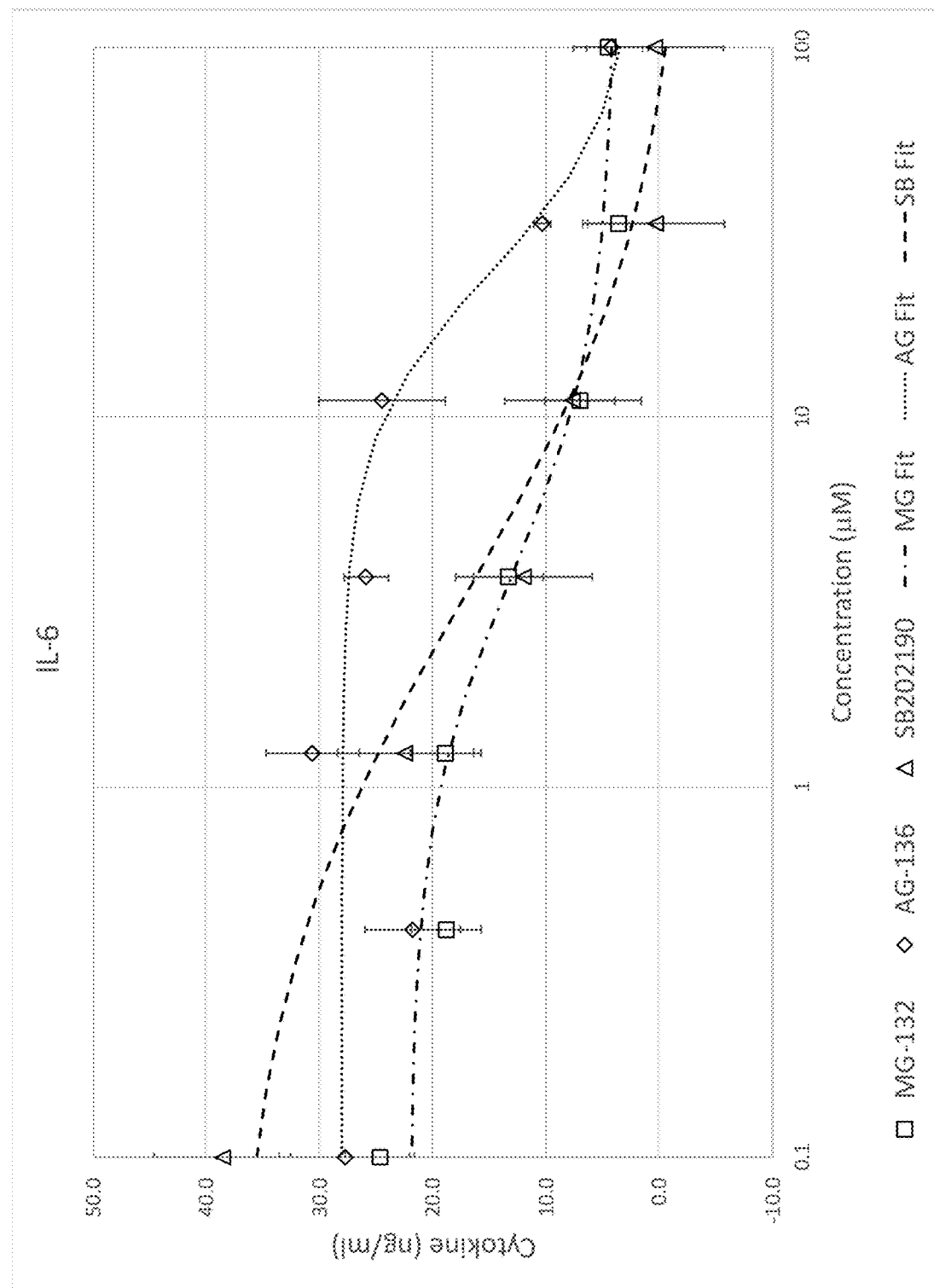
Figure 20C:
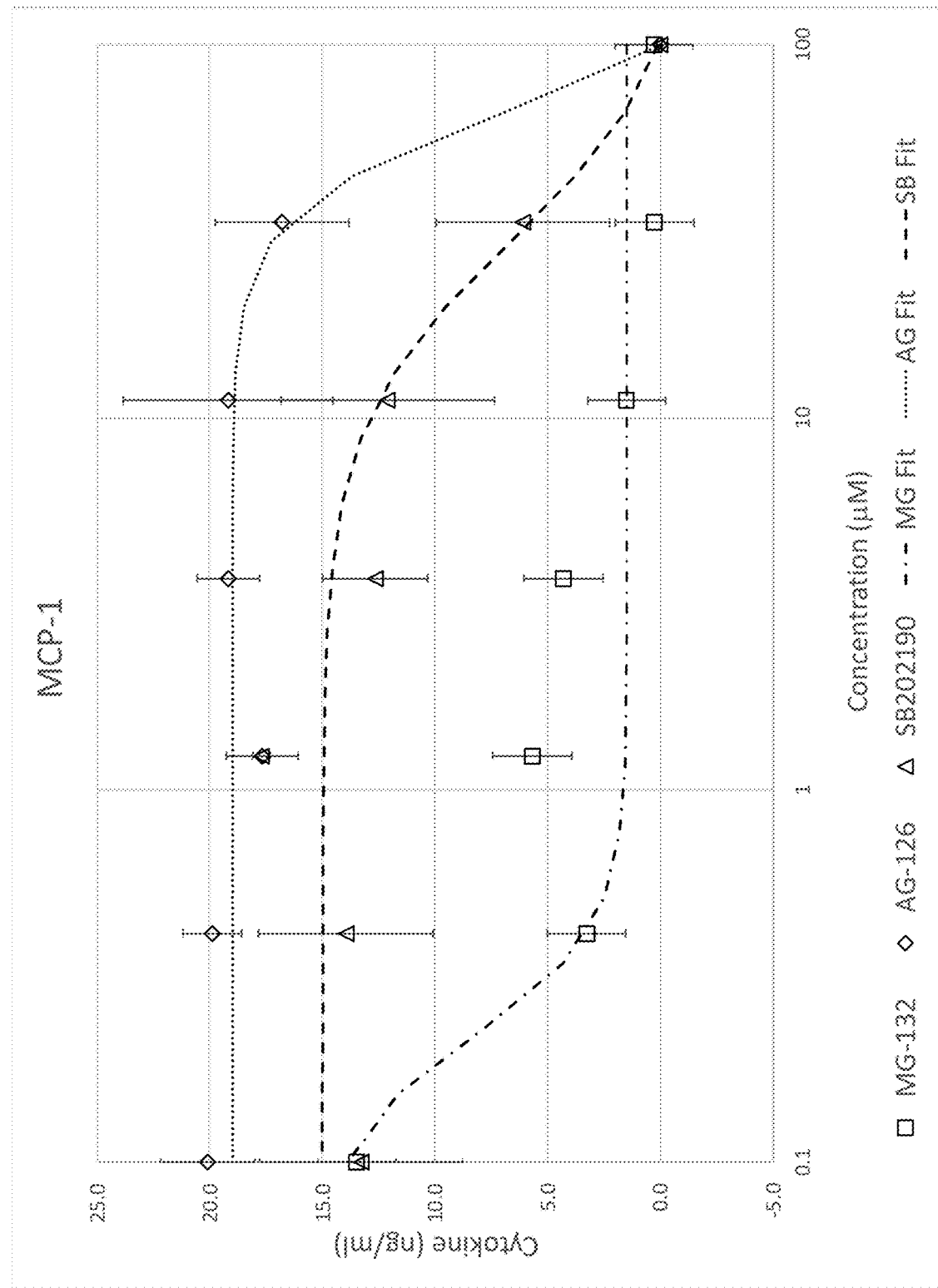

Concentration dependent effects on inflammation response of HUVECs by the anti-inflammatory compounds AG126, SB202190, and MG132 was measured. The compounds were added to HUVECs cultured in 96-well MWPs 1 hour prior to the inflammatory cytokine mixture and then the cells were incubated for 20 hours at 37° C. with both the anti-inflammatory compounds and inflammation mixture. The response curves for these compounds are shown in FIGS. 20A-20C. Each response curve was fit with a 4-parameter function and $EC_{50}$ values were measured (FIG. 20D). Clear differences in cytokine expression were seen between the compounds consistent with reported mechanisms of actions of the compounds. For example, IL-8 expression was reduced at similar concentrations by the compounds SB202190 and AG-126 which are both kinase inhibitors. However, IL-8 was not affected within the concentration range studied by MG-132 which is a proteasome inhibitor that has been reported to stimulate IL-8. This novel microfluidic ELISA system provides an efficient multiparametric assay method that can be used to test the efficacy of anti-inflammatory compounds and also provide significant insight into the mechanism of action by selective inhibition of markers triggered by different signaling pathways.

Example 3

THP-1 Cell Cytokine Secretion Assay Results

Macrophages originate from blood monocytes that leave the circulation to differentiate into various tissues. Macrophages are involved in the detection and phagocytosis of bacteria and damaged cells. In addition, macrophages initiate inflammation by releasing cytokines that activate vascular cells and facilitate adhesion of cytokines to blood vessels and migration into the tissues. Differentiated THP-1 cells have been widely used as an in vitro model of macrophages in studies of macrophage involvement in inflammatory responses. The human monocytic cell line THP-1 can be differentiated to macrophages by phorbol 12-myristate 13-acetate (PMA) and activated by LPS. Activated THP-1 cells change morphology and secrete inflammatory cytokines. Monitoring the expression levels of cytokines is an important physiological read-out for cell-based models of inflammation. Here are presented results from a multi-parametric cell-based assay that used a microfluidic flowchip to perform ELISAs for secreted cytokines to evaluate effects of pharmacological compounds on inflammatory responses. THP-1 cells were stimulated with PMA and LPS for 48 hours. An increase of IL-8, IL-1b and TNF-a was observed upon PMA and LPS activation of THP-1 cells. To evaluate anti-inflammatory compounds, cells were treated with the kinase inhibitors SB202190 and PDTC, and the antibiotic moxifloxacin prior to activation. Then, inhibition of the inflammation responses by those anti-inflammatory compounds was measured by quantifying cytokine secretion. Concentration-dependent decreases in cytokine expression were seen for the compounds SB202190, PDTC, and moxifloxacin consistent with reported mechanisms of actions.

A microfluidic flowchip was designed containing multiple reservoirs and nodes that accommodate the reagents required to perform an ELISA assay. The channel layout is shown in FIG. 21A. The assay channel (from Well 3 to Well 9) has a cross-section of 50 µm by 300 µm and length of 25 mm while the other transfer channels have cross-sections of 50 µm by 50 µm. FIG. 21B shows a zoomed region of one microfluidic network including void and rib features in transfer channels. The flowchip was made out of COC using injection molding and the bottom surface was sealed with a COC film. Each reservoir has a capacity of ~30 µl and was filled with 20 µl of the appropriate assay reagent. Assays were performed using a single protocol for all reagents as shown in FIG. 22 carried out in the following order: Capture Antibody (W3), Blocking Buffer (W2), Sample (W1), Primary Antibody (W4), Avidin-HRP (W5), Wash Buffer (Wash), Substrate (W7), and Stop Solution (W6).

The Capture and Primary antibodies are specific to each immunoassay and matched antibody pairs for the IL-8, IL-$\beta$, and TNF$\alpha$ assays were obtained from a commercial source (Biolegend, San Diego, CA). The buffers and Stop Solution are common to all three assays and were made using materials obtained from Sigma-Aldrich. The Avidin-HRP (Biolegend, San Diego, CA) and Substrate (Abcam, Cambridge, MA) were also common to each assay. The Capture Ab's were used at a concentration of 10 µg/ml and made by diluting stock Ab in a Coating Buffer solution containing phosphate buffered saline (PBS). The Primary Ab's were used at a concentration of 1 µg/ml and made by diluting stock Ab in an Assay Buffer solution containing PBS, bovine serum albumin (BSA), and Tween20. The Blocking Buffer consisted of BSA diluted in PBS. The Avidin-HRP was also diluted in Assay Buffer and used at a concentration of 200 ng/ml. The Substrate solution was used as provided.

The fluid transfer steps used in the complete assay protocol are listed in Table 4. The Source (S) and Destination (D) well numbers for each step are given in parentheses (S-D).

TABLE 4

Complete Assay Protocol

1. Incubate Capture Ab (3-9)
2. Remove Capture Ab (9-Waste)
3. Transfer Blocking Buffer (2-3)
4. Incubate Blocking Buffer (3-9)
5. Remove Blocking Buffer (9-Waste)
6. Transfer Sample (1-3)
7. Incubate Sample (3-9)
8. Remove Sample (9-Waste)
9. Transfer Primary Ab (4-3)
10. Incubate Primary Ab (3-9)
11. Remove Primary Ab (9-Waste)
12. Transfer Avi-HRP (5-3)
13. Incubate Avi-HRP (3-9)
14. Remove Avi-HRP (9-Waste)
15. Transfer $1^{st}$ Wash (Wash-8, 8-9)
16. Wash Assay Channel (9-3, 3-9)
17. Remove 1st Wash (9-Waste)
18. Transfer $2^{nd}$ Wash (Wash-8, 8-9)
19. Wash Assay Channel (9-3, 3-9)
20. Remove $2^{nd}$ Wash (9-Waste)
21. Transfer $3^{rd}$ Wash (Wash-8, 8-9)
22. Wash Assay Channel (9-3, 3-9)
23. Remove $3^{rd}$ Wash (9-Waste)
24. Transfer Substrate (7-8, 8-9)
25. Transfer Stop Solution (6-3)
26. Incubate Substrate (9-3)
27. Transfer Substrate (3-6)

In some steps, two transfers occur as indicated by two sets of numbers in the parentheses. Each fluid transfer step, from a source well to a destination well, followed a fluid transfer rule that included a HP portion to move the majority of fluid through a given channel followed by a longer LP portion to empty the source well without emptying the channel as described previously. The HP portion typically was between 5 and 20 sec while the LP portion typically was between 30 and 300 sec. Incubation in the assay channel was done using a different fluid transfer rule that included successive short HP transfers followed by a delay between transfers to allow interaction of the reagents with the assay channel walls. Delay times were typically between 5 and 60 sec with a total of 15 to 30 cycles used during an Incubation step. The total incubation time (number of cycles×delay time) is dependent on the assay and sensitivity required: longer incubation times in general provide higher sensitivity. A LP portion was used after the HP cycles of an Incubation step in order to empty the source well. The Removal steps were accomplished by applying a vacuum to the Waste port. The time to remove 20 µl from Well 9 was typically between 15 and 30 sec. The total time for the complete assay protocol was approximately 150 min. At the end of the protocol the flowchips were removed from the system, placed in a plate reader (Tecan, Switzerland) and the absorbance at 450 nm was read through Well 6 using a pre-defined protocol. The improved flowchip design incorporating voids, ribs, and channel constrictions coupled with an assay channel with larger surface area results in an improved assay performance. FIG. 23A shows standard curves for an IL-6 assay run using the flowchip device shown in FIG. 1 and using the protocol in Table 3 (FC-1) compared to that from a flowchip device in FIG. 21 using the protocol in Table 4 (FC-2). The improvement in assay performance as gauged by assay window (High Conc Signal/Blank Signal), signal standard deviation, and Limit of Detection (LOD) is given in FIG. 23B.

Inflammation response of THP-1 cells was characterized after differentiation with PMA and stimulation with LPS. Upon stimulation, differentiated THP-1 cells will adhere to the plate and secrete upregulate cytokines. THP-1 cells were plated 20,000 cells per well in a 96-well plate and incubated for 48 hr. Next, they were stimulated with a mix of PMA & LPS for 24 hr (0-5 pg/mL of PMA, and 0-100 pg/mL LPS). Anti-inflammatory compounds were added 2 hr prior to cytokine stimulation. After incubation, 60 µl of supernatant was taken for ELISA analysis from each well. The samples were analyzed fresh or stored at −70 C for subsequent analysis. Supernatants were diluted 3:1 in assay buffer and analyzed for IL-8, TNFα, and IL-β using the Pu·MA System flowchips and reagents (all Ab pairs from BioLegend). Increases in cytokine secretion of IL8 and IL-1β from stimulation with PMA and LPS are shown in FIGS. 24A-24B.

Inflammation is triggered by activation of receptors with cytokines leading to a cascade of signaling events. Kinases activate transcription factors that up-regulate adhesion molecules and cytokines (markers). Different markers are under control of different pathways and transcription factors. We investigated three known compounds that effect different parts of the inflammation pathways. 1—SB202190 a p38 MAPK inhibitor, acts on JAK/STAT and NFkB pathways. 2—PDTC an anti-oxidant, suppresses activation of NFkB. 3—Moxifloxacin inhibits the enzyme bacterial DNA gyrase and prevents replication of bacterial DNA during bacterial growth and reproduction. The response of IL-8, TNFα, and IL-1β were measured as a function of concentration of those compounds. The response curves for IL-8 are shown in FIG. 25A. Each response curve was fit with a 4-parameter function and $EC_{50}$ values were measured. The results for all three cytokines is given in FIG. 25B.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A flowchip comprising:
   a housing;
   a cavity within the housing;
   a main region within the cavity, the main region having a first height and first average cross-sectional area;
   a sample region within the cavity disposed below the main region and configured to contain a cell or cellular structure, wherein the sample region has a second height and second average cross-sectional area and the cavity is configured such that when fluid is transferred in or out of the main region, the sample region is not emptied,
   wherein the second average cross-sectional area is smaller than the first average cross-sectional area, and further comprising an input channel connected to the cavity at an entrance junction and an output channel connected to the cavity at an exit junction, wherein the entrance junction and the exit junction are located in different vertical planes, such that the input channel enters the main region and the output channel exits from the sample region.
2. The flowchip of claim 1, wherein the entrance junction is at the bottom of the main region.
3. The flowchip of claim 1, wherein the exit junction is located at the bottom of the sample region.
4. The flowchip of claim 1, wherein at least one of the input channel and the output channel is flared at the entrance junction or exit junction.
5. A flowchip comprising:
   a network of cavities connected by channels, wherein nodes are cavities connected by two or more channels each, wherein at least one node is a sample node configured to contain a solid sample, wherein the sample node comprises a main region and a sample region, the sample region disposed below the main region, the sample region having a defined volume and configured such that when a solid sample is within the sample region, fluid can be transferred to or from the main region while maintaining the solid sample within the sample region and without emptying the sample region of fluid and wherein the main region has a first height and a first average cross-sectional area, the sample region has a second height and a second average cross-sectional area, the second average cross-sectional area being smaller than the first average cross-sectional area, wherein the flowchip further comprises a first channel connected to the sample node at a first junction and second channel connected to the sample node at a second junction, wherein the first junction and section junction are located in different vertical planes.
6. The flowchip of claim 5, wherein the first junction is at the bottom of the main region.
7. The flowchip of claim 5, wherein the second junction is located at the bottom of the sample region.
8. The flowchip of claim 5, wherein the solid sample comprises cells or cellular structures.

9. The flowchip of claim 5, wherein the flowchip is configured such that absorbance through the sample region can be read.

10. The flowchip of claim 5, wherein at least one channel connected to sample node is flared at a junction with the sample node.

11. The flowchip of claim 5, further comprising an output junction at the bottom of the sample region through fluid can flowed out of the sample region.

12. The flowchip of claim 11, wherein the output junction is at the center of a bottom surface of the sample region.

13. The flowchip of claim 5, wherein the sample node comprises a housing comprising a bottom and sidewall, wherein the sample region is defined in part by a wall extending from the bottom of the bottom and set apart from the sidewall.

14. A method comprising:
providing a microfluidic flowchip comprising one or more networks of microfluidic cavities connected by microfluidic channels, wherein nodes are cavities that are connected to two or more channels each, wherein at least one node comprises a first junction with an input channel and a second junction with an output channel, wherein the first junction and the second junction are located at different vertical planes, and wherein the node comprises a main region and a defined region having a defined volume, the defined region disposed below the main region; and
directing a solid sample from the main region to the defined region.

15. The method of claim 14, wherein the solid sample comprises a cell or cellular structure.

16. The method of claim 14, wherein directing the solid sample comprises to the defined region comprises flowing fluid from the input channel through the defined region to the output channel.

17. The method of claim 14, wherein directing the solid sample comprises to the defined region comprises introducing fluid from the input channel into the main region at an angle.

18. The flowchip of claim 1, further comprising one or more additional input channels to the cavity.

* * * * *